US006994992B1

(12) United States Patent
Soto et al.

(10) Patent No.: US 6,994,992 B1
(45) Date of Patent: Feb. 7, 2006

(54) ANDROGEN-INDUCED SUPPRESSOR OF CELL PROLIFERATION AND USES THEREOF

(75) Inventors: Ana M. Soto, Boston, MA (US); Carlos Sonnenschein, Boston, MA (US); Peter Geck, Cambridge, MA (US); Jozsef Szelei, Szeged (HU)

(73) Assignee: Trustees of Tufts College, Boston, MA (US)

( * ) Notice: Subject to any disclaimer, the term of this patent is extended or adjusted under 35 U.S.C. 154(b) by 0 days.

(21) Appl. No.: 09/512,581

(22) Filed: Feb. 24, 2000

Related U.S. Application Data

(60) Provisional application No. 60/121,461, filed on Feb. 24, 1999.

(51) Int. Cl.
C12P 21/06 (2006.01)
(52) U.S. Cl. .................. 435/69.1; 536/23.1; 536/23.5; 536/24.31; 536/24.33; 435/320.1; 435/325
(58) Field of Classification Search ............... 536/23.5; 536/24.31; 435/70.1, 325, 320.1, 6
See application file for complete search history.

(56) References Cited

FOREIGN PATENT DOCUMENTS

WO WO 9731531 9/1997

OTHER PUBLICATIONS

Rae, FK, et al, 2000, Novel association of a diverse range of genes with renal cell carcinoma as identiified by differential display, Internal Journal of Cancer, vol. 88, No. 5, pp. 726-732.*
Database GenBank Accession No. BF509252, National Cancer Institute—Cancer Genome Anatomy Project, Unpublished, 1997, UI-H-B I4-aow-c-07-0-UI.s1 NCI$_{13}$CGAP$_{13}$Sub 8 *Homo sapiens* cDNA clone.*
Database GenBank Accession No. U95825, Geck, P, et al, Direct Submission, Mar. 28, 1997, Human androgen-induced prostate proliferative shutoff associated protein (AS3) mRNA, complete cds.*
Tockman, MS, et al, 1992, Considerations in bringing a cancer biomarker to clinical application, Cancer Research, vol. 52, Suppl., pp. 2711s-2718s.*
Cawthon, RM, et al, 1991, cDNA sequence and genomic structure of EV12B, a gene lying within an intron of the neurofibromatosis type 1 gene, Genomics, vol. 9, pp. 446-460.*
Ward, AM, 1985, Tumour Markers, Developmental Oncology, vol. 21, pp. 90-106.*
Database GenBank Accession No. AB023196, Ohara, et al, Direct Submission, Feb. 4, 1999, *Homo sapiens* mRNA for KIAA0979 protein, partial cds.*

Database GenBank Accession No. AC068224, Birren, et al, Direct Submission, Apr. 30, 2000, *Homo sapiens* chromosome 3 clone RP-1-660H19 map 3, Low-Pass Sequence Sampling.*
Database GenBank Accession No. AB014548, Ohara, el al, Direct Submission, May 26, 1998, *Homo sapiens* mRNA for KIAA0648 protein, partial cds.*
Database GenBank Accession No U50533, Simard, Direct Submission, Mar. 4, 1996, Human BRCA2 region, mRNA sequence CG008.*
Bowie, JU, et al, 1990, Deciphering the message in protein sequences: tolerance to amino acid substitutions, Science, vol. 247, pp. 1306-1310.*
Burgess, WH, et al, 1990, Possible dissociation of the heparin-binding and mitogenic activities of heparin-binding (acidic fibroblast) growth factor-1, J Cell Biology, vol. 111, pp. 2129-2138.*
Lazar, E, et al, 1988, Transforming growth factor alpha: mutation of aspartic acid 47 and leucine 48 results in different biological activities, Molecular and Cellular Biology, vol. 8, pp. 1247-1252.*
Critchfield GC. Disease Markers. 1999; 15: 108-11.*
Gura T. Science. Nov. 7, 1997; 278: 1041-2.*
Boehringer Mannhein Biochemicals 1994 Catalog, p. 93.*
Promega 1993/1994 Biological Research Products Catalog, p. 149.*
Skolnick J, et al. Trends Biotechnol. 2000; 18: 34-9.*
Bergers G, et al. Curr. Opin. Genetics Develop. 2000; 10: 120-7.*
Terpe K. Appl Microbiol Biotechnol. 2003; 60: 523-33.*
Knappik A, et al. Biotechniques. Oct. 1994; 17 (4): 754-61.*
Bendig MM. Genetic Eng. 1988; 7: 91-127.*
Database EMBL Nucleotide and Protein Sequences Sep. 11, 1996, AC=U50553. Human BRCA2 region.
Database EMBL Nucleotide and Protein Sequences Jan. 30, 1997, AC=Z84572. Human DNA sequence from PAC 49J10, BRCA2 gene region chromosome 13q12-13 contains ESTs.
Database EMBL Nucleotide and Protein Sequences Nov. 1, 1999, AC=Q9Y215 KIAA0979 Protien (Fragment).
Database EMBL Nucleotide and Protein Sequences Jan. 25, 2000, AC=AL137201 Novel human gene mapping to chromosome 13.
Database EMBL Nucleotide and Protein Sequences Mar. 31, 1999, AC=U95825, Human androgen-induced prostate proliferative shutoff associated protein (AS3) mRNA.

(Continued)

*Primary Examiner*—Larry R. Helms
*Assistant Examiner*—Stephen L. Rawlings
(74) *Attorney, Agent, or Firm*—Lawson & Weitzen, LLP; Sonia K. Guterman

(57) ABSTRACT

The invention provides novel AS3 nucleic acid sequences, AS3 polypeptides, anti-AS3 antibodies, and methods for modulating cell proliferation and detecting compounds that modulate cell proliferation. Diagnostic and therapeutic methods utilizing compositions of the invention are also provided.

11 Claims, 15 Drawing Sheets

OTHER PUBLICATIONS

Denison SH, et al. Mutation in the bimD gene of *Asprgillus nidulans* confers a conditional mitotic block and sensitivity to DNA damaging agents. *Genetics.* Aug. 1993;134(4):1085-96.

Geck P, et al. Expression of novel genes linked to the androgen-induced, proliferative shutoff in prostate cancer cells. *J Steroid Biochem Mol Biol.* Nov.-Dec. 1997;63(4-6):211-8.

Geck P, et al. Early gene expression during androgen-induced inhibition of proliferation of prostate cancer cells: a new suppressor candidate on chromosome 13, in the BRCA2-Rb1 locus, *J Steroid Biochem Mol Biol.* Jan. 1999;68(1-2);41-50.

Koch C, et al. A role for the transcription factors Mbp1 and Swi4 in progression from G1 to S phase. *Science.* Sep. 17, 1993;261(5128):1551-7.

Sadar MD, et al. Prostate cancer: molecular biology of early progression to androgen independence. *Endocr Relat Cancer.* Dec. 1999;6(4):487-502.

Soto AM, et al. Variants of the human prostate LNCaP cell line as tools to study discrete components of the androgen-mediated proliferative response. *Oncol Res.* 1995;7(10-11):545-58.

Soto AM, et al. The role of estrogens on the proliferation of human breast tumor cells (MCF-7). *J Steroid Biochem.* Jul. 1985;23(1):87-94.

Thiessen EU. Concerning a familial association between breast cancer and both prostatic and uterine malignancies. *Cancer.* Oct. 1974;34(4):1102-7.

Tulinius H, et al. Risk of prostate, ovarian, and endometrial cancer among relatives of women with breast cancer. *BMJ.* Oct. 10, 1992;305(6858):855-7.

Waddick KG, et al. Innovative treatment programs against cancer: II: Nuclear factor-kappaB (NF-kappaB) as a molecular target. *Biochem Pharmacol.* Jan. 1, 1999;57(1):9-17.

Zhang Y, et al. Molecular characterization of the cyclin-dependent kinase inhibitor p27 promoter. *Biochim Biophys Acta.* Sep. 12, 1997;1353(3):307-17.

* cited by examiner

```
ccggagagcc ccggagtgag cggagtagcg agtcggcaac ccggaggggt agaaatattt  60 ctgtc atg gct cat tca aag act agg acc aat gat gga aaa att aca tat  110
      Met Ala His Ser Lys Thr Arg Thr Asn Asp Gly Lys Ile Thr Tyr
      1             5                   10                  15 ccg cct ggg gtc aag gaa ata tca gat aaa ata tct aaa gag gag atg  158
Pro Pro Gly Val Lys Glu Ile Ser Asp Lys Ile Ser Lys Glu Glu Met
            20                  25                  30 gtg aga cga tta aag atg gtt gtg aaa act ttt atg gat atg gac cag  206
Val Arg Arg Leu Lys Met Val Val Lys Thr Phe Met Asp Met Asp Gln
            35                  40                  45 gac tct gaa gaa gaa aag gag ctt tat tta aac cta gct tta cat ctt  254
Asp Ser Glu Glu Glu Lys Glu Leu Tyr Leu Asn Leu Ala Leu His Leu
            50                  55                  60 gct tca gat ttt ttt ctc aag cat cct ggt aaa gat gtt cgc tta ctg  302
Ala Ser Asp Phe Phe Leu Lys His Pro Gly Lys Asp Val Arg Leu Leu
            65                  70                  75 gta gcc tgc tgc ctt gct gat att ttc agg att tat gct cct gaa gct  350
Val Ala Cys Cys Leu Ala Asp Ile Phe Arg Ile Tyr Ala Pro Glu Ala
80              85                  90                  95 cct tac aca tcc cct gat aaa cta aag gat ata ttt atg ttt ata aca  398
Pro Tyr Thr Ser Pro Asp Lys Leu Lys Asp Ile Phe Met Phe Ile Thr
                100                 105                 110 aga cag ttg aag ggg cta gag gat aca aag agc cca caa ttc aat agg  446
Arg Gln Leu Lys Gly Leu Glu Asp Thr Lys Ser Pro Gln Phe Asn Arg
            115                 120                 125 tat ttt tat tta ctt gag aac att gct tgg gtc aag tca tat aac ata  494
Tyr Phe Tyr Leu Leu Glu Asn Ile Ala Trp Val Lys Ser Tyr Asn Ile
            130                 135                 140 tgc ttt gag tta gaa gat agc aat gaa att ttc acc cag cta tac aga  542
Cys Phe Glu Leu Glu Asp Ser Asn Glu Ile Phe Thr Gln Leu Tyr Arg
145                 150                 155
```

*FIG. 1-1*

| | | | | | | | | | | | | | | |
|---|---|---|---|---|---|---|---|---|---|---|---|---|---|---|
| acc | tta | ttt | tca | gtt | ata | aac | aat | ggc | cac | aat | cag | aaa | gtc | cat | atg | 590
| Thr | Leu | Phe | Ser | Val | Ile | Asn | Asn | Gly | His | Asn | Gln | Lys | Val | His | Met |
| 160 | | | | | 165 | | | | 170 | | | | | 175 | |

```
acc tta ttt tca gtt ata aac aat ggc cac aat cag aaa gtc cat atg    590
Thr Leu Phe Ser Val Ile Asn Asn Gly His Asn Gln Lys Val His Met
160             165             170             175 cac atg gta gac ctt atg agc tct att att tgt gaa ggt gat aca gtg    638
His Met Val Asp Leu Met Ser Ser Ile Ile Cys Glu Gly Asp Thr Val
            180             185             190 tct cag gag ctt ttg gat acg gtt tta gta aat ctg gta cct gct cat    686
Ser Gln Glu Leu Leu Asp Thr Val Leu Val Asn Leu Val Pro Ala His
        195             200             205 aag aat tta aac aag caa gca tat gat ttg gca aag gct tta ctg aag    734
Lys Asn Leu Asn Lys Gln Ala Tyr Asp Leu Ala Lys Ala Leu Leu Lys
        210             215             220 agg aca gct caa gct att gag cca tat att acc act ttt ttt aat cag    782
Arg Thr Ala Gln Ala Ile Glu Pro Tyr Ile Thr Thr Phe Phe Asn Gln
    225             230             235 gtt ctg atg ctt ggg aaa aca tct atc agc gat ttg tca gag cat gtc    830
Val Leu Met Leu Gly Lys Thr Ser Ile Ser Asp Leu Ser Glu His Val
240             245             250             255 ttt gac tta att ttg gag ctc tac aat att gat agt cat ttg ctg ctc    878
Phe Asp Leu Ile Leu Glu Leu Tyr Asn Ile Asp Ser His Leu Leu Leu
            260             265             270 tct gtt tta ccc cag ctt gaa ttt aaa tta aag agc aat gat aat gag    926
Ser Val Leu Pro Gln Leu Glu Phe Lys Leu Lys Ser Asn Asp Asn Glu
        275             280             285 gag cgc cta caa gtt gtt aaa cta ctg gca aaa atg ttt ggg gca aag    974
Glu Arg Leu Gln Val Val Lys Leu Leu Ala Lys Met Phe Gly Ala Lys
        290             295             300 gat tca gaa ttg gct tct caa aac aag cca ctt tgg cag tgc tac ttg   1022
Asp Ser Glu Leu Ala Ser Gln Asn Lys Pro Leu Trp Gln Cys Tyr Leu
305             310             315 ggc agg ttt aat gat atc cat gta cca atc cgc ctg gaa tgt gtg aaa   1070
Gly Arg Phe Asn Asp Ile His Val Pro Ile Arg Leu Glu Cys Val Lys
320             325             330             335
```

*FIG. 1-2*

| | | |
|---|---|---|
| ttt gct agc cat tgt ctc atg aac cat cct gat tta gca aaa gac tta<br>Phe Ala Ser His Cys Leu Met Asn His Pro Asp Leu Ala Lys Asp Leu<br>340 345 350 | 1118 | |

| | |
|---|---|
| ttt gct agc cat tgt ctc atg aac cat cct gat tta gca aaa gac tta | 1118 |
| Phe Ala Ser His Cys Leu Met Asn His Pro Asp Leu Ala Lys Asp Leu | |
| 340 345 350 | |
| aca gag tat ctt aaa gtg agg tca cat gac cct gag gaa gct att aga | 1166 |
| Thr Glu Tyr Leu Lys Val Arg Ser His Asp Pro Glu Glu Ala Ile Arg | |
| 355 360 365 | |
| cat gat gtt att gtg tca ata gtt aca gct gct aaa aag gat att ctt | 1214 |
| His Asp Val Ile Val Ser Ile Val Thr Ala Ala Lys Lys Asp Ile Leu | |
| 370 375 380 | |
| ctg gtc aat gat cac tta ctt aat ttt gtg aga gag aga aca tta gac | 1262 |
| Leu Val Asn Asp His Leu Leu Asn Phe Val Arg Glu Arg Thr Leu Asp | |
| 385 390 395 | |
| aaa cga tgg aga gta cgc aaa gaa gcc atg atg gga ctt gcc caa att | 1310 |
| Lys Arg Trp Arg Val Arg Lys Glu Ala Met Met Gly Leu Ala Gln Ile | |
| 400 405 410 415 | |
| tat aag aaa tat gct tta cag tca gca gct gga aaa gat gct gca aaa | 1358 |
| Tyr Lys Lys Tyr Ala Leu Gln Ser Ala Ala Gly Lys Asp Ala Ala Lys | |
| 420 425 430 | |
| cag ata gca tgg atc aaa gac aaa ttg cta cat ata tat tat caa aat | 1406 |
| Gln Ile Ala Trp Ile Lys Asp Lys Leu Leu His Ile Tyr Tyr Gln Asn | |
| 435 440 445 | |
| agt att gat gat cga cta ctt gtt gaa cgg atc ttt gct caa tac atg | 1454 |
| Ser Ile Asp Asp Arg Leu Leu Val Glu Arg Ile Phe Ala Gln Tyr Met | |
| 450 455 460 | |
| gtt cct cac aat tta gaa act aca gaa cgg atg aaa tgc tta tat tac | 1502 |
| Val Pro His Asn Leu Glu Thr Thr Glu Arg Met Lys Cys Leu Tyr Tyr | |
| 465 470 475 | |
| ttg tat gcc aca ctg gat tta aat gct gtg aaa gca ttg aat gaa atg | 1550 |
| Leu Tyr Ala Thr Leu Asp Leu Asn Ala Val Lys Ala Leu Asn Glu Met | |
| 480 485 490 495 | |
| tgg aaa tgt caa aat ctg ctc cga cat caa gta aag gat ttg ctt gac | 1598 |
| Trp Lys Cys Gln Asn Leu Leu Arg His Gln Val Lys Asp Leu Leu Asp | |
| 500 505 510 | |

*FIG. 1-3*

| | | | | | | | | | | | | | | | |
|---|---|---|---|---|---|---|---|---|---|---|---|---|---|---|---|
| ttg | att | aag | caa | ccc | aaa | aca | gat | gcc | agt | gtc | aag | gcc | ata | ttt | tca | 1646 |
| Leu | Ile | Lys | Gln | Pro | Lys | Thr | Asp | Ala | Ser | Val | Lys | Ala | Ile | Phe | Ser |
| | | | 515 | | | | 520 | | | | | 525 | | | |

```
ttg att aag caa ccc aaa aca gat gcc agt gtc aag gcc ata ttt tca    1646
Leu Ile Lys Gln Pro Lys Thr Asp Ala Ser Val Lys Ala Ile Phe Ser
            515             520                 525 aaa gtg atg gtt att aca aga aat tta cct gat cct ggt aag gct cag    1694
Lys Val Met Val Ile Thr Arg Asn Leu Pro Asp Pro Gly Lys Ala Gln
        530             535             540 gat ttc atg aag aaa ttc aca cag gtg tta gaa gat gat gag aaa ata    1742
Asp Phe Met Lys Lys Phe Thr Gln Val Leu Glu Asp Asp Glu Lys Ile
545                 550                 555 aga aag cag tta gaa gta ctt gtt agt cca aca tgc tcc tgc aag cag    1790
Arg Lys Gln Leu Glu Val Leu Val Ser Pro Thr Cys Ser Cys Lys Gln
560             565                 570                 575 gct gaa ggt tgt gtg cgt gaa ata act aag aag ttg ggc aac ccc aaa    1838
Ala Glu Gly Cys Val Arg Glu Ile Thr Lys Lys Leu Gly Asn Pro Lys
                580                 585                 590 cag cct aca aat cct ttc ctg gaa atg atc aag ttt ctc ttg gag agg    1886
Gln Pro Thr Asn Pro Phe Leu Glu Met Ile Lys Phe Leu Leu Glu Arg
            595                 600                 605 ata gca cct gtg cac ata gat acc gaa tct atc agt gct ctt att aaa    1934
Ile Ala Pro Val His Ile Asp Thr Glu Ser Ile Ser Ala Leu Ile Lys
            610                 615                 620 caa gtg aac aaa tca ata gat gga aca gca gat gat gaa gat gag ggt    1982
Gln Val Asn Lys Ser Ile Asp Gly Thr Ala Asp Asp Glu Asp Glu Gly
            625                 630                 635 gtt cca act gat caa gcc atc aga gca ggt ctt gaa ctg ctt aag gta    2030
Val Pro Thr Asp Gln Ala Ile Arg Ala Gly Leu Glu Leu Leu Lys Val
640                 645                 650                 655 ctc tca ttt aca cat ccc atc tca ttt cat tct gct gaa aca ttt gaa    2078
Leu Ser Phe Thr His Pro Ile Ser Phe His Ser Ala Glu Thr Phe Glu
            660                 665                 670 tca tta ctg gct tgt ctg aaa atg gat gat gaa aaa gta gca gaa gct    2126
Ser Leu Leu Ala Cys Leu Lys Met Asp Asp Glu Lys Val Ala Glu Ala
            675                 680                 685
```

*FIG. 1-4*

```
gca cta caa att ttc aaa aac aca gga agc aaa att gaa gag gat ttt    2174
Ala Leu Gln Ile Phe Lys Asn Thr Gly Ser Lys Ile Glu Glu Asp Phe
            690                 695                 700 cca cac atc aga tca gcc ttg ctt cct gtt tta cat cac aaa tct aaa    2222
Pro His Ile Arg Ser Ala Leu Leu Pro Val Leu His His Lys Ser Lys
        705                 710                 715 aaa gga ccc ccc cgt caa gcc aaa tat gcc att cat tgt atc cat gcg    2270
Lys Gly Pro Pro Arg Gln Ala Lys Tyr Ala Ile His Cys Ile His Ala
720                 725                 730                 735 ata ttt tct agt aaa gag acc cag ttt gca cag ata ttt gag cct ctg    2318
Ile Phe Ser Ser Lys Glu Thr Gln Phe Ala Gln Ile Phe Glu Pro Leu
                740                 745                 750 cat aag agc cta gat cca agc aac ctg gaa cat ctc ata aca cca ttg    2366
His Lys Ser Leu Asp Pro Ser Asn Leu Glu His Leu Ile Thr Pro Leu
            755                 760                 765 gtt act att ggt cat att gct ctc ctt gca cct gat caa ttt gct gct    2414
Val Thr Ile Gly His Ile Ala Leu Leu Ala Pro Asp Gln Phe Ala Ala
        770                 775                 780 cct tgg aaa tct tgg gta gct act ttc att gtg aaa gat ctt ctc atg    2462
Pro Trp Lys Ser Trp Val Ala Thr Phe Ile Val Lys Asp Leu Leu Met
    785                 790                 795 aat gat cgg ctt cca ggg aaa aag aca act aaa ctt tgg gtt cca gat    2510
Asn Asp Arg Leu Pro Gly Lys Lys Thr Thr Lys Leu Trp Val Pro Asp
800                 805                 810                 815 gaa gaa gta tct cct gag aca atg gtc aaa att cag gct att aaa atg    2558
Glu Glu Val Ser Pro Glu Thr Met Val Lys Ile Gln Ala Ile Lys Met
                820                 825                 830 atg gtt cga tgg cta ctt gga atg aaa aat aat cac agt aaa tca gga    2606
Met Val Arg Trp Leu Leu Gly Met Lys Asn Asn His Ser Lys Ser Gly
            835                 840                 845 act tct acc tta aga ttg cta aca aca ata ttg cat agt gat gga gac    2654
Thr Ser Thr Leu Arg Leu Leu Thr Thr Ile Leu His Ser Asp Gly Asp
        850                 855                 860
```

*FIG. 1-5*

```
ttg aca gaa cag ggg aaa att agt aaa cca gat atg tca cgt ctg aga     2702
Leu Thr Glu Gln Gly Lys Ile Ser Lys Pro Asp Met Ser Arg Leu Arg
    865                 870                 875 ctt gct gct ggg agt gct att gtg aag ctg gca caa gaa ccc tgt tac     2750
Leu Ala Ala Gly Ser Ala Ile Val Lys Leu Ala Gln Glu Pro Cys Tyr
880                 885                 890                 895 cat gaa atc atc aca tta gaa caa tat cag cta tgt gca tta gct atc     2798
His Glu Ile Ile Thr Leu Glu Gln Tyr Gln Leu Cys Ala Leu Ala Ile
                900                 905                 910 aac gat gaa tgc tat caa gta aga caa gtg ttt gcc cag aaa ctt cac     2846
Asn Asp Glu Cys Tyr Gln Val Arg Gln Val Phe Ala Gln Lys Leu His
            915                 920                 925 aaa ggc ctt tcc cgt tta cgg ctt cca ctt gag tat atg gca atc tgt     2894
Lys Gly Leu Ser Arg Leu Arg Leu Pro Leu Glu Tyr Met Ala Ile Cys
        930                 935                 940 gcc ctt tgt gca aaa gat cct gta aag gag aga aga gct cat gct agg     2942
Ala Leu Cys Ala Lys Asp Pro Val Lys Glu Arg Arg Ala His Ala Arg
    945                 950                 955 caa tgt ttg gtg aaa aat ata aat gta agg cgg gag tat ctg aag cag     2990
Gln Cys Leu Val Lys Asn Ile Asn Val Arg Arg Glu Tyr Leu Lys Gln
960                 965                 970                 975 cat gca gct gtt agt gaa aaa tta ttg tct ctt cta cca gag tat gtt     3038
His Ala Ala Val Ser Glu Lys Leu Leu Ser Leu Leu Pro Glu Tyr Val
                980                 985                 990 gtt cca tat aca att cac ctt ttg gca cat gac cca gat tat gtc aaa     3086
Val Pro Tyr Thr Ile His Leu Leu Ala His Asp Pro Asp Tyr Val Lys
            995                 1000                1005 gta cag gat att gaa caa ctt aaa gat gtt aaa gaa tgt ctt tgg ttt     3134
Val Gln Asp Ile Glu Gln Leu Lys Asp Val Lys Glu Cys Leu Trp Phe
        1010                1015                1020 gtt ctg gaa ata tta atg gct aaa aat gaa aat aac agt cac gct ttt     3182
Val Leu Glu Ile Leu Met Ala Lys Asn Glu Asn Asn Ser His Ala Phe
    1025                1030                1035
```

*FIG. 1-6*

```
atc aga aag atg gta gaa aat att aaa caa aca aaa gat gcc caa gga     3230
Ile Arg Lys Met Val Glu Asn Ile Lys Gln Thr Lys Asp Ala Gln Gly
1040            1045            1050            1055 cca gat gat gca aaa atg aat gaa aaa ctg tac act gtg tgt gat gtt     3278
Pro Asp Asp Ala Lys Met Asn Glu Lys Leu Tyr Thr Val Cys Asp Val
                1060            1065            1070 gcc atg aat atc atc atg tca aag agt act aca tac agt ttg gaa tct     3326
Ala Met Asn Ile Ile Met Ser Lys Ser Thr Thr Tyr Ser Leu Glu Ser
        1075            1080            1085 cct aaa gac ccg gta cta cca gct cgt ttc ttc act caa cct gac aag     3374
Pro Lys Asp Pro Val Leu Pro Ala Arg Phe Phe Thr Gln Pro Asp Lys
            1090            1095            1100 aat ttc agt aac acc aaa aat tat ctg cct cct gaa atg aaa tca ttt     3422
Asn Phe Ser Asn Thr Lys Asn Tyr Leu Pro Pro Glu Met Lys Ser Phe
    1105            1110            1115 ttc act cct gga aaa cct aaa aca acc aat gtt cta gga gct gtt aac     3470
Phe Thr Pro Gly Lys Pro Lys Thr Thr Asn Val Leu Gly Ala Val Asn
1120            1125            1130            1135 aag cca ctt tca tca gca ggc aag caa tct cag acc aaa tca tca cga     3518
Lys Pro Leu Ser Ser Ala Gly Lys Gln Ser Gln Thr Lys Ser Ser Arg
                1140            1145            1150 atg gaa act gta agc aat gca agc agc agc tca aat cca agc tct cct     3566
Met Glu Thr Val Ser Asn Ala Ser Ser Ser Ser Asn Pro Ser Ser Pro
        1155            1160            1165 gga aga ata aag ggg agg ctt gat agt tct gaa atg gat cac agt gaa     3614
Gly Arg Ile Lys Gly Arg Leu Asp Ser Ser Glu Met Asp His Ser Glu
            1170            1175            1180 aat gaa gat tac aca atg tct tca cct ttg ccg ggg aaa aaa agt gac     3662
Asn Glu Asp Tyr Thr Met Ser Ser Pro Leu Pro Gly Lys Lys Ser Asp
    1185            1190            1195 aag aga gac gac tct gat ctt gta agg tct gaa ttg gag aag cct aga     3710
Lys Arg Asp Asp Ser Asp Leu Val Arg Ser Glu Leu Glu Lys Pro Arg
1200            1205            1210            1215
```

*FIG. 1-7*

```
ggc agg aaa aaa acg ccc gtc aca gaa cag gag gag aaa tta ggt atg    3758
Gly Arg Lys Lys Thr Pro Val Thr Glu Gln Glu Glu Lys Leu Gly Met
        1220            1225            1230 gat gac ttg act aag ttg gta cag gaa cag aaa cct aaa ggc agt cag    3806
Asp Asp Leu Thr Lys Leu Val Gln Glu Gln Lys Pro Lys Gly Ser Gln
        1235            1240            1245 cga agt cgg aaa aga ggc cat acg gct tca gaa tct gat gaa cag cag    3854
Arg Ser Arg Lys Arg Gly His Thr Ala Ser Glu Ser Asp Glu Gln Gln
        1250            1255            1260 tgg cct gag gaa aag agg ctc aaa gaa gat ata tta gaa aat gaa gat    3902
Trp Pro Glu Glu Lys Arg Leu Lys Glu Asp Ile Leu Glu Asn Glu Asp
    1265            1270            1275 gaa cag aat agt ccg cca aaa aag ggt aaa aga ggc cga cca cca aaa    3950
Glu Gln Asn Ser Pro Pro Lys Lys Gly Lys Arg Gly Arg Pro Pro Lys
1280            1285            1290            1295 cct ctt ggt gga ggt aca cca aaa gaa gag cca aca atg aaa act tct    3998
Pro Leu Gly Gly Gly Thr Pro Lys Glu Glu Pro Thr Met Lys Thr Ser
            1300            1305            1310 aaa aaa gga agc aaa aaa aaa tct gga cct cca gca cca gag gag gag    4046
Lys Lys Gly Ser Lys Lys Lys Ser Gly Pro Pro Ala Pro Glu Glu Glu
        1315            1320            1325 gaa gaa gaa gaa aga caa agt gga aat acg gaa cag aag tcc aaa agc    4094
Glu Glu Glu Glu Arg Gln Ser Gly Asn Thr Glu Gln Lys Ser Lys Ser
        1330            1335            1340 aaa cag cac cga gtg tca agg aga gca cag cag aga gca gaa tct cct    4142
Lys Gln His Arg Val Ser Arg Arg Ala Gln Gln Arg Ala Glu Ser Pro
    1345            1350            1355 gaa tct agt gca att gaa tcc aca cag tcc aca cca cag aaa gga cga    4190
Glu Ser Ser Ala Ile Glu Ser Thr Gln Ser Thr Pro Gln Lys Gly Arg
        1360            1365            1370            1375 gga aga cca tca aaa acg cca tca cca tca caa cca aaa aaa aat gtg    4238
Gly Arg Pro Ser Lys Thr Pro Ser Pro Ser Gln Pro Lys Lys Asn Val
            1380            1385            1390
```

*FIG. 1-8*

```
taagttgtaa atattacatt tcaaaccaat ttcaaattat tttgcaaaag ttcctaaatt 4298
End tgtaaacata catattgctg tatttaaatt ccatatattt agccccatta cactaggtac 4358 ggcggcgaag tgctaaaagg gaacggcgat gaacaaatgt aattaataac tttctctgtg 4418 aaagctttgg aaaaatcttt tttttttttt ttttttttg gtcaagcttg aggctgaata 4478 aagcctttga tgcacaaaat gggactgctg aagagtggac agttggacct tactttggtg 4538 accccataca tttgtggtca catgctttag ccatacacat ggtaacattg actatggagt 4598 cttgtgaaag tgtaatgtgc gatggctatg tagacataaa gaagaaactt gtaaatatct 4658 tttttctttt ttttaatgtt tctgatttct gaagtgcttg tatagctttt atctgcggct 4718 ttaaactgac agtacccgac tgtttattgg atctattgat ttgaaaagaa tttgttagga 4778 tagatcttaa gcagtaatct gtcagtgttt gtatttgtat tttctgcaat tttactgtga 4838 aaaaaaattt gttttcaaca attggtgtca ttttcttgat gtcactattt gttggagagt 4898 taaatggtct cttccctttg tgtatcttac ctagtgttta ctcctgggca cccttaatct 4958 tcagaggtgc taaattgtct gccattacac cagaaggatg cctctgatag gaggacaacc 5018 atgcaaattg tgaaatagtc ctgaagttct tggattactt tacacctcag tattgatttg 5078 tcccagaatt ttctggcctt tcatggcaat gaaaatttta agaagaaaga tttaaagtat 5138 tttaatttta aagagtgtgt tataaaataa tgtactgaat tctttatccc attttatcat 5198 cctttcagtt tttattaatc tactgtatca ataaaattct gtaatttgaa tgagtaaaaa 5258 aaaaaaaaaa aaa                                                    5271
```

*FIG. 1-9*

```
 55                                                         117
 LYLNLALHLASDFFLKHPGKDVRLLVACCLADIFRIYAPEAPYTSPDKLKDIFMFITRQLKGL 196           217                   241                    277
 LDTVLVNLVPAHKNLNKQAYDL    LMLGKTSISDLSEHVFDLILELYNIDSHLLLSVLPQL 319                         355                375
 LGRFNDIHVPIRLECVKFASHCLMNHPDLAKDLTEYL    VTAAKKDILLVNDHLLNFVRERTLDKRWRV
                                                                      404
```

*FIG. 2*

| Hank's conserved regions: | Subdomain I | | | Subdomain II | Subdomain III |
|---|---|---|---|---|---|
| Consensus: | β-strand | Mg-ATP binding loop (GxGxxGxV) | β-strand 2 | β-strand 3 (xxxKxxx) | α-helix C (xxxxExxx) |
| AS3 position: | 419 | 426 | 453 | 472 | 489 |
| AS3 sequence: | YALQ.SA | GKDAAKQI | LLIVERIF | ERM K CLYYLYA | VKALN E MWKC |
| Similar protein kinase sequences: | YTLGVSA (Elm1) | GeDrfGkV (Ror2) | LLYELMD (Yk1516) | YAM K CLKKDVI (CeTPA1) | QAFKN K MQVL (Araf) |
| | YALLNLL (Tsl) | GsGsfGdI (CK1a) | YLGEQVS (PKN2) | YAM K CLDKKRI (bARK1) | TLALN E RIML (bARK1) |
| | YHLKQNI (Cdc15) | AeGesHiS (Ypka) | YLCLCLN (BCK1) | YAM K CLDKKRI (DmGPRK1) | YTRVR E IKFI (SME1) |
| | YKlvRKI (CK1a) | HeSdfSeV (Mik1) | | VAI K CIAKKAL (CamK1) | |
| | IVLQESI (Alk5) | | | | |

| Hank's conserved regions: | Subdomain IV | Subdomain V | | Subdomain VIa | |
|---|---|---|---|---|---|
| Consensus: | β-strand 4 | β-strand 5 | α-helix D | α-helix E | |
| AS3 position: | 509 | 525 | 540 | 554 | |
| AS3 sequence: | LLDIVKDP | IFSK.VMV | GKAQDFMKK | EDDEKIRKQ.LEVL | |
| Similar protein kinase sequences: | LLDIVKDP (TPCKII) | IFSCLVME (PvpK1) | GNLQNFLKL (Let23) | ERDADAVKQILEA (CaMKIV) | |
| | LLDWFERP (Pim1) | KFSCLVME (G11a) | GSLQNFLRE (TORSO) | ECDANIMKQILSG (PfCPK) | |
| | LLGLCREA (Klg) | KFSCLVME (ZmPPK) | GNLQEYLTR (TGFbRII) | ADQLNIAKQISAG (TORRTK) | |
| | LVKLIGYC (APK1) | | | ESVIMYTKQLLL (NPK1) | |

FIG.3

```
            {42873}  1                              46  {42919}
                    CCGGAGAG....  Exon 1  ....ACCCGGAG * gtaggaa...

(13347) 47                              173 (13475)
....ttttcttgtttcag * GGGTAGAA....  Exon 2  ....GATTAAAG * gtgagta...

(16397) 174                             377 (16602)
..ttttattttgtatag * ATGGTTGT....  Exon 3  ....AACTAAAG * gcaagta...

(22832) 378                             464 (22920)
..tcttttttatttaag * GATATATT....  Exon 4  ....TACTTGAG * gtaagca...

(23028) 465                             562 (23125)
......ccttattttag * AACATTGC....  Exon 5  ....GTTATAAA * gtaagtt...

(23747) 563                             689 (23873)
.....ttttgaattgcag * CAATGGCC....  Exon 6  ....CTCATAAG * gtgagta...

(32357) 690                             854 (32439)
....tttatgttttcag * AATTTAAA....  Exon 7  ....TTACCACT * gtaagtc...

(37809) 855                             911 (37951)
...ctttctcctcaaaag * TTTTTTAA....  Exon 8  ....AATTAAAG * gtaactt...

(40437) 912                             1027 (40554)
.......ttttattttag * AGCAATGA....  Exon 9  ....TTGGGCAG * gtatatg...

(43428) 1028                            1122 (43524)
...tttatattttatcag * GTTTAATG.... Exon 10  ....CTTAACAG * gtactat...

(48471) 1123                            1268 (48617)
.....tgttatctttcag * AGTATCTT.... Exon 11  ....ACAAACGA * gtaagta...

(51727) 1269                            1420 (51880)
....tttttgttttaag * TGGAGAGT.... Exon 12  ....GATGATCG * gtaagtt...

(53049) 1421                            1534 (53164)
...tctgctttttgtag * ACTACTTG.... Exon 13  ....GCTGTGAA * gtatgtt...
```

*FIG. 5-1*

```
         (58816)  1535                              1616 (58898)
....tttgtgtttttcag * AGCATTGA.... Exon 14....AACCCAAA * gtaagta...

(61447)  1617                              1665 (61497)
...ttgtgtgatttacag * ACAGATGC.... Exon 15....TATTACAA * gtaagtt...

(64323)  1666                              1805 (64464)
.......tttattttaag * GAAATTTA.... Exon 16....GTTGTGTG * gtaagga...

(65916)  1806                              1921 (66033)
...taatctgtattacag * CGTGAAAT.... Exon 17....TCTATCAG * gtatttg...

(71527)  1922                              2027 (71633)
...ttggtcatattttag * TGCTCTTA.... Exon 18....TGCTTAAG * gtaagta...

(74539)  2028                              2188 (74700)
...tgattcatttatag * GTACTCTC.... Exon 19....ATCAGATC * gtgagtt...

(96694)  2189                              2312 (96818)
....tttttttttaatag * AGCCTTGC.... Exon 20....TATTTGAG * gtaatga...

(99765)  2313                              2471 (99925)
...tcccctcattttcag * CCTCTGCA.... Exon 21....ATGATCGG * gtaattt...

(105674)  2472                              2540 (105744)
...ctcgtttattttag * CTTCCAGG.... Exon 22....TGGTCAAA * gtgagta...

(107185)  2541                              2677 (107322)
...ttgtctcttaaatag * ATTCAGGC.... Exon 23....AAAATTAG * gtatgca...

(110571)  2678                              2801 (110696)
...ctactcattttcag * TAAACCAG.... Exon 24....CTATCAAC * gtaagga...

[4319]  2802                              3006 [4524]
....ttgtgtctttacag * GATGAATG.... Exon 25....TGTTAGTG * gtaagca...
```

*FIG. 5-2*

```
        [6829]  3007                         3121  [6945]
.....ttttcttttttcag * AAAAATTA.... Exon 26....GTTAAAGA * gtaagac...

[9074]  3122                         3254  [9208]
....tttttttttttttag * ATGTCTTT.... Exon 27....TGAATGAA * gtatgta...

[9522]  3255                         3374  [9642]
.....tatactattgcag * AAACTGTA.... Exon 28....CTGACAAG * gtagtta...

[10614] 3375                         3437  [10679]
...ttctcttggttgtag * AATTTCAG.... Exon 29....CTGGAAAA * gtatgtt...

[11561] 3438                         3583  [11709]
...catttctcatttcag * CCTAAAAC.... Exon 30....AAGGGGAG * gtaagtg...

[15476] 3584                         3689  [15583]
...tgtctgtattaaaag * GCTTGATA.... Exon 31....TTGTAAGG * gtgagat...

21107]  3690                         4129  [21548]
...ttttttttcccctag * TCTGAATT.... Exon 32....CAGCAGAG * gtaagca...

[21640] 4130                         4354  [21866]
...tcttccccaaagcag * AGCAGAAT.... Exon 33....TACACTAG * gtaagat...

[26002] 4355                         5253  [26902]
.....ctttccttttaag * GTACGGCG.... Exon 34....GAATGAGT * (poly-A)
```

*FIG. 5-3*

SEQUENCE LISTING

<160> NUMBER OF SEQ ID NOS: 72

<210> SEQ ID NO 1
<211> LENGTH: 5271
<212> TYPE: DNA
<213> ORGANISM: Homo sapiens
<220> FEATURE:
<221> NAME/KEY: CDS
<222> LOCATION: (66)..(4238)

<400> SEQUENCE: 1

```
ccggagagcc ccggagtgag cggagtagcg agtcggcaac ccggaggggt agaaatattt      60 ctgtc atg gct cat tca aag act agg acc aat gat gga aaa att aca tat     110
      Met Ala His Ser Lys Thr Arg Thr Asn Asp Gly Lys Ile Thr Tyr
        1               5                  10                  15 ccg cct ggg gtc aag gaa ata tca gat aaa ata tct aaa gag gag atg       158
Pro Pro Gly Val Lys Glu Ile Ser Asp Lys Ile Ser Lys Glu Glu Met
                 20                  25                  30 gtg aga cga tta aag atg gtt gtg aaa act ttt atg gat atg gac cag       206
Val Arg Arg Leu Lys Met Val Val Lys Thr Phe Met Asp Met Asp Gln
             35                  40                  45 gac tct gaa gaa gaa aag gag ctt tat tta aac cta gct tta cat ctt       254
Asp Ser Glu Glu Glu Lys Glu Leu Tyr Leu Asn Leu Ala Leu His Leu
         50                  55                  60 gct tca gat ttt ttt ctc aag cat cct ggt aaa gat gtt cgc tta ctg       302
Ala Ser Asp Phe Phe Leu Lys His Pro Gly Lys Asp Val Arg Leu Leu
     65                  70                  75 gta gcc tgc tgc ctt gct gat att ttc agg att tat gct cct gaa gct       350
Val Ala Cys Cys Leu Ala Asp Ile Phe Arg Ile Tyr Ala Pro Glu Ala
 80                  85                  90                  95 cct tac aca tcc cct gat aaa cta aag gat ata ttt atg ttt ata aca       398
Pro Tyr Thr Ser Pro Asp Lys Leu Lys Asp Ile Phe Met Phe Ile Thr
                100                 105                 110 aga cag ttg aag ggg cta gag gat aca aag agc cca caa ttc aat agg       446
Arg Gln Leu Lys Gly Leu Glu Asp Thr Lys Ser Pro Gln Phe Asn Arg
            115                 120                 125 tat ttt tat tta ctt gag aac att gct tgg gtc aag tca tat aac ata       494
Tyr Phe Tyr Leu Leu Glu Asn Ile Ala Trp Val Lys Ser Tyr Asn Ile
        130                 135                 140 tgc ttt gag tta gaa gat agc aat gaa att ttc acc cag cta tac aga       542
Cys Phe Glu Leu Glu Asp Ser Asn Glu Ile Phe Thr Gln Leu Tyr Arg
    145                 150                 155 acc tta ttt tca gtt ata aac aat ggc cac aat cag aaa gtc cat atg       590
Thr Leu Phe Ser Val Ile Asn Asn Gly His Asn Gln Lys Val His Met
160                 165                 170                 175 cac atg gta gac ctt atg agc tct att att tgt gaa ggt gat aca gtg       638
His Met Val Asp Leu Met Ser Ser Ile Ile Cys Glu Gly Asp Thr Val
                180                 185                 190 tct cag gag ctt ttg gat acg gtt tta gta aat ctg gta cct gct cat       686
Ser Gln Glu Leu Leu Asp Thr Val Leu Val Asn Leu Val Pro Ala His
```

-continued

```
                  195                 200                 205
aag aat tta aac aag caa gca tat gat ttg gca aag gct tta ctg aag      734
Lys Asn Leu Asn Lys Gln Ala Tyr Asp Leu Ala Lys Ala Leu Leu Lys
            210                 215                 220 agg aca gct caa gct att gag cca tat att acc act ttt ttt aat cag      782
Arg Thr Ala Gln Ala Ile Glu Pro Tyr Ile Thr Thr Phe Phe Asn Gln
225                 230                 235 gtt ctg atg ctt ggg aaa aca tct atc agc gat ttg tca gag cat gtc      830
Val Leu Met Leu Gly Lys Thr Ser Ile Ser Asp Leu Ser Glu His Val
240                 245                 250                 255 ttt gac tta att ttg gag ctc tac aat att gat agt cat ttg ctg ctc      878
Phe Asp Leu Ile Leu Glu Leu Tyr Asn Ile Asp Ser His Leu Leu Leu
                260                 265                 270 tct gtt tta ccc cag ctt gaa ttt aaa tta aag agc aat gat aat gag      926
Ser Val Leu Pro Gln Leu Glu Phe Lys Leu Lys Ser Asn Asp Asn Glu
            275                 280                 285 gag cgc cta caa gtt gtt aaa cta ctg gca aaa atg ttt ggg gca aag      974
Glu Arg Leu Gln Val Val Lys Leu Leu Ala Lys Met Phe Gly Ala Lys
        290                 295                 300 gat tca gaa ttg gct tct caa aac aag cca ctt tgg cag tgc tac ttg     1022
Asp Ser Glu Leu Ala Ser Gln Asn Lys Pro Leu Trp Gln Cys Tyr Leu
305                 310                 315 ggc agg ttt aat gat atc cat gta cca atc cgc ctg gaa tgt gtg aaa     1070
Gly Arg Phe Asn Asp Ile His Val Pro Ile Arg Leu Glu Cys Val Lys
320                 325                 330                 335 ttt gct agc cat tgt ctc atg aac cat cct gat tta gca aaa gac tta     1118
Phe Ala Ser His Cys Leu Met Asn His Pro Asp Leu Ala Lys Asp Leu
                340                 345                 350 aca gag tat ctt aaa gtg agg tca cat gac cct gag gaa gct att aga     1166
Thr Glu Tyr Leu Lys Val Arg Ser His Asp Pro Glu Glu Ala Ile Arg
            355                 360                 365 cat gat gtt att gtg tca ata gtt aca gct gct aaa aag gat att ctt     1214
His Asp Val Ile Val Ser Ile Val Thr Ala Ala Lys Lys Asp Ile Leu
        370                 375                 380 ctg gtc aat gat cac tta ctt aat ttt gtg aga gag aga aca tta gac     1262
Leu Val Asn Asp His Leu Leu Asn Phe Val Arg Glu Arg Thr Leu Asp
385                 390                 395 aaa cga tgg aga gta cgc aaa gaa gcc atg atg gga ctt gcc caa att     1310
Lys Arg Trp Arg Val Arg Lys Glu Ala Met Met Gly Leu Ala Gln Ile
400                 405                 410                 415 tat aag aaa tat gct tta cag tca gct gct gga aaa gat gct gca aaa     1358
Tyr Lys Lys Tyr Ala Leu Gln Ser Ala Ala Gly Lys Asp Ala Ala Lys
                420                 425                 430 cag ata gca tgg atc aaa gac aaa ttg cta cat ata tat tat caa aat     1406
Gln Ile Ala Trp Ile Lys Asp Lys Leu Leu His Ile Tyr Tyr Gln Asn
            435                 440                 445 agt att gat gat cga cta ctt gtt gaa cgg atc ttt gct caa tac atg     1454
Ser Ile Asp Asp Arg Leu Leu Val Glu Arg Ile Phe Ala Gln Tyr Met
        450                 455                 460 gtt cct cac aat tta gaa act aca gaa cgg atg aaa tgc tta tat tac     1502
Val Pro His Asn Leu Glu Thr Thr Glu Arg Met Lys Cys Leu Tyr Tyr
465                 470                 475 ttg tat gcc aca ctg gat tta aat gct gtg aaa gca ttg aat gaa atg     1550
Leu Tyr Ala Thr Leu Asp Leu Asn Ala Val Lys Ala Leu Asn Glu Met
480                 485                 490                 495 tgg aaa tgt caa aat ctg ctc cga cat caa gta aag gat ttg ctt gac     1598
Trp Lys Cys Gln Asn Leu Leu Arg His Gln Val Lys Asp Leu Leu Asp
                500                 505                 510 ttg att aag caa ccc aaa aca gat gcc agt gtc aag gcc ata ttt tca     1646
```

```
Leu Ile Lys Gln Pro Lys Thr Asp Ala Ser Val Lys Ala Ile Phe Ser
        515                 520                 525 aaa gtg atg gtt att aca aga aat tta cct gat cct ggt aag gct cag      1694
Lys Val Met Val Ile Thr Arg Asn Leu Pro Asp Pro Gly Lys Ala Gln
            530                 535                 540 gat ttc atg aag aaa ttc aca cag gtg tta gaa gat gat gag aaa ata      1742
Asp Phe Met Lys Lys Phe Thr Gln Val Leu Glu Asp Asp Glu Lys Ile
        545                 550                 555 aga aag cag tta gaa gta ctt gtt agt cca aca tgc tcc tgc aag cag      1790
Arg Lys Gln Leu Glu Val Leu Val Ser Pro Thr Cys Ser Cys Lys Gln
560                 565                 570                 575 gct gaa ggt tgt gtg cgt gaa ata act aag aag ttg ggc aac ccc aaa      1838
Ala Glu Gly Cys Val Arg Glu Ile Thr Lys Lys Leu Gly Asn Pro Lys
                580                 585                 590 cag cct aca aat cct ttc ctg gaa atg atc aag ttt ctc ttg gag agg      1886
Gln Pro Thr Asn Pro Phe Leu Glu Met Ile Lys Phe Leu Leu Glu Arg
            595                 600                 605 ata gca cct gtg cac ata gat acc gaa tct atc agt gct ctt att aaa      1934
Ile Ala Pro Val His Ile Asp Thr Glu Ser Ile Ser Ala Leu Ile Lys
        610                 615                 620 caa gtg aac aaa tca ata gat gga aca gca gat gat gaa gat gag ggt      1982
Gln Val Asn Lys Ser Ile Asp Gly Thr Ala Asp Asp Glu Asp Glu Gly
625                 630                 635 gtt cca act gat caa gcc atc aga gca ggt ctt gaa ctg ctt aag gta      2030
Val Pro Thr Asp Gln Ala Ile Arg Ala Gly Leu Glu Leu Leu Lys Val
640                 645                 650                 655 ctc tca ttt aca cat ccc atc tca ttt cat tct gct gaa aca ttt gaa      2078
Leu Ser Phe Thr His Pro Ile Ser Phe His Ser Ala Glu Thr Phe Glu
                660                 665                 670 tca tta ctg gct tgt ctg aaa atg gat gat gaa aaa gta gca gaa gct      2126
Ser Leu Leu Ala Cys Leu Lys Met Asp Asp Glu Lys Val Ala Glu Ala
            675                 680                 685 gca cta caa att ttc aaa aac aca gga agc aaa att gaa gag gat ttt      2174
Ala Leu Gln Ile Phe Lys Asn Thr Gly Ser Lys Ile Glu Glu Asp Phe
        690                 695                 700 cca cac atc aga tca gcc ttg ctt cct gtt tta cat cac aaa tct aaa      2222
Pro His Ile Arg Ser Ala Leu Leu Pro Val Leu His His Lys Ser Lys
705                 710                 715 aaa gga ccc ccc cgt caa gcc aaa tat gcc att cat tgt atc cat gcg      2270
Lys Gly Pro Pro Arg Gln Ala Lys Tyr Ala Ile His Cys Ile His Ala
720                 725                 730                 735 ata ttt tct agt aaa gag acc cag ttt gca cag ata ttt gag cct ctg      2318
Ile Phe Ser Ser Lys Glu Thr Gln Phe Ala Gln Ile Phe Glu Pro Leu
                740                 745                 750 cat aag agc cta gat cca agc aac ctg gaa cat ctc ata aca cca ttg      2366
His Lys Ser Leu Asp Pro Ser Asn Leu Glu His Leu Ile Thr Pro Leu
            755                 760                 765 gtt act att ggt cat att gct ctc ctt gca cct gat caa ttt gct gct      2414
Val Thr Ile Gly His Ile Ala Leu Leu Ala Pro Asp Gln Phe Ala Ala
        770                 775                 780 cct tgg aaa tct tgg gta gct act ttc att gtg aaa gat ctc ctc atg      2462
Pro Trp Lys Ser Trp Val Ala Thr Phe Ile Val Lys Asp Leu Leu Met
785                 790                 795 aat gat cgg ctt cca ggg aaa aag aca act aaa ctt tgg gtt cca gat      2510
Asn Asp Arg Leu Pro Gly Lys Lys Thr Thr Lys Leu Trp Val Pro Asp
800                 805                 810                 815 gaa gaa gta tct cct gag aca atg gtc aaa att cag gct att aaa atg      2558
Glu Glu Val Ser Pro Glu Thr Met Val Lys Ile Gln Ala Ile Lys Met
                820                 825                 830
```

```
atg gtt cga tgg cta ctt gga atg aaa aat aat cac agt aaa tca gga        2606
Met Val Arg Trp Leu Leu Gly Met Lys Asn Asn His Ser Lys Ser Gly
        835                 840                 845 act tct acc tta aga ttg cta aca aca ata ttg cat agt gat gga gac        2654
Thr Ser Thr Leu Arg Leu Leu Thr Thr Ile Leu His Ser Asp Gly Asp
    850                 855                 860 ttg aca gaa cag ggg aaa att agt aaa cca gat atg tca cgt ctg aga        2702
Leu Thr Glu Gln Gly Lys Ile Ser Lys Pro Asp Met Ser Arg Leu Arg
865                 870                 875 ctt gct gct ggg agt gct att gtg aag ctg gca caa gaa ccc tgt tac        2750
Leu Ala Ala Gly Ser Ala Ile Val Lys Leu Ala Gln Glu Pro Cys Tyr
        880                 885                 890                 895 cat gaa atc atc aca tta gaa caa tat cag cta tgt gca tta gct atc        2798
His Glu Ile Ile Thr Leu Glu Gln Tyr Gln Leu Cys Ala Leu Ala Ile
                900                 905                 910 aac gat gaa tgc tat caa gta aga caa gtg ttt gcc cag aaa ctt cac        2846
Asn Asp Glu Cys Tyr Gln Val Arg Gln Val Phe Ala Gln Lys Leu His
            915                 920                 925 aaa ggc ctt tcc cgt tta cgg ctt cca ctt gag tat atg gca atc tgt        2894
Lys Gly Leu Ser Arg Leu Arg Leu Pro Leu Glu Tyr Met Ala Ile Cys
        930                 935                 940 gcc ctt tgt gca aaa gat cct gta aag gag aga aga gct cat gct agg        2942
Ala Leu Cys Ala Lys Asp Pro Val Lys Glu Arg Arg Ala His Ala Arg
945                 950                 955 caa tgt ttg gtg aaa aat ata aat gta agg cgg gag tat ctg aag cag        2990
Gln Cys Leu Val Lys Asn Ile Asn Val Arg Arg Glu Tyr Leu Lys Gln
960                 965                 970                 975 cat gca gct gtt agt gaa aaa tta ttg tct ctt cta cca gag tat gtt        3038
His Ala Ala Val Ser Glu Lys Leu Leu Ser Leu Leu Pro Glu Tyr Val
                980                 985                 990 gtt cca tat aca att cac ctt ttg gca cat gac cca gat tat gtc aaa        3086
Val Pro Tyr Thr Ile His Leu Leu Ala His Asp Pro Asp Tyr Val Lys
            995                 1000                1005 gta cag gat att gaa caa ctt aaa gat gtt aaa gaa tgt ctt tgg ttt        3134
Val Gln Asp Ile Glu Gln Leu Lys Asp Val Lys Glu Cys Leu Trp Phe
        1010                1015                1020 gtt ctg gaa ata tta atg gct aaa aat gaa aat aac agt cac gct ttt        3182
Val Leu Glu Ile Leu Met Ala Lys Asn Glu Asn Asn Ser His Ala Phe
1025                1030                1035 atc aga aag atg gta gaa aat att aaa caa aca aaa gat gcc caa gga        3230
Ile Arg Lys Met Val Glu Asn Ile Lys Gln Thr Lys Asp Ala Gln Gly
1040                1045                1050                1055 cca gat gat gca aaa atg aat gaa aaa ctg tac act gtg tgt gat gtt        3278
Pro Asp Asp Ala Lys Met Asn Glu Lys Leu Tyr Thr Val Cys Asp Val
                1060                1065                1070 gcc atg aat atc atc atg tca aag agt act aca tac agt ttg gaa tct        3326
Ala Met Asn Ile Ile Met Ser Lys Ser Thr Thr Tyr Ser Leu Glu Ser
            1075                1080                1085 cct aaa gac ccg gta cta cca gct cgt ttc ttc act caa cct gac aag        3374
Pro Lys Asp Pro Val Leu Pro Ala Arg Phe Phe Thr Gln Pro Asp Lys
        1090                1095                1100 aat ttc agt aac acc aaa aat tat ctg cct cct gaa atg aaa tca ttt        3422
Asn Phe Ser Asn Thr Lys Asn Tyr Leu Pro Pro Glu Met Lys Ser Phe
1105                1110                1115 ttc act cct gga aaa cct aaa aca acc aat gtt cta gga gct gtt aac        3470
Phe Thr Pro Gly Lys Pro Lys Thr Thr Asn Val Leu Gly Ala Val Asn
1120                1125                1130                1135 aag cca ctt tca tca gca ggc aag caa tct cag acc aaa tca tca cga        3518
Lys Pro Leu Ser Ser Ala Gly Lys Gln Ser Gln Thr Lys Ser Ser Arg
                1140                1145                1150
```

```
                                                              -continued atg gaa act gta agc aat gca agc agc agc tca aat cca agc tct cct      3566
Met Glu Thr Val Ser Asn Ala Ser Ser Ser Ser Asn Pro Ser Ser Pro
        1155                1160                1165 gga aga ata aag ggg agg ctt gat agt tct gaa atg gat cac agt gaa      3614
Gly Arg Ile Lys Gly Arg Leu Asp Ser Ser Glu Met Asp His Ser Glu
    1170                1175                1180 aat gaa gat tac aca atg tct tca cct ttg ccg ggg aaa aaa agt gac      3662
Asn Glu Asp Tyr Thr Met Ser Ser Pro Leu Pro Gly Lys Lys Ser Asp
1185                1190                1195 aag aga gac gac tct gat ctt gta agg tct gaa ttg gag aag cct aga      3710
Lys Arg Asp Asp Ser Asp Leu Val Arg Ser Glu Leu Glu Lys Pro Arg
1200                1205                1210                1215 ggc agg aaa aaa acg ccc gtc aca gaa cag gag gag aaa tta ggt atg      3758
Gly Arg Lys Lys Thr Pro Val Thr Glu Gln Glu Glu Lys Leu Gly Met
            1220                1225                1230 gat gac ttg act aag ttg gta cag gaa cag aaa cct aaa ggc agt cag      3806
Asp Asp Leu Thr Lys Leu Val Gln Glu Gln Lys Pro Lys Gly Ser Gln
        1235                1240                1245 cga agt cgg aaa aga ggc cat acg gct tca gaa tct gat gaa cag cag      3854
Arg Ser Arg Lys Arg Gly His Thr Ala Ser Glu Ser Asp Glu Gln Gln
    1250                1255                1260 tgg cct gag gaa aag agg ctc aaa gaa gat ata tta gaa aat gaa gat      3902
Trp Pro Glu Glu Lys Arg Leu Lys Glu Asp Ile Leu Glu Asn Glu Asp
1265                1270                1275 gaa cag aat agt ccg cca aaa aag ggt aaa aga ggc cga cca cca aaa      3950
Glu Gln Asn Ser Pro Pro Lys Lys Gly Lys Arg Gly Arg Pro Pro Lys
1280                1285                1290                1295 cct ctt ggt gga ggt aca cca aaa gaa gag cca aca atg aaa act tct      3998
Pro Leu Gly Gly Gly Thr Pro Lys Glu Glu Pro Thr Met Lys Thr Ser
            1300                1305                1310 aaa aaa gga agc aaa aaa aaa tct gga cct cca gca cca gag gag gag      4046
Lys Lys Gly Ser Lys Lys Lys Ser Gly Pro Pro Ala Pro Glu Glu Glu
        1315                1320                1325 gaa gaa gaa gaa aga caa agt gga aat acg gaa cag aag tcc aaa agc      4094
Glu Glu Glu Glu Arg Gln Ser Gly Asn Thr Glu Gln Lys Ser Lys Ser
    1330                1335                1340 aaa cag cac cga gtg tca agg aga gca cag cag aga gca gaa tct cct      4142
Lys Gln His Arg Val Ser Arg Arg Ala Gln Gln Arg Ala Glu Ser Pro
1345                1350                1355 gaa tct agt gca att gaa tcc aca cag tcc aca cca cag aaa gga cga      4190
Glu Ser Ser Ala Ile Glu Ser Thr Gln Ser Thr Pro Gln Lys Gly Arg
1360                1365                1370                1375 gga aga cca tca aaa acg cca tca cca tca caa cca aaa aaa aat gtg      4238
Gly Arg Pro Ser Lys Thr Pro Ser Pro Ser Gln Pro Lys Lys Asn Val
            1380                1385                1390 taagttgtaa atattacatt tcaaaccaat ttcaaattat tttgcaaaag ttcctaaatt    4298
tgtaaacata catattgctg tatttaaatt ccatatattt agccccatta cactaggtac    4358
ggcggcgaag tgctaaaagg gaacggcgat gaacaaatgt aattaataac tttctctgtg    4418
aaagctttgg aaaatctttt tttttttttt tttttttttg gtcaagcttg aggctgaata    4478
aagcctttga tgcacaaaat gggactgctg aagagtggac agttggacct tactttggtg    4538
accccataca tttgtggtca catgctttag ccatacacat ggtaacattg actatggagt    4598
cttgtgaaag tgtaatgtgc gatggctatg tagacataaa gaagaaactt gtaaatatct    4658
tttttctttt tttaatgtt tctgatttct gaagtgcttg tatagctttt atctgcggct     4718
ttaaactgac agtacccgac tgtttattgg atctattgat ttgaaaagaa tttgttagga    4778
```

-continued

```
tagatcttaa gcagtaatct gtcagtgttt gtatttgtat tttctgcaat tttactgtga    4838
aaaaaaattt gttttcaaca attggtgtca ttttcttgat gtcactattt gttggagagt    4898
taaatggtct cttcccttg tgtatcttac ctagtgttta ctcctgggca cccttaatct     4958
tcagaggtgc taaattgtct gccattacac cagaaggatg cctctgatag gaggacaacc    5018
atgcaaattg tgaaatagtc ctgaagttct tggattactt tacacctcag tattgatttg    5078
tcccagaatt ttctggcctt tcatggcaat gaaaatttta agaagaaaga tttaaagtat    5138
tttaatttta aagagtgtgt tataaaataa tgtactgaat tctttatccc attttatcat    5198
cctttcagtt tttattaatc tactgtatca ataaaattct gtaatttgaa tgagtaaaaa    5258
aaaaaaaaaa aaa                                                      5271
```

<210> SEQ ID NO 2
<211> LENGTH: 1391
<212> TYPE: PRT
<213> ORGANISM: Homo sapiens

<400> SEQUENCE: 2

```
Met Ala His Ser Lys Thr Arg Thr Asn Asp Gly Lys Ile Thr Tyr Pro
 1               5                  10                  15

Pro Gly Val Lys Glu Ile Ser Asp Lys Ile Ser Lys Glu Glu Met Val
            20                  25                  30

Arg Arg Leu Lys Met Val Val Lys Thr Phe Met Asp Met Asp Gln Asp
        35                  40                  45

Ser Glu Glu Lys Glu Leu Tyr Leu Asn Leu Ala Leu His Leu Ala
    50                  55                  60

Ser Asp Phe Phe Leu Lys His Pro Gly Lys Asp Val Arg Leu Leu Val
65                  70                  75                  80

Ala Cys Cys Leu Ala Asp Ile Phe Arg Ile Tyr Ala Pro Glu Ala Pro
                85                  90                  95

Tyr Thr Ser Pro Asp Lys Leu Lys Asp Ile Phe Met Phe Ile Thr Arg
            100                 105                 110

Gln Leu Lys Gly Leu Glu Asp Thr Lys Ser Pro Gln Phe Asn Arg Tyr
        115                 120                 125

Phe Tyr Leu Leu Glu Asn Ile Ala Trp Val Lys Ser Tyr Asn Ile Cys
    130                 135                 140

Phe Glu Leu Glu Asp Ser Asn Glu Ile Phe Thr Gln Leu Tyr Arg Thr
145                 150                 155                 160

Leu Phe Ser Val Ile Asn Asn Gly His Asn Gln Lys Val His Met His
                165                 170                 175

Met Val Asp Leu Met Ser Ser Ile Ile Cys Glu Gly Asp Thr Val Ser
            180                 185                 190

Gln Glu Leu Leu Asp Thr Val Leu Val Asn Leu Val Pro Ala His Lys
        195                 200                 205

Asn Leu Asn Lys Gln Ala Tyr Asp Leu Ala Lys Ala Leu Leu Lys Arg
    210                 215                 220

Thr Ala Gln Ala Ile Glu Pro Tyr Ile Thr Thr Phe Phe Asn Gln Val
225                 230                 235                 240

Leu Met Leu Gly Lys Thr Ser Ile Ser Asp Leu Ser Glu His Val Phe
                245                 250                 255

Asp Leu Ile Leu Glu Leu Tyr Asn Ile Asp Ser His Leu Leu Leu Ser
            260                 265                 270

Val Leu Pro Gln Leu Glu Phe Lys Leu Lys Ser Asn Asp Asn Glu Glu
        275                 280                 285
```

```
Arg Leu Gln Val Val Lys Leu Leu Ala Lys Met Phe Gly Ala Lys Asp
    290                 295                 300

Ser Glu Leu Ala Ser Gln Asn Lys Pro Leu Trp Gln Cys Tyr Leu Gly
305                 310                 315                 320

Arg Phe Asn Asp Ile His Val Pro Ile Arg Leu Glu Cys Val Lys Phe
                325                 330                 335

Ala Ser His Cys Leu Met Asn His Pro Asp Leu Ala Lys Asp Leu Thr
            340                 345                 350

Glu Tyr Leu Lys Val Arg Ser His Asp Pro Glu Glu Ala Ile Arg His
        355                 360                 365

Asp Val Ile Val Ser Ile Val Thr Ala Ala Lys Lys Asp Ile Leu Leu
    370                 375                 380

Val Asn Asp His Leu Leu Asn Phe Val Arg Glu Arg Thr Leu Asp Lys
385                 390                 395                 400

Arg Trp Arg Val Arg Lys Glu Ala Met Met Gly Leu Ala Gln Ile Tyr
                405                 410                 415

Lys Lys Tyr Ala Leu Gln Ser Ala Ala Gly Lys Asp Ala Ala Lys Gln
            420                 425                 430

Ile Ala Trp Ile Lys Asp Lys Leu Leu His Ile Tyr Tyr Gln Asn Ser
        435                 440                 445

Ile Asp Asp Arg Leu Leu Val Glu Arg Ile Phe Ala Gln Tyr Met Val
    450                 455                 460

Pro His Asn Leu Glu Thr Thr Glu Arg Met Lys Cys Leu Tyr Tyr Leu
465                 470                 475                 480

Tyr Ala Thr Leu Asp Leu Asn Ala Val Lys Ala Leu Asn Glu Met Trp
                485                 490                 495

Lys Cys Gln Asn Leu Leu Arg His Gln Val Lys Asp Leu Leu Asp Leu
            500                 505                 510

Ile Lys Gln Pro Lys Thr Asp Ala Ser Val Lys Ala Ile Phe Ser Lys
        515                 520                 525

Val Met Val Ile Thr Arg Asn Leu Pro Asp Pro Gly Lys Ala Gln Asp
    530                 535                 540

Phe Met Lys Lys Phe Thr Gln Val Leu Glu Asp Asp Glu Lys Ile Arg
545                 550                 555                 560

Lys Gln Leu Glu Val Leu Val Ser Pro Thr Cys Ser Cys Lys Gln Ala
                565                 570                 575

Glu Gly Cys Val Arg Glu Ile Thr Lys Lys Leu Gly Asn Pro Lys Gln
            580                 585                 590

Pro Thr Asn Pro Phe Leu Glu Met Ile Lys Phe Leu Leu Glu Arg Ile
        595                 600                 605

Ala Pro Val His Ile Asp Thr Glu Ser Ile Ser Ala Leu Ile Lys Gln
    610                 615                 620

Val Asn Lys Ser Ile Asp Gly Thr Ala Asp Asp Glu Asp Glu Gly Val
625                 630                 635                 640

Pro Thr Asp Gln Ala Ile Arg Ala Gly Leu Glu Leu Leu Lys Val Leu
                645                 650                 655

Ser Phe Thr His Pro Ile Ser Phe His Ser Ala Glu Thr Phe Glu Ser
            660                 665                 670

Leu Leu Ala Cys Leu Lys Met Asp Asp Glu Lys Val Ala Glu Ala Ala
        675                 680                 685

Leu Gln Ile Phe Lys Asn Thr Gly Ser Lys Ile Glu Glu Asp Phe Pro
    690                 695                 700
```

-continued

His Ile Arg Ser Ala Leu Leu Pro Val Leu His His Lys Ser Lys Lys
705                 710                 715                 720

Gly Pro Pro Arg Gln Ala Lys Tyr Ala Ile His Cys Ile His Ala Ile
                725                 730                 735

Phe Ser Ser Lys Glu Thr Gln Phe Ala Gln Ile Phe Glu Pro Leu His
            740                 745                 750

Lys Ser Leu Asp Pro Ser Asn Leu Glu His Leu Ile Thr Pro Leu Val
        755                 760                 765

Thr Ile Gly His Ile Ala Leu Leu Ala Pro Asp Gln Phe Ala Ala Pro
770                 775                 780

Trp Lys Ser Trp Val Ala Thr Phe Ile Val Lys Asp Leu Leu Met Asn
785                 790                 795                 800

Asp Arg Leu Pro Gly Lys Lys Thr Thr Lys Leu Trp Val Pro Asp Glu
                805                 810                 815

Glu Val Ser Pro Glu Thr Met Val Lys Ile Gln Ala Ile Lys Met Met
                820                 825                 830

Val Arg Trp Leu Leu Gly Met Lys Asn Asn His Ser Lys Ser Gly Thr
            835                 840                 845

Ser Thr Leu Arg Leu Leu Thr Thr Ile Leu His Ser Asp Gly Asp Leu
        850                 855                 860

Thr Glu Gln Gly Lys Ile Ser Lys Pro Asp Met Ser Arg Leu Arg Leu
865                 870                 875                 880

Ala Ala Gly Ser Ala Ile Val Lys Leu Ala Gln Glu Pro Cys Tyr His
                885                 890                 895

Glu Ile Ile Thr Leu Glu Gln Tyr Gln Leu Cys Ala Leu Ala Ile Asn
                900                 905                 910

Asp Glu Cys Tyr Gln Val Arg Gln Val Phe Ala Gln Lys Leu His Lys
            915                 920                 925

Gly Leu Ser Arg Leu Arg Leu Pro Leu Glu Tyr Met Ala Ile Cys Ala
        930                 935                 940

Leu Cys Ala Lys Asp Pro Val Lys Glu Arg Arg Ala His Ala Arg Gln
945                 950                 955                 960

Cys Leu Val Lys Asn Ile Asn Val Arg Arg Glu Tyr Leu Lys Gln His
                965                 970                 975

Ala Ala Val Ser Glu Lys Leu Leu Ser Leu Pro Glu Tyr Val Val
            980                 985                 990

Pro Tyr Thr Ile His Leu Leu Ala His Asp Pro Asp Tyr Val Lys Val
        995                 1000                1005

Gln Asp Ile Glu Gln Leu Lys Asp Val Lys Glu Cys Leu Trp Phe Val
1010                1015                1020

Leu Glu Ile Leu Met Ala Lys Asn Glu Asn Asn Ser His Ala Phe Ile
1025                1030                1035                1040

Arg Lys Met Val Glu Asn Ile Lys Gln Thr Lys Asp Ala Gln Gly Pro
                1045                1050                1055

Asp Asp Ala Lys Met Asn Glu Lys Leu Tyr Thr Val Cys Asp Val Ala
            1060                1065                1070

Met Asn Ile Ile Met Ser Lys Ser Thr Thr Tyr Ser Leu Glu Ser Pro
        1075                1080                1085

Lys Asp Pro Val Leu Pro Ala Arg Phe Phe Thr Gln Pro Asp Lys Asn
        1090                1095                1100

Phe Ser Asn Thr Lys Asn Tyr Leu Pro Pro Glu Met Lys Ser Phe Phe
1105                1110                1115                1120

Thr Pro Gly Lys Pro Lys Thr Thr Asn Val Leu Gly Ala Val Asn Lys

-continued

```
                    1125              1130              1135
Pro Leu Ser Ser Ala Gly Lys Gln Ser Gln Thr Lys Ser Ser Arg Met
            1140              1145              1150

Glu Thr Val Ser Asn Ala Ser Ser Ser Asn Pro Ser Ser Pro Gly
        1155              1160              1165

Arg Ile Lys Gly Arg Leu Asp Ser Ser Glu Met Asp His Ser Glu Asn
    1170              1175              1180

Glu  Asp Tyr Thr Met Ser Ser Pro Leu Pro Gly Lys Lys Ser Asp Lys
1185              1190              1195              1200

Arg Asp Asp Ser Asp Leu Val Arg Ser Glu Leu Glu Lys Pro Arg Gly
            1205              1210              1215

Arg Lys Lys Thr Pro Val Thr Glu Gln Glu Glu Lys Leu Gly Met Asp
        1220              1225              1230

Asp Leu Thr Lys Leu Val Gln Glu Gln Lys Pro Lys Gly Ser Gln Arg
        1235              1240              1245

Ser Arg Lys Arg Gly His Thr Ala Ser Glu Ser Asp Glu Gln Gln Trp
    1250              1255              1260

Pro  Glu Glu Lys Arg Leu Lys Glu Asp Ile Leu Glu Asn Glu Asp Glu
1265              1270              1275              1280

Gln Asn Ser Pro Pro Lys Lys Gly Lys Arg Gly Arg Pro Pro Lys Pro
            1285              1290              1295

Leu Gly Gly Gly Thr Pro Lys Glu Glu Pro Thr Met Lys Thr Ser Lys
            1300              1305              1310

Lys Gly Ser Lys Lys Ser Gly Pro Pro Ala Pro Glu Glu Glu
        1315              1320              1325

Glu Glu Glu Arg Gln Ser Gly Asn Thr Glu Gln Lys Ser Lys Ser Lys
    1330              1335              1340

Gln  His Arg Val Ser Arg Arg Ala Gln Gln Arg Ala Glu Ser Pro Glu
1345              1350              1355              1360

Ser Ser Ala Ile Glu Ser Thr Gln Ser Thr Pro Gln Lys Gly Arg Gly
            1365              1370              1375

Arg Pro Ser Lys Thr Pro Ser Pro Ser Gln Pro Lys Lys Asn Val
            1380              1385              1390

<210> SEQ ID NO 3
<211> LENGTH: 4173
<212> TYPE: DNA
<213> ORGANISM: Homo sapiens
<220> FEATURE:
<221> NAME/KEY: CDS
<222> LOCATION: (1)..(4173)

<400> SEQUENCE: 3 atg gct cat tca aag act agg acc aat gat gga aaa att aca tat ccg      48
Met Ala His Ser Lys Thr Arg Thr Asn Asp Gly Lys Ile Thr Tyr Pro
  1               5                  10                  15 cct ggg gtc aag gaa ata tca gat aaa ata tct aaa gag gag atg gtg      96
Pro Gly Val Lys Glu Ile Ser Asp Lys Ile Ser Lys Glu Glu Met Val
             20                  25                  30 aga cga tta aag atg gtt gtg aaa act ttt atg gat atg gac cag gac     144
Arg Arg Leu Lys Met Val Val Lys Thr Phe Met Asp Met Asp Gln Asp
         35                  40                  45 tct gaa gaa gaa aag gag ctt tat tta aac cta gct tta cat ctt gct     192
Ser Glu Glu Glu Lys Glu Leu Tyr Leu Asn Leu Ala Leu His Leu Ala
     50                  55                  60 tca gat ttt ttt ctc aag cat cct ggt aaa gat gtt cgc tta ctg gta     240
Ser Asp Phe Phe Leu Lys His Pro Gly Lys Asp Val Arg Leu Leu Val
 65                  70                  75                  80
```

```
                65                      70                      75                      80
gcc tgc tgc ctt gct gat att ttc agg att tat gct cct gaa gct cct           288
Ala Cys Cys Leu Ala Asp Ile Phe Arg Ile Tyr Ala Pro Glu Ala Pro
                    85                      90                      95 tac aca tcc cct gat aaa cta aag gat ata ttt atg ttt ata aca aga           336
Tyr Thr Ser Pro Asp Lys Leu Lys Asp Ile Phe Met Phe Ile Thr Arg
                100                     105                     110 cag ttg aag ggg cta gag gat aca aag agc cca caa ttc aat agg tat           384
Gln Leu Lys Gly Leu Glu Asp Thr Lys Ser Pro Gln Phe Asn Arg Tyr
                115                     120                     125 ttt tat tta ctt gag aac att gct tgg gtc aag tca tat aac ata tgc           432
Phe Tyr Leu Leu Glu Asn Ile Ala Trp Val Lys Ser Tyr Asn Ile Cys
            130                     135                     140 ttt gag tta gaa gat agc aat gaa att ttc acc cag cta tac aga acc           480
Phe Glu Leu Glu Asp Ser Asn Glu Ile Phe Thr Gln Leu Tyr Arg Thr
145                     150                     155                     160 tta ttt tca gtt ata aac aat ggc cac aat cag aaa gtc cat atg cac           528
Leu Phe Ser Val Ile Asn Asn Gly His Asn Gln Lys Val His Met His
                    165                     170                     175 atg gta gac ctt atg agc tct att att tgt gaa ggt gat aca gtg tct           576
Met Val Asp Leu Met Ser Ser Ile Ile Cys Glu Gly Asp Thr Val Ser
                180                     185                     190 cag gag ctt ttg gat acg gtt tta gta aat ctg gta cct gct cat aag           624
Gln Glu Leu Leu Asp Thr Val Leu Val Asn Leu Val Pro Ala His Lys
                195                     200                     205 aat tta aac aag caa gca tat gat ttg gca aag gct tta ctg aag agg           672
Asn Leu Asn Lys Gln Ala Tyr Asp Leu Ala Lys Ala Leu Leu Lys Arg
            210                     215                     220 aca gct caa gct att gag cca tat att acc act ttt ttt aat cag gtt           720
Thr Ala Gln Ala Ile Glu Pro Tyr Ile Thr Thr Phe Phe Asn Gln Val
225                     230                     235                     240 ctg atg ctt ggg aaa aca tct atc agc gat ttg tca gag cat gtc ttt           768
Leu Met Leu Gly Lys Thr Ser Ile Ser Asp Leu Ser Glu His Val Phe
                    245                     250                     255 gac tta att ttg gag ctc tac aat att gat agt cat ttg ctg ctc tct           816
Asp Leu Ile Leu Glu Leu Tyr Asn Ile Asp Ser His Leu Leu Leu Ser
                260                     265                     270 gtt tta ccc cag ctt gaa ttt aaa tta aag agc aat gat aat gag gag           864
Val Leu Pro Gln Leu Glu Phe Lys Leu Lys Ser Asn Asp Asn Glu Glu
                275                     280                     285 cgc cta caa gtt gtt aaa cta ctg gca aaa atg ttt ggg gca aag gat           912
Arg Leu Gln Val Val Lys Leu Leu Ala Lys Met Phe Gly Ala Lys Asp
            290                     295                     300 tca gaa ttg gct tct caa aac aag cca ctt tgg cag tgc tac ttg ggc           960
Ser Glu Leu Ala Ser Gln Asn Lys Pro Leu Trp Gln Cys Tyr Leu Gly
305                     310                     315                     320 agg ttt aat gat atc cat gta cca atc cgc ctg gaa tgt gtg aaa ttt          1008
Arg Phe Asn Asp Ile His Val Pro Ile Arg Leu Glu Cys Val Lys Phe
                    325                     330                     335 gct agc cat tgt ctc atg aac cat cct gat tta gca aaa gac tta aca          1056
Ala Ser His Cys Leu Met Asn His Pro Asp Leu Ala Lys Asp Leu Thr
                340                     345                     350 gag tat ctt aaa gtg agg tca cat gac cct gag gaa gct att aga cat          1104
Glu Tyr Leu Lys Val Arg Ser His Asp Pro Glu Glu Ala Ile Arg His
                355                     360                     365 gat gtt att gtg tca ata gtt aca gct gct aaa aag gat att ctt ctg          1152
Asp Val Ile Val Ser Ile Val Thr Ala Ala Lys Lys Asp Ile Leu Leu
            370                     375                     380 gtc aat gat cac tta ctt aat ttt gtg aga gag aga aca tta gac aaa          1200
```

```
                Val Asn Asp His Leu Leu Asn Phe Val Arg Glu Arg Thr Leu Asp Lys
                385                 390                 395                 400 cga tgg aga gta cgc aaa gaa gcc atg atg gga ctt gcc caa att tat        1248
Arg Trp Arg Val Arg Lys Glu Ala Met Met Gly Leu Ala Gln Ile Tyr
                405                 410                 415 aag aaa tat gct tta cag tca gca gct gga aaa gat gct gca aaa cag        1296
Lys Lys Tyr Ala Leu Gln Ser Ala Ala Gly Lys Asp Ala Ala Lys Gln
                420                 425                 430 ata gca tgg atc aaa gac aaa ttg cta cat ata tat caa aat agt            1344
Ile Ala Trp Ile Lys Asp Lys Leu Leu His Ile Tyr Tyr Gln Asn Ser
                435                 440                 445 att gat gat cga cta ctt gtt gaa cgg atc ttt gct caa tac atg gtt        1392
Ile Asp Asp Arg Leu Leu Val Glu Arg Ile Phe Ala Gln Tyr Met Val
            450                 455                 460 cct cac aat tta gaa act aca gaa cgg atg aaa tgc tta tat tac ttg        1440
Pro His Asn Leu Glu Thr Thr Glu Arg Met Lys Cys Leu Tyr Tyr Leu
465                 470                 475                 480 tat gcc aca ctg gat tta aat gct gtg aaa gca ttg aat gaa atg tgg        1488
Tyr Ala Thr Leu Asp Leu Asn Ala Val Lys Ala Leu Asn Glu Met Trp
                    485                 490                 495 aaa tgt caa aat ctg ctc cga cat caa gta aag gat ttg ctt gac ttg        1536
Lys Cys Gln Asn Leu Leu Arg His Gln Val Lys Asp Leu Leu Asp Leu
                500                 505                 510 att aag caa ccc aaa aca gat gcc agt gtc aag gcc ata ttt tca aaa        1584
Ile Lys Gln Pro Lys Thr Asp Ala Ser Val Lys Ala Ile Phe Ser Lys
            515                 520                 525 gtg atg gtt att aca aga aat tta cct gat cct ggt aag gct cag gat        1632
Val Met Val Ile Thr Arg Asn Leu Pro Asp Pro Gly Lys Ala Gln Asp
530                 535                 540 ttc atg aag aaa ttc aca cag gtg tta gaa gat gat gag aaa ata aga        1680
Phe Met Lys Lys Phe Thr Gln Val Leu Glu Asp Asp Glu Lys Ile Arg
545                 550                 555                 560 aag cag tta gaa gta ctt gtt agt cca aca tgc tcc tgc aag cag gct        1728
Lys Gln Leu Glu Val Leu Val Ser Pro Thr Cys Ser Cys Lys Gln Ala
                565                 570                 575 gaa ggt tgt gtg cgt gaa ata act aag aag ttg ggc aac ccc aaa cag        1776
Glu Gly Cys Val Arg Glu Ile Thr Lys Lys Leu Gly Asn Pro Lys Gln
                580                 585                 590 cct aca aat cct ttc ctg gaa atg atc aag ttt ctc ttg gag agg ata        1824
Pro Thr Asn Pro Phe Leu Glu Met Ile Lys Phe Leu Leu Glu Arg Ile
                595                 600                 605 gca cct gtg cac ata gat acc gaa tct atc agt gct ctt att aaa caa        1872
Ala Pro Val His Ile Asp Thr Glu Ser Ile Ser Ala Leu Ile Lys Gln
            610                 615                 620 gtg aac aaa tca ata gat gga aca gca gat gat gaa gat gag ggt gtt        1920
Val Asn Lys Ser Ile Asp Gly Thr Ala Asp Asp Glu Asp Glu Gly Val
625                 630                 635                 640 cca act gat caa gcc atc aga gca ggt ctt gaa ctg ctt aag gta ctc        1968
Pro Thr Asp Gln Ala Ile Arg Ala Gly Leu Glu Leu Leu Lys Val Leu
                645                 650                 655 tca ttt aca cat ccc atc tca ttt cat tct gct gaa aca ttt gaa tca        2016
Ser Phe Thr His Pro Ile Ser Phe His Ser Ala Glu Thr Phe Glu Ser
                660                 665                 670 tta ctg gct tgt ctg aaa atg gat gat gaa aaa gta gca gaa gct gca        2064
Leu Leu Ala Cys Leu Lys Met Asp Asp Glu Lys Val Ala Glu Ala Ala
                675                 680                 685 cta caa att ttc aaa aac aca gga agc aaa att gaa gag gat ttt cca        2112
Leu Gln Ile Phe Lys Asn Thr Gly Ser Lys Ile Glu Glu Asp Phe Pro
            690                 695                 700
```

-continued

```
cac atc aga tca gcc ttg ctt cct gtt tta cat cac aaa tct aaa aaa    2160
His Ile Arg Ser Ala Leu Leu Pro Val Leu His His Lys Ser Lys Lys
705                 710                 715                 720 gga ccc ccc cgt caa gcc aaa tat gcc att cat tgt atc cat gcg ata    2208
Gly Pro Pro Arg Gln Ala Lys Tyr Ala Ile His Cys Ile His Ala Ile
                725                 730                 735 ttt tct agt aaa gag acc cag ttt gca cag ata ttt gag cct ctg cat    2256
Phe Ser Ser Lys Glu Thr Gln Phe Ala Gln Ile Phe Glu Pro Leu His
            740                 745                 750 aag agc cta gat cca agc aac ctg gaa cat ctc ata aca cca ttg gtt    2304
Lys Ser Leu Asp Pro Ser Asn Leu Glu His Leu Ile Thr Pro Leu Val
        755                 760                 765 act att ggt cat att gct ctc ctt gca cct gat caa ttt gct gct cct    2352
Thr Ile Gly His Ile Ala Leu Leu Ala Pro Asp Gln Phe Ala Ala Pro
    770                 775                 780 tgg aaa tct tgg gta gct act ttc att gtg aaa gat ctt ctc atg aat    2400
Trp Lys Ser Trp Val Ala Thr Phe Ile Val Lys Asp Leu Leu Met Asn
785                 790                 795                 800 gat cgg ctt cca ggg aaa aag aca act aaa ctt tgg gtt cca gat gaa    2448
Asp Arg Leu Pro Gly Lys Lys Thr Thr Lys Leu Trp Val Pro Asp Glu
                805                 810                 815 gaa gta tct cct gag aca atg gtc aaa att cag gct att aaa atg atg    2496
Glu Val Ser Pro Glu Thr Met Val Lys Ile Gln Ala Ile Lys Met Met
            820                 825                 830 gtt cga tgg cta ctt gga atg aaa aat aat cac agt aaa tca gga act    2544
Val Arg Trp Leu Leu Gly Met Lys Asn Asn His Ser Lys Ser Gly Thr
        835                 840                 845 tct acc tta aga ttg cta aca aca ata ttg cat agt gat gga gac ttg    2592
Ser Thr Leu Arg Leu Leu Thr Thr Ile Leu His Ser Asp Gly Asp Leu
    850                 855                 860 aca gaa cag ggg aaa att agt aaa cca gat atg tca cgt ctg aga ctt    2640
Thr Glu Gln Gly Lys Ile Ser Lys Pro Asp Met Ser Arg Leu Arg Leu
865                 870                 875                 880 gct gct ggg agt gct att gtg aag ctg gca caa gaa ccc tgt tac cat    2688
Ala Ala Gly Ser Ala Ile Val Lys Leu Ala Gln Glu Pro Cys Tyr His
                885                 890                 895 gaa atc atc aca tta gaa caa tat cag cta tgt gca tta gct atc aac    2736
Glu Ile Ile Thr Leu Glu Gln Tyr Gln Leu Cys Ala Leu Ala Ile Asn
            900                 905                 910 gat gaa tgc tat caa gta aga caa gtg ttt gcc cag aaa ctt cac aaa    2784
Asp Glu Cys Tyr Gln Val Arg Gln Val Phe Ala Gln Lys Leu His Lys
        915                 920                 925 ggc ctt tcc cgt tta cgg ctt cca ctt gag tat atg gca atc tgt gcc    2832
Gly Leu Ser Arg Leu Arg Leu Pro Leu Glu Tyr Met Ala Ile Cys Ala
    930                 935                 940 ctt tgt gca aaa gat cct gta aag gag aga aga gct cat gct agg caa    2880
Leu Cys Ala Lys Asp Pro Val Lys Glu Arg Arg Ala His Ala Arg Gln
945                 950                 955                 960 tgt ttg gtg aaa aat ata aat gta agg cgg gag tat ctg aag cag cat    2928
Cys Leu Val Lys Asn Ile Asn Val Arg Arg Glu Tyr Leu Lys Gln His
                965                 970                 975 gca gct gtt agt gaa aaa tta ttg tct ctt cta cca gag tat gtt gtt    2976
Ala Ala Val Ser Glu Lys Leu Leu Ser Leu Leu Pro Glu Tyr Val Val
            980                 985                 990 cca tat aca att cac ctt ttg gca cat gac cca gat tat gtc aaa gta    3024
Pro Tyr Thr Ile His Leu Leu Ala His Asp Pro Asp Tyr Val Lys Val
        995                 1000                1005 cag gat att gaa caa ctt aaa gat gtt aaa gaa tgt ctt tgg ttt gtt    3072
Gln Asp Ile Glu Gln Leu Lys Asp Val Lys Glu Cys Leu Trp Phe Val
    1010                1015                1020
```

```
ctg gaa ata tta atg gct aaa aat gaa aat aac agt cac gct ttt atc      3120
Leu Glu Ile Leu Met Ala Lys Asn Glu Asn Asn Ser His Ala Phe Ile
1025                1030                1035                1040 aga aag atg gta gaa aat att aaa caa aca aaa gat gcc caa gga cca      3168
Arg Lys Met Val Glu Asn Ile Lys Gln Thr Lys Asp Ala Gln Gly Pro
            1045                1050                1055 gat gat gca aaa atg aat gaa aaa ctg tac act gtg tgt gat gtt gcc      3216
Asp Asp Ala Lys Met Asn Glu Lys Leu Tyr Thr Val Cys Asp Val Ala
        1060                1065                1070 atg aat atc atc atg tca aag agt act aca tac agt ttg gaa tct cct      3264
Met Asn Ile Ile Met Ser Lys Ser Thr Thr Tyr Ser Leu Glu Ser Pro
    1075                1080                1085 aaa gac ccg gta cta cca gct cgt ttc ttc act caa cct gac aag aat      3312
Lys Asp Pro Val Leu Pro Ala Arg Phe Phe Thr Gln Pro Asp Lys Asn
1090                1095                1100 ttc agt aac acc aaa aat tat ctg cct cct gaa atg aaa tca ttt ttc      3360
Phe Ser Asn Thr Lys Asn Tyr Leu Pro Pro Glu Met Lys Ser Phe Phe
1105                1110                1115                1120 act cct gga aaa cct aaa aca acc aat gtt cta gga gct gtt aac aag      3408
Thr Pro Gly Lys Pro Lys Thr Thr Asn Val Leu Gly Ala Val Asn Lys
            1125                1130                1135 cca ctt tca tca gca ggc aag caa tct cag acc aaa tca tca cga atg      3456
Pro Leu Ser Ser Ala Gly Lys Gln Ser Gln Thr Lys Ser Ser Arg Met
        1140                1145                1150 gaa act gta agc aat gca agc agc agc tca aat cca agc tct cct gga      3504
Glu Thr Val Ser Asn Ala Ser Ser Ser Ser Asn Pro Ser Ser Pro Gly
    1155                1160                1165 aga ata aag ggg agg ctt gat agt tct gaa atg gat cac agt gaa aat      3552
Arg Ile Lys Gly Arg Leu Asp Ser Ser Glu Met Asp His Ser Glu Asn
1170                1175                1180 gaa gat tac aca atg tct tca cct ttg ccg ggg aaa aaa agt gac aag      3600
Glu Asp Tyr Thr Met Ser Ser Pro Leu Pro Gly Lys Lys Ser Asp Lys
1185                1190                1195                1200 aga gac gac tct gat ctt gta agg tct gaa ttg gag aag cct aga ggc      3648
Arg Asp Asp Ser Asp Leu Val Arg Ser Glu Leu Glu Lys Pro Arg Gly
            1205                1210                1215 agg aaa aaa acg ccc gtc aca gaa cag gag gag aaa tta ggt atg gat      3696
Arg Lys Lys Thr Pro Val Thr Glu Gln Glu Glu Lys Leu Gly Met Asp
        1220                1225                1230 gac ttg act aag ttg gta cag gaa cag aaa cct aaa ggc agt cag cga      3744
Asp Leu Thr Lys Leu Val Gln Glu Gln Lys Pro Lys Gly Ser Gln Arg
    1235                1240                1245 agt cgg aaa aga ggc cat acg gct tca gaa tct gat gaa cag cag tgg      3792
Ser Arg Lys Arg Gly His Thr Ala Ser Glu Ser Asp Glu Gln Gln Trp
1250                1255                1260 cct gag gaa aag agg ctc aaa gaa gat ata tta gaa aat gaa gat gaa      3840
Pro Glu Glu Lys Arg Leu Lys Glu Asp Ile Leu Glu Asn Glu Asp Glu
1265                1270                1275                1280 cag aat agt ccg cca aaa aag ggt aaa aga ggc cga cca cca aaa cct      3888
Gln Asn Ser Pro Pro Lys Lys Gly Lys Arg Gly Arg Pro Pro Lys Pro
            1285                1290                1295 ctt ggt gga ggt aca cca aaa gaa gag cca aca atg aaa act tct aaa      3936
Leu Gly Gly Gly Thr Pro Lys Glu Glu Pro Thr Met Lys Thr Ser Lys
        1300                1305                1310 aaa gga agc aaa aaa aaa tct gga cct cca gca cca gag gag gag gaa      3984
Lys Gly Ser Lys Lys Lys Ser Gly Pro Pro Ala Pro Glu Glu Glu Glu
    1315                1320                1325 gaa gaa gaa aga caa agt gga aat acg gaa cag aag tcc aaa agc aaa      4032
Glu Glu Glu Arg Gln Ser Gly Asn Thr Glu Gln Lys Ser Lys Ser Lys
```

-continued

```
                  1330                1335                1340
cag cac cga gtg tca agg aga gca cag cag aga gca gaa tct cct gaa          4080
Gln His Arg Val Ser Arg Arg Ala Gln Gln Arg Ala Glu Ser Pro Glu
1345                1350                1355                1360 tct agt gca att gaa tcc aca cag tcc aca cca cag aaa gga cga gga          4128
Ser Ser Ala Ile Glu Ser Thr Gln Ser Thr Pro Gln Lys Gly Arg Gly
                1365                1370                1375 aga cca tca aaa acg cca tca cca tca caa cca aaa aaa aat gtg              4173
Arg Pro Ser Lys Thr Pro Ser Pro Ser Gln Pro Lys Lys Asn Val
            1380                1385                1390

<210> SEQ ID NO 4
<211> LENGTH: 5355
<212> TYPE: DNA
<213> ORGANISM: Homo sapiens
<220> FEATURE:
<221> NAME/KEY: CDS
<222> LOCATION: (150)..(4322)

<400> SEQUENCE: 4
cggagaggag gaggaacggc agggctggct gcggaagggg aggggggggg agaaggcgat           60
tggatgcggc ggcggcggcg gatcccggag agccccggag tgagcggagt agcgagtcgg          120
caacccggag gggtagaaat atttctgtc atg gct cat tca aag act agg acc           173
                                Met Ala His Ser Lys Thr Arg Thr
                                  1               5 aat gat gga aaa att aca tat ccg cct ggg gtc aag gaa ata tca gat          221
Asn Asp Gly Lys Ile Thr Tyr Pro Pro Gly Val Lys Glu Ile Ser Asp
     10                  15                  20 aaa ata tct aaa gag gag atg gtg aga cga tta aag atg gtt gtg aaa          269
Lys Ile Ser Lys Glu Glu Met Val Arg Arg Leu Lys Met Val Val Lys
 25                  30                  35                  40 act ttt atg gat atg gac cag gac tct gaa gaa gaa aag gag ctt tat          317
Thr Phe Met Asp Met Asp Gln Asp Ser Glu Glu Glu Lys Glu Leu Tyr
                 45                  50                  55 tta aac cta gct tta cat ctt gct tca gat ttt ttt ctc aag cat cct          365
Leu Asn Leu Ala Leu His Leu Ala Ser Asp Phe Phe Leu Lys His Pro
             60                  65                  70 ggt aaa gat gtt cgc tta ctg gta gcc tgc tgc ctt gct gat att ttc          413
Gly Lys Asp Val Arg Leu Leu Val Ala Cys Cys Leu Ala Asp Ile Phe
         75                  80                  85 agg att tat gct cct gaa gct cct tac aca tcc cct gat aaa cta aag          461
Arg Ile Tyr Ala Pro Glu Ala Pro Tyr Thr Ser Pro Asp Lys Leu Lys
     90                  95                 100 gat ata ttt atg ttt ata aca aga cag ttg aag ggg cta gag gat aca          509
Asp Ile Phe Met Phe Ile Thr Arg Gln Leu Lys Gly Leu Glu Asp Thr
105                 110                 115                 120 aag agc cca caa ttc aat agg tat ttt tat tta ctt gag aac att gct          557
Lys Ser Pro Gln Phe Asn Arg Tyr Phe Tyr Leu Leu Glu Asn Ile Ala
                125                 130                 135 tgg gtc aag tca tat aac ata tgc ttt gag tta gaa gat agc aat gaa          605
Trp Val Lys Ser Tyr Asn Ile Cys Phe Glu Leu Glu Asp Ser Asn Glu
            140                 145                 150 att ttc acc cag cta tac aga acc tta ttt tca gtt ata aac aat ggc          653
Ile Phe Thr Gln Leu Tyr Arg Thr Leu Phe Ser Val Ile Asn Asn Gly
        155                 160                 165 cac aat cag aaa gtc cat atg cac atg gta gac ctt atg agc tct att          701
His Asn Gln Lys Val His Met His Met Val Asp Leu Met Ser Ser Ile
    170                 175                 180 att tgt gaa ggt gat aca gtg tct cag gag ctt ttg gat acg gtt tta          749
Ile Cys Glu Gly Asp Thr Val Ser Gln Glu Leu Leu Asp Thr Val Leu
```

```
                                              185                 190                 195                 200
gta aat ctg gta cct gct cat aag aat tta aac aag caa gca tat gat            797
Val Asn Leu Val Pro Ala His Lys Asn Leu Asn Lys Gln Ala Tyr Asp
                205                 210                 215 ttg gca aag gct tta ctg aag agg aca gct caa gct att gag cca tat            845
Leu Ala Lys Ala Leu Leu Lys Arg Thr Ala Gln Ala Ile Glu Pro Tyr
            220                 225                 230 att acc act ttt ttt aat cag gtt ctg atg ctt ggg aaa aca tct atc            893
Ile Thr Thr Phe Phe Asn Gln Val Leu Met Leu Gly Lys Thr Ser Ile
        235                 240                 245 agc gat ttg tca gag cat gtc ttt gac tta att ttg gag ctc tac aat            941
Ser Asp Leu Ser Glu His Val Phe Asp Leu Ile Leu Glu Leu Tyr Asn
    250                 255                 260 att gat agt cat ttg ctg ctc tct gtt tta ccc cag ctt gaa ttt aaa            989
Ile Asp Ser His Leu Leu Leu Ser Val Leu Pro Gln Leu Glu Phe Lys
265                 270                 275                 280 tta aag agc aat gat aat gag gag cgc cta caa gtt gtt aaa cta ctg           1037
Leu Lys Ser Asn Asp Asn Glu Glu Arg Leu Gln Val Val Lys Leu Leu
                285                 290                 295 gca aaa atg ttt ggg gca aag gat tca gaa ttg gct tct caa aac aag           1085
Ala Lys Met Phe Gly Ala Lys Asp Ser Glu Leu Ala Ser Gln Asn Lys
            300                 305                 310 cca ctt tgg cag tgc tac ttg ggc agg ttt aat gat atc cat gta cca           1133
Pro Leu Trp Gln Cys Tyr Leu Gly Arg Phe Asn Asp Ile His Val Pro
        315                 320                 325 atc cgc ctg gaa tgt gtg aaa ttt gct agc cat tgt ctc atg aac cat           1181
Ile Arg Leu Glu Cys Val Lys Phe Ala Ser His Cys Leu Met Asn His
    330                 335                 340 cct gat tta gca aaa gac tta aca gag tat ctt aaa gtg agg tca cat           1229
Pro Asp Leu Ala Lys Asp Leu Thr Glu Tyr Leu Lys Val Arg Ser His
345                 350                 355                 360 gac cct gag gaa gct att aga cat gat gtt att gtg tca ata gtt aca           1277
Asp Pro Glu Glu Ala Ile Arg His Asp Val Ile Val Ser Ile Val Thr
                365                 370                 375 gct gct aaa aag gat att ctt ctg gtc aat gat cac tta ctt aat ttt           1325
Ala Ala Lys Lys Asp Ile Leu Leu Val Asn Asp His Leu Leu Asn Phe
            380                 385                 390 gtg aga gag aga aca tta gac aaa cga tgg aga gta cgc aaa gaa gcc           1373
Val Arg Glu Arg Thr Leu Asp Lys Arg Trp Arg Val Arg Lys Glu Ala
        395                 400                 405 atg atg gga ctt gcc caa att tat aag aaa tat gct tta cag tca gca           1421
Met Met Gly Leu Ala Gln Ile Tyr Lys Lys Tyr Ala Leu Gln Ser Ala
    410                 415                 420 gct gga aaa gat gct gca aaa cag ata gca tgg atc aaa gac aaa ttg           1469
Ala Gly Lys Asp Ala Ala Lys Gln Ile Ala Trp Ile Lys Asp Lys Leu
425                 430                 435                 440 cta cat ata tat tat caa aat agt att gat gat cga cta ctt gtt gaa           1517
Leu His Ile Tyr Tyr Gln Asn Ser Ile Asp Asp Arg Leu Leu Val Glu
                445                 450                 455 cgg atc ttt gct caa tac atg gtt cct cac aat tta gaa act aca gaa           1565
Arg Ile Phe Ala Gln Tyr Met Val Pro His Asn Leu Glu Thr Thr Glu
            460                 465                 470 cgg atg aaa tgc tta tat tac ttg tat gcc aca ctg gat tta aat gct           1613
Arg Met Lys Cys Leu Tyr Tyr Leu Tyr Ala Thr Leu Asp Leu Asn Ala
        475                 480                 485 gtg aaa gca ttg aat gaa atg tgg aaa tgt caa aat ctg ctc cga cat           1661
Val Lys Ala Leu Asn Glu Met Trp Lys Cys Gln Asn Leu Leu Arg His
    490                 495                 500 caa gta aag gat ttg ctt gac ttg att aag caa ccc aaa aca gat gcc           1709
```

```
Gln Val Lys Asp Leu Leu Asp Leu Ile Lys Gln Pro Lys Thr Asp Ala
505                 510                 515                 520 agt gtc aag gcc ata ttt tca aaa gtg atg gtt att aca aga aat tta        1757
Ser Val Lys Ala Ile Phe Ser Lys Val Met Val Ile Thr Arg Asn Leu
                525                 530                 535 cct gat cct ggt aag gct cag gat ttc atg aag aaa ttc aca cag gtg        1805
Pro Asp Pro Gly Lys Ala Gln Asp Phe Met Lys Lys Phe Thr Gln Val
        540                 545                 550 tta gaa gat gat gag aaa ata aga aag cag tta gaa gta ctt gtt agt        1853
Leu Glu Asp Asp Glu Lys Ile Arg Lys Gln Leu Glu Val Leu Val Ser
            555                 560                 565 cca aca tgc tcc tgc aag cag gct gaa ggt tgt gtg cgt gaa ata act        1901
Pro Thr Cys Ser Cys Lys Gln Ala Glu Gly Cys Val Arg Glu Ile Thr
570                 575                 580 aag aag ttg ggc aac ccc aaa cag cct aca aat cct ttc ctg gaa atg        1949
Lys Lys Leu Gly Asn Pro Lys Gln Pro Thr Asn Pro Phe Leu Glu Met
585                 590                 595                 600 atc aag ttt ctc ttg gag agg ata gca cct gtg cac ata gat acc gaa        1997
Ile Lys Phe Leu Leu Glu Arg Ile Ala Pro Val His Ile Asp Thr Glu
                605                 610                 615 tct atc agt gct ctt att aaa caa gtg aac aaa tca ata gat gga aca        2045
Ser Ile Ser Ala Leu Ile Lys Gln Val Asn Lys Ser Ile Asp Gly Thr
                620                 625                 630 gca gat gat gaa gat gag ggt gtt cca act gat caa gcc atc aga gca        2093
Ala Asp Asp Glu Asp Glu Gly Val Pro Thr Asp Gln Ala Ile Arg Ala
            635                 640                 645 ggt ctt gaa ctg ctt aag gta ctc tca ttt aca cat ccc atc tca ttt        2141
Gly Leu Glu Leu Leu Lys Val Leu Ser Phe Thr His Pro Ile Ser Phe
650                 655                 660 cat tct gct gaa aca ttt gaa tca tta ctg gct tgt ctg aaa atg gat        2189
His Ser Ala Glu Thr Phe Glu Ser Leu Leu Ala Cys Leu Lys Met Asp
665                 670                 675                 680 gat gaa aaa gta gca gaa gct gca cta caa att ttc aaa aac aca gga        2237
Asp Glu Lys Val Ala Glu Ala Ala Leu Gln Ile Phe Lys Asn Thr Gly
                685                 690                 695 agc aaa att gaa gag gat ttt cca cac atc aga tca gcc ttg ctt cct        2285
Ser Lys Ile Glu Glu Asp Phe Pro His Ile Arg Ser Ala Leu Leu Pro
                700                 705                 710 gtt tta cat cac aaa tct aaa aaa gga ccc ccc cgt caa gcc aaa tat        2333
Val Leu His His Lys Ser Lys Lys Gly Pro Pro Arg Gln Ala Lys Tyr
            715                 720                 725 gcc att cat tgt atc cat gcg ata ttt tct agt aaa gag acc cag ttt        2381
Ala Ile His Cys Ile His Ala Ile Phe Ser Ser Lys Glu Thr Gln Phe
730                 735                 740 gca cag ata ttt gag cct ctg cat aag agc cta gat cca agc aac ctg        2429
Ala Gln Ile Phe Glu Pro Leu His Lys Ser Leu Asp Pro Ser Asn Leu
745                 750                 755                 760 gaa cat ctc ata aca cca ttg gtt act att ggt cat att gct ctc ctt        2477
Glu His Leu Ile Thr Pro Leu Val Thr Ile Gly His Ile Ala Leu Leu
                765                 770                 775 gca cct gat caa ttt gct gct cct tgg aaa tct tgg gta gct act ttc        2525
Ala Pro Asp Gln Phe Ala Ala Pro Trp Lys Ser Trp Val Ala Thr Phe
            780                 785                 790 att gtg aaa gat ctt ctc atg aat gat cgg ctt cca ggg aag aag aca        2573
Ile Val Lys Asp Leu Leu Met Asn Asp Arg Leu Pro Gly Lys Lys Thr
                795                 800                 805 act aaa ctt tgg gtt cca gat gaa gaa gta tct cct gag aca atg gtc        2621
Thr Lys Leu Trp Val Pro Asp Glu Glu Val Ser Pro Glu Thr Met Val
810                 815                 820
```

-continued

| | |
|---|---|
| aaa att cag gct att aaa atg atg gtt cga tgg cta ctt gga atg aaa<br>Lys Ile Gln Ala Ile Lys Met Met Val Arg Trp Leu Leu Gly Met Lys<br>825                    830                      835                      840 | 2669 |
| aat aat cac agt aaa tca gga act tct acc tta aga ttg cta aca aca<br>Asn Asn His Ser Lys Ser Gly Thr Ser Thr Leu Arg Leu Leu Thr Thr<br>                845                      850                      855 | 2717 |
| ata ttg cat agt gat gga gac ttg aca gaa cag ggg aaa att agt aaa<br>Ile Leu His Ser Asp Gly Asp Leu Thr Glu Gln Gly Lys Ile Ser Lys<br>                860                      865                      870 | 2765 |
| cca gat atg tca cgt ctg aga ctt gct gct ggg agt gct att gtg aag<br>Pro Asp Met Ser Arg Leu Arg Leu Ala Ala Gly Ser Ala Ile Val Lys<br>875                    880                      885 | 2813 |
| ctg gca caa gaa ccc tgt tac cat gaa atc atc aca tta gaa caa tat<br>Leu Ala Gln Glu Pro Cys Tyr His Glu Ile Ile Thr Leu Glu Gln Tyr<br>        890                      895                      900 | 2861 |
| cag cta tgt gca tta gct atc aac gat gaa tgc tat caa gta aga caa<br>Gln Leu Cys Ala Leu Ala Ile Asn Asp Glu Cys Tyr Gln Val Arg Gln<br>905                    910                      915                      920 | 2909 |
| gtg ttt gcc cag aaa ctt cac aaa ggc ctt tcc cgt tta cgg ctt cca<br>Val Phe Ala Gln Lys Leu His Lys Gly Leu Ser Arg Leu Arg Leu Pro<br>                925                      930                      935 | 2957 |
| ctt gag tat atg gca atc tgt gcc ctt tgt gca aaa gat cct gta aag<br>Leu Glu Tyr Met Ala Ile Cys Ala Leu Cys Ala Lys Asp Pro Val Lys<br>                940                      945                      950 | 3005 |
| gag aga aga gct cat gct agg caa tgt ttg gtg aaa aat ata aat gta<br>Glu Arg Arg Ala His Ala Arg Gln Cys Leu Val Lys Asn Ile Asn Val<br>                955                      960                      965 | 3053 |
| agg cgg gag tat ctg aag cag cat gca gct gtt agt gaa aaa tta ttg<br>Arg Arg Glu Tyr Leu Lys Gln His Ala Ala Val Ser Glu Lys Leu Leu<br>970                    975                      980 | 3101 |
| tct ctt cta cca gag tat gtt gtt cca tat aca att cac ctt ttg gca<br>Ser Leu Leu Pro Glu Tyr Val Val Pro Tyr Thr Ile His Leu Leu Ala<br>985                    990                      995                    1000 | 3149 |
| cat gac cca gat tat gtc aaa gta cag gat att gaa caa ctt aaa gat<br>His Asp Pro Asp Tyr Val Lys Val Gln Asp Ile Glu Gln Leu Lys Asp<br>                1005                  1010                  1015 | 3197 |
| gtt aaa gaa tgt ctt tgg ttt gtt ctg gaa ata tta atg gct aaa aat<br>Val Lys Glu Cys Leu Trp Phe Val Leu Glu Ile Leu Met Ala Lys Asn<br>1020                   1025                  1030 | 3245 |
| gaa aat aac agt cac gct ttt atc aga aag atg gta gaa aat att aaa<br>Glu Asn Asn Ser His Ala Phe Ile Arg Lys Met Val Glu Asn Ile Lys<br>                1035                  1040                  1045 | 3293 |
| caa aca aaa gat gcc caa gga cca gat gat gca aaa atg aat gaa aaa<br>Gln Thr Lys Asp Ala Gln Gly Pro Asp Asp Ala Lys Met Asn Glu Lys<br>1050                   1055                  1060 | 3341 |
| ctg tac act gtg tgt gat gtt gcc atg aat atc atc atg tca aag agt<br>Leu Tyr Thr Val Cys Asp Val Ala Met Asn Ile Ile Met Ser Lys Ser<br>1065                   1070                  1075                  1080 | 3389 |
| act aca tac agt ttg gaa tct cct aaa gac ccg gta cta cca gct cgt<br>Thr Thr Tyr Ser Leu Glu Ser Pro Lys Asp Pro Val Leu Pro Ala Arg<br>                1085                  1090                  1095 | 3437 |
| ttc ttc act caa cct gac aag aat ttc agt aac acc aaa aat tat ctg<br>Phe Phe Thr Gln Pro Asp Lys Asn Phe Ser Asn Thr Lys Asn Tyr Leu<br>1100                   1105                  1110 | 3485 |
| cct cct gaa atg aaa tca ttt ttc act cct gga aaa cct aaa aca acc<br>Pro Pro Glu Met Lys Ser Phe Phe Thr Pro Gly Lys Pro Lys Thr Thr<br>                1115                  1120                  1125 | 3533 |
| aat gtt cta gga gct gtt aac aag cca ctt tca tca gca ggc aag caa<br>Asn Val Leu Gly Ala Val Asn Lys Pro Leu Ser Ser Ala Gly Lys Gln<br>1130                   1135                  1140 | 3581 |

```
tct cag acc aaa tca tca cga atg gaa act gta agc aat gca agc agc    3629
Ser Gln Thr Lys Ser Ser Arg Met Glu Thr Val Ser Asn Ala Ser Ser
1145                1150                1155                1160 agc tca aat cca agc tct cct gga aga ata aag ggg agg ctt gat agt    3677
Ser Ser Asn Pro Ser Ser Pro Gly Arg Ile Lys Gly Arg Leu Asp Ser
            1165                1170                1175 tct gaa atg gat cac agt gaa aat gaa gat tac aca atg tct tca cct    3725
Ser Glu Met Asp His Ser Glu Asn Glu Asp Tyr Thr Met Ser Ser Pro
        1180                1185                1190 ttg ccg ggg aaa aaa agt gac aag aga gac gac tct gat ctt gta agg    3773
Leu Pro Gly Lys Lys Ser Asp Lys Arg Asp Asp Ser Asp Leu Val Arg
    1195                1200                1205 tct gaa ttg gag aag cct aga ggc agg aaa aaa acg ccc gtc aca gaa    3821
Ser Glu Leu Glu Lys Pro Arg Gly Arg Lys Lys Thr Pro Val Thr Glu
1210                1215                1220 cag gag gag aaa tta ggt atg gat gac ttg act aag ttg gta cag gaa    3869
Gln Glu Glu Lys Leu Gly Met Asp Asp Leu Thr Lys Leu Val Gln Glu
1225                1230                1235                1240 cag aaa cct aaa ggc agt cag cga agt cgg aaa aga ggc cat acg gct    3917
Gln Lys Pro Lys Gly Ser Gln Arg Ser Arg Lys Arg Gly His Thr Ala
            1245                1250                1255 tca gaa tct gat gaa cag cag tgg cct gag gaa aag agg ctc aaa gaa    3965
Ser Glu Ser Asp Glu Gln Gln Trp Pro Glu Glu Lys Arg Leu Lys Glu
        1260                1265                1270 gat ata tta gaa aat gaa gat gaa cag aat agt ccg cca aaa aag ggt    4013
Asp Ile Leu Glu Asn Glu Asp Glu Gln Asn Ser Pro Pro Lys Lys Gly
    1275                1280                1285 aaa aga ggc cga cca cca aaa cct ctt ggt gga ggt aca cca aaa gaa    4061
Lys Arg Gly Arg Pro Pro Lys Pro Leu Gly Gly Gly Thr Pro Lys Glu
1290                1295                1300 gag cca aca atg aaa act tct aaa aaa gga agc aaa aaa aaa tct gga    4109
Glu Pro Thr Met Lys Thr Ser Lys Lys Gly Ser Lys Lys Lys Ser Gly
1305                1310                1315                1320 cct cca gca cca gag gag gag gaa gaa gaa gaa aga caa agt gga aat    4157
Pro Pro Ala Pro Glu Glu Glu Glu Glu Glu Glu Arg Gln Ser Gly Asn
            1325                1330                1335 acg gaa cag aag tcc aaa agc aaa cag cac cga gtg tca agg aga gca    4205
Thr Glu Gln Lys Ser Lys Ser Lys Gln His Arg Val Ser Arg Arg Ala
        1340                1345                1350 cag cag aga gca gaa tct cct gaa tct agt gca att gaa tcc aca cag    4253
Gln Gln Arg Ala Glu Ser Pro Glu Ser Ser Ala Ile Glu Ser Thr Gln
    1355                1360                1365 tcc aca cca cag aaa gga cga gga aga cca tca aaa acg cca tca cca    4301
Ser Thr Pro Gln Lys Gly Arg Gly Arg Pro Ser Lys Thr Pro Ser Pro
1370                1375                1380 tca caa cca aaa aaa aat gtg taagttgtaa atattacatt tcaaaccaat      4352
Ser Gln Pro Lys Lys Asn Val
1385                1390 ttcaaattat tttgcaaaag ttcctaaatt tgtaaacata catattgctg tatttaaatt  4412
ccatatattt agccccatta cactaggtac ggcggcgaag tgctaaaagg gaacggcgat  4472
gaacaaatgt aattaataac tttctctgtg aaagctttgg aaaaatcttt tttttttttt  4532
tttttttttg gtcaagcttg aggctgaata aagcctttga tgcacaaaat gggactgctg  4592
aagagtggac agttggacct tactttggtg accccataca tttgtggtca catgctttag  4652
ccatacacat ggtaacattg actatggagt cttgtgaaag tgtaatgtgc gatggctatg  4712
tagacataaa gaagaaactt gtaaatatct tttttctttt ttttaatgtt tctgatttct  4772
```

```
gaagtgcttg tatagctttt atctgcggct ttaaactgac agtacccgac tgtttattgg    4832
atctattgat ttgaaaagaa tttgttagga tagatcttaa gcagtaatct gtcagtgttt    4892
gtatttgtat tttctgcaat tttactgtga aaaaaaattt gttttcaaca attggtgtca    4952
ttttcttgat gtcactattt gttggagagt taaatggtct cttcccttg tgtatcttac     5012 ctagtgttta ctcctgggca cccttaatct tcagaggtgc taaattgtct gccattacac    5072
cagaaggatg cctctgatag gaggacaacc atgcaaattg tgaaatagtc ctgaagttct    5132
tggattactt tacacctcag tattgattg tcccagaatt ttctggcctt tcatggcaat     5192
gaaaatttta agaagaaaga tttaaagtat tttaatttta aagagtgtgt tataaaataa    5252
tgtactgaat tctttatccc attttatcat cctttcagtt tttattaatc tactgtatca    5312
ataaaattct gtaatttgaa tgagtaaaaa aaaaaaaaaa aaa                      5355
```

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: consensus
      sequence

<400> SEQUENCE: 5

```
ctawwagscc csgcscaw                                                  18
```

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: motif

<400> SEQUENCE: 6

```
Lys Lys Phe Thr Gln Val Leu Glu Asp Asp Glu Lys Ile Arg Lys
 1               5                  10                  15
```

<210> SEQ ID NO 7
<211> LENGTH: 7
<212> TYPE: PRT
<213> ORGANISM: Unknown
<220> FEATURE:
<223> OTHER INFORMATION: Elm1

<400> SEQUENCE: 7

```
Tyr Thr Leu Gly Val Ser Ala
 1               5
```

<210> SEQ ID NO 8
<211> LENGTH: 7
<212> TYPE: PRT
<213> ORGANISM: Unknown
<220> FEATURE:
<223> OTHER INFORMATION: Tsl

<400> SEQUENCE: 8

```
Tyr Ala Leu Leu Asn Leu Leu
 1               5
```

<210> SEQ ID NO 9
<211> LENGTH: 7
<212> TYPE: PRT
<213> ORGANISM: Yeast

<400> SEQUENCE: 9

Tyr His Leu Lys Gln Asn Ile
1               5

<210> SEQ ID NO 10
<211> LENGTH: 7
<212> TYPE: PRT
<213> ORGANISM: Unknown
<220> FEATURE:
<223> OTHER INFORMATION: CK1a

<400> SEQUENCE: 10

Tyr Lys Leu Val Arg Lys Ile
1               5

<210> SEQ ID NO 11
<211> LENGTH: 7
<212> TYPE: PRT
<213> ORGANISM: Unknown
<220> FEATURE:
<223> OTHER INFORMATION: Alk5

<400> SEQUENCE: 11

Ile Val Leu Gln Glu Ser Ile
1               5

<210> SEQ ID NO 12
<211> LENGTH: 8
<212> TYPE: PRT
<213> ORGANISM: Unknown
<220> FEATURE:
<223> OTHER INFORMATION: Ror2

<400> SEQUENCE: 12

Gly Glu Asp Arg Phe Gly Lys Val
1               5

<210> SEQ ID NO 13
<211> LENGTH: 8
<212> TYPE: PRT
<213> ORGANISM: Unknown
<220> FEATURE:
<223> OTHER INFORMATION: CK1a

<400> SEQUENCE: 13

Gly Ser Gly Ser Phe Gly Asp Ile
1               5

<210> SEQ ID NO 14
<211> LENGTH: 8
<212> TYPE: PRT
<213> ORGANISM: Unknown
<220> FEATURE:
<223> OTHER INFORMATION: Ypka

<400> SEQUENCE: 14

Ala Glu Gly Glu Ser His Ile Ser
1               5

<210> SEQ ID NO 15
<211> LENGTH: 8
<212> TYPE: PRT
<213> ORGANISM: Unknown
<220> FEATURE:
<223> OTHER INFORMATION: Mik1

<400> SEQUENCE: 15

-continued

```
His Glu Ser Asp Phe Ser Glu Val
1               5

<210> SEQ ID NO 16
<211> LENGTH: 7
<212> TYPE: PRT
<213> ORGANISM: Unknown
<220> FEATURE:
<223> OTHER INFORMATION: Ykl516

<400> SEQUENCE: 16

Leu Leu Tyr Glu Leu Met Asp
1               5

<210> SEQ ID NO 17
<211> LENGTH: 7
<212> TYPE: PRT
<213> ORGANISM: Unknown
<220> FEATURE:
<223> OTHER INFORMATION: PKN2

<400> SEQUENCE: 17

Tyr Leu Gly Glu Gln Val Ser
1               5

<210> SEQ ID NO 18
<211> LENGTH: 7
<212> TYPE: PRT
<213> ORGANISM: Unknown
<220> FEATURE:
<223> OTHER INFORMATION: BCK1

<400> SEQUENCE: 18

Tyr Leu Cys Leu Cys Leu Asn
1               5

<210> SEQ ID NO 19
<211> LENGTH: 11
<212> TYPE: PRT
<213> ORGANISM: Caenorhabditis elegans

<400> SEQUENCE: 19

Tyr Ala Met Lys Cys Leu Lys Lys Asp Val Ile
1               5                   10

<210> SEQ ID NO 20
<211> LENGTH: 11
<212> TYPE: PRT
<213> ORGANISM: Unknown
<220> FEATURE:
<223> OTHER INFORMATION: bARK1

<400> SEQUENCE: 20

Tyr Ala Met Lys Cys Leu Asp Lys Lys Arg Ile
1               5                   10

<210> SEQ ID NO 21
<211> LENGTH: 11
<212> TYPE: PRT
<213> ORGANISM: Drosophila melanogaster

<400> SEQUENCE: 21

Tyr Ala Met Lys Cys Leu Asp Lys Lys Arg Ile
1               5                   10

<210> SEQ ID NO 22
```

```
<211> LENGTH: 11
<212> TYPE: PRT
<213> ORGANISM: Unknown
<220> FEATURE:
<223> OTHER INFORMATION: CamK1

<400> SEQUENCE: 22

Val Ala Ile Lys Cys Ile Ala Lys Lys Ala Leu
1               5                   10

<210> SEQ ID NO 23
<211> LENGTH: 10
<212> TYPE: PRT
<213> ORGANISM: Unknown
<220> FEATURE:
<223> OTHER INFORMATION: Araf

<400> SEQUENCE: 23

Gln Ala Phe Lys Asn Glu Met Gln Val Leu
1               5                   10

<210> SEQ ID NO 24
<211> LENGTH: 10
<212> TYPE: PRT
<213> ORGANISM: Unknown
<220> FEATURE:
<223> OTHER INFORMATION: bARK1

<400> SEQUENCE: 24

Thr Leu Ala Leu Asn Glu Arg Ile Met Leu
1               5                   10

<210> SEQ ID NO 25
<211> LENGTH: 10
<212> TYPE: PRT
<213> ORGANISM: Unknown
<220> FEATURE:
<223> OTHER INFORMATION: SME1

<400> SEQUENCE: 25

Tyr Thr Arg Val Arg Glu Ile Lys Phe Ile
1               5                   10

<210> SEQ ID NO 26
<211> LENGTH: 8
<212> TYPE: PRT
<213> ORGANISM: Unknown
<220> FEATURE:
<223> OTHER INFORMATION: TPCKII

<400> SEQUENCE: 26

Leu Leu Asp Ile Val Lys Asp Pro
1               5

<210> SEQ ID NO 27
<211> LENGTH: 8
<212> TYPE: PRT
<213> ORGANISM: Unknown
<220> FEATURE:
<223> OTHER INFORMATION: Pim1

<400> SEQUENCE: 27

Leu Leu Asp Trp Phe Glu Arg Pro
1               5

<210> SEQ ID NO 28
<211> LENGTH: 8
```

```
<212> TYPE: PRT
<213> ORGANISM: Unknown
<220> FEATURE:
<223> OTHER INFORMATION: Klg

<400> SEQUENCE: 28

Leu Leu Gly Leu Cys Arg Glu Ala
1               5

<210> SEQ ID NO 29
<211> LENGTH: 8
<212> TYPE: PRT
<213> ORGANISM: Unknown
<220> FEATURE:
<223> OTHER INFORMATION: APK1

<400> SEQUENCE: 29

Leu Val Lys Leu Ile Gly Tyr Cys
1               5

<210> SEQ ID NO 30
<211> LENGTH: 8
<212> TYPE: PRT
<213> ORGANISM: Unknown
<220> FEATURE:
<223> OTHER INFORMATION: PvpK1

<400> SEQUENCE: 30

Ile Phe Ser Cys Leu Val Met Glu
1               5

<210> SEQ ID NO 31
<211> LENGTH: 8
<212> TYPE: PRT
<213> ORGANISM: Unknown
<220> FEATURE:
<223> OTHER INFORMATION: G11a

<400> SEQUENCE: 31

Lys Phe Ser Cys Leu Val Met Glu
1               5

<210> SEQ ID NO 32
<211> LENGTH: 8
<212> TYPE: PRT
<213> ORGANISM: Zea mays

<400> SEQUENCE: 32

Lys Phe Ser Cys Leu Val Met Glu
1               5

<210> SEQ ID NO 33
<211> LENGTH: 9
<212> TYPE: PRT
<213> ORGANISM: Unknown
<220> FEATURE:
<223> OTHER INFORMATION: Let23

<400> SEQUENCE: 33

Gly Asn Leu Gln Asn Phe Leu Lys Leu
1               5

<210> SEQ ID NO 34
<211> LENGTH: 9
<212> TYPE: PRT
<213> ORGANISM: Unknown
<220> FEATURE:
```

<223> OTHER INFORMATION: TORSO

<400> SEQUENCE: 34

Gly Ser Leu Gln Asn Phe Leu Arg Glu
1               5

<210> SEQ ID NO 35
<211> LENGTH: 9
<212> TYPE: PRT
<213> ORGANISM: Unknown
<220> FEATURE:
<223> OTHER INFORMATION: TGFbRII

<400> SEQUENCE: 35

Gly Asn Leu Gln Glu Tyr Leu Thr Arg
1               5

<210> SEQ ID NO 36
<211> LENGTH: 13
<212> TYPE: PRT
<213> ORGANISM: Unknown
<220> FEATURE:
<223> OTHER INFORMATION: CaMKIV

<400> SEQUENCE: 36

Glu Arg Asp Ala Asp Ala Val Lys Gln Ile Leu Glu Ala
1               5                   10

<210> SEQ ID NO 37
<211> LENGTH: 13
<212> TYPE: PRT
<213> ORGANISM: Unknown
<220> FEATURE:
<223> OTHER INFORMATION: PfCPK

<400> SEQUENCE: 37

Glu Cys Asp Ala Asn Ile Met Lys Gln Ile Leu Ser Gly
1               5                   10

<210> SEQ ID NO 38
<211> LENGTH: 13
<212> TYPE: PRT
<213> ORGANISM: Unknown
<220> FEATURE:
<223> OTHER INFORMATION: TORRTK

<400> SEQUENCE: 38

Ala Asp Gln Leu Asn Ile Ala Lys Gln Ile Ser Ala Gly
1               5                   10

<210> SEQ ID NO 39
<211> LENGTH: 12
<212> TYPE: PRT
<213> ORGANISM: Unknown
<220> FEATURE:
<223> OTHER INFORMATION: NPK1

<400> SEQUENCE: 39

Glu Ser Val Ile Met Tyr Thr Lys Gln Leu Leu Leu
1               5                   10

<210> SEQ ID NO 40
<211> LENGTH: 14
<212> TYPE: DNA
<213> ORGANISM: Homo sapiens

<400> SEQUENCE: 40

-continued

```
ttttcttgtt tcag                                                14

<210> SEQ ID NO 41
<211> LENGTH: 16
<212> TYPE: DNA
<213> ORGANISM: Homo sapiens

<400> SEQUENCE: 41
ttttattttt gtatag                                              16

<210> SEQ ID NO 42
<211> LENGTH: 16
<212> TYPE: DNA
<213> ORGANISM: Homo sapiens

<400> SEQUENCE: 42 tctttttta tttaag                                               16

<210> SEQ ID NO 43
<211> LENGTH: 12
<212> TYPE: DNA
<213> ORGANISM: Homo sapiens

<400> SEQUENCE: 43 ccttatttt ag                                                   12

<210> SEQ ID NO 44
<211> LENGTH: 13
<212> TYPE: DNA
<213> ORGANISM: Homo sapiens

<400> SEQUENCE: 44
ttttgaattg cag                                                 13

<210> SEQ ID NO 45
<211> LENGTH: 14
<212> TYPE: DNA
<213> ORGANISM: Homo sapiens

<400> SEQUENCE: 45
tttatgtttt tcag                                                14

<210> SEQ ID NO 46
<211> LENGTH: 15
<212> TYPE: DNA
<213> ORGANISM: Homo sapiens

<400> SEQUENCE: 46
ctttctcctc aaaag                                               15

<210> SEQ ID NO 47
<211> LENGTH: 11
<212> TYPE: DNA
<213> ORGANISM: Homo sapiens

<400> SEQUENCE: 47
ttttatttta g                                                   11

<210> SEQ ID NO 48
<211> LENGTH: 15
<212> TYPE: DNA
<213> ORGANISM: Homo sapiens
```

```
<400> SEQUENCE: 48
tttatatttt atcag                                                  15

<210> SEQ ID NO 49
<211> LENGTH: 13
<212> TYPE: DNA
<213> ORGANISM: Homo sapiens

<400> SEQUENCE: 49
tgttatcttt cag                                                    13

<210> SEQ ID NO 50
<211> LENGTH: 14
<212> TYPE: DNA
<213> ORGANISM: Homo sapiens

<400> SEQUENCE: 50
tttttgtttt taag                                                   14

<210> SEQ ID NO 51
<211> LENGTH: 15
<212> TYPE: DNA
<213> ORGANISM: Homo sapiens

<400> SEQUENCE: 51 tctgctttt tgtag                                                   15

<210> SEQ ID NO 52
<211> LENGTH: 14
<212> TYPE: DNA
<213> ORGANISM: Homo sapiens

<400> SEQUENCE: 52
tttgtgtttt tcag                                                   14

<210> SEQ ID NO 53
<211> LENGTH: 15
<212> TYPE: DNA
<213> ORGANISM: Homo sapiens

<400> SEQUENCE: 53
ttgtgtgatt tacag                                                  15

<210> SEQ ID NO 54
<211> LENGTH: 11
<212> TYPE: DNA
<213> ORGANISM: Homo sapiens

<400> SEQUENCE: 54 tttatttaa g                                                       11

<210> SEQ ID NO 55
<211> LENGTH: 15
<212> TYPE: DNA
<213> ORGANISM: Homo sapiens

<400> SEQUENCE: 55
taatctgtat tacag                                                  15

<210> SEQ ID NO 56
<211> LENGTH: 15
<212> TYPE: DNA
<213> ORGANISM: Homo sapiens
```

<400> SEQUENCE: 56
ttggtcatat tttag                                                    15

<210> SEQ ID NO 57
<211> LENGTH: 15
<212> TYPE: DNA
<213> ORGANISM: Homo sapiens

<400> SEQUENCE: 57
tgattcattt tatag                                                    15

<210> SEQ ID NO 58
<211> LENGTH: 14
<212> TYPE: DNA
<213> ORGANISM: Homo sapiens

<400> SEQUENCE: 58 tttttttta atag                                                      14

<210> SEQ ID NO 59
<211> LENGTH: 15
<212> TYPE: DNA
<213> ORGANISM: Homo sapiens

<400> SEQUENCE: 59 tccctcatt ttcag                                                     15

<210> SEQ ID NO 60
<211> LENGTH: 15
<212> TYPE: DNA
<213> ORGANISM: Homo sapiens

<400> SEQUENCE: 60
ctcgtttatt tttag                                                    15

<210> SEQ ID NO 61
<211> LENGTH: 15
<212> TYPE: DNA
<213> ORGANISM: Homo sapiens

<400> SEQUENCE: 61
ttgtctctta aatag                                                    15

<210> SEQ ID NO 62
<211> LENGTH: 15
<212> TYPE: DNA
<213> ORGANISM: Homo sapiens

<400> SEQUENCE: 62
ctactcattt ttcag                                                    15

<210> SEQ ID NO 63
<211> LENGTH: 14
<212> TYPE: DNA
<213> ORGANISM: Homo sapiens

<400> SEQUENCE: 63
ttgtgtcttt acag                                                     14

<210> SEQ ID NO 64
<211> LENGTH: 13
<212> TYPE: DNA

```
<213> ORGANISM: Homo sapiens

<400> SEQUENCE: 64
ttttcttttt cag                                                        13

<210> SEQ ID NO 65
<211> LENGTH: 14
<212> TYPE: DNA
<213> ORGANISM: Homo sapiens

<400> SEQUENCE: 65
tttttttttt ttag                                                       14

<210> SEQ ID NO 66
<211> LENGTH: 13
<212> TYPE: DNA
<213> ORGANISM: Homo sapiens

<400> SEQUENCE: 66
tatactattg cag                                                        13

<210> SEQ ID NO 67
<211> LENGTH: 15
<212> TYPE: DNA
<213> ORGANISM: Homo sapiens

<400> SEQUENCE: 67
ttctcttggt tgtag                                                      15

<210> SEQ ID NO 68
<211> LENGTH: 15
<212> TYPE: DNA
<213> ORGANISM: Homo sapiens

<400> SEQUENCE: 68
catttctcat ttcag                                                      15

<210> SEQ ID NO 69
<211> LENGTH: 15
<212> TYPE: DNA
<213> ORGANISM: Homo sapiens

<400> SEQUENCE: 69
tgtctgtatt aaaag                                                      15

<210> SEQ ID NO 70
<211> LENGTH: 15
<212> TYPE: DNA
<213> ORGANISM: Homo sapiens

<400> SEQUENCE: 70 tttttttcc cctag                                                       15

<210> SEQ ID NO 71
<211> LENGTH: 15
<212> TYPE: DNA
<213> ORGANISM: Homo sapiens

<400> SEQUENCE: 71
tcttccccaa agcag                                                      15

<210> SEQ ID NO 72
<211> LENGTH: 13
```

```
-continued
<212> TYPE: DNA
<213> ORGANISM: Homo sapiens

<400> SEQUENCE: 72
ctttcctttt aag                                                          13
```

ANDROGEN-INDUCED SUPPRESSOR OF CELL PROLIFERATION AND USES THEREOF

RELATED INFORMATION

This application claims priority to U.S. provisional Application No. 60/121,461, entitled "A NOVEL ANDROGEN-INDUCED SUPPRESSOR OF CELL PROLIFERATION AND USES THEREOF," filed on Feb. 24, 1999, incorporated herein in its entirety by this reference. The contents of all patents, patent applications, and references cited herein are expressly incorporated by reference in their entireties.

GOVERNMENT SPONSORED RESEARCH

This work was supported in part by PHS NIH grant CA-55574.

BACKGROUND OF THE INVENTION

Among men, carcinoma of the prostate is the second most common cancer and the second most common cause of death from cancer in the United States. Each year over 130,000 men are diagnosed with prostate cancer and over 30,000 will die from the disease ((1992) *MMWR* 41:459). Typically, 61% of all deaths from prostate cancer occur within five years of diagnosis and 88% within ten years (Smart (1997) *Cancer* 80:1835–1844). Moreover, despite the availability of risk assessment tools, the optimal therapy for treating prostate cancer remains controversial (Small (1998) *Drugs Aging* 13:71–81). For example, although certain markers of prostate cancer progression such as prostate-specific antigen (PSA) have proven valuable in the diagnosis and management of prostate cancer, as currently used, PSA is insufficiently sensitive and specific for early detection or staging of the malignancy (Daher et al. (1998) *Clin. Chem. Lab. Med.* 36:671–681).

In addition, in some patients with metastatic disease of the prostate, hormone therapy (e.g., antiandrogen, estrogen, etc.) is frequently used. However, many patients on hormone therapy develop hormone resistance and the management of hormone refractory disease is a major clinical problem (Ismail et al. (1997) *Tech. Urol.* 3:16–24). The death of patients from prostate cancer is related to the development of clones of cells capable of multiplying and metastasizing without androgen stimulation. To date, efforts to suppress these cells have been of limited success (Newling (1996) *Eur. Urol. Suppl.* 2:69–74). This is in part due to the fact that the initial events in the development of prostate cancer are not well understood.

Normally, cell numbers in the prostate gland are regulated by androgens through separate pathways that include a) inhibition of cell death (apoptosis), b) induction of cell proliferation (Step-1), and c) inhibition of cell proliferation (Step-2, proliferation shutoff). In normal tissue, the apoptotic and proliferative activities are minimal and apparently, Step-2 (inhibition of cell proliferation) maintains the integrity of the tissue. Prostate cancer cells evolve when this circuitry fails in the initial or early phases in prostate cancer.

SUMMARY OF THE INVENTION

A hope for managing prostate cancer lies in the earlier detection of the disease using improved diagnostic indicators, and developing markers that will allow for the more efficient and strategic use of hormone therapy, preferably in concert with improvements in the quality of life for patients with prostate cancer.

To this end, a novel androgen-induced tumor suppressor gene termed "Androgen Shutoff Gene 3" (AS3) has been discovered. This gene has a role in inhibiting cell proliferation and use as a marker for the efficient diagnosis and treatment of prostate cancer.

The present invention is based, at least in part, on the discovery of a novel androgen-induced tumor suppressor, referred to herein as "Androgen Shutoff Gene 3" or "AS3" nucleic acid and protein molecules. The AS3 molecules of the present invention are useful as targets for developing modulating agents of cell proliferation, particularly cells of the prostate. Accordingly, in one aspect, this invention provides isolated nucleic acid molecules encoding AS3 proteins or biologically active portions thereof, as well as nucleic acid fragments suitable as primers or hybridization probes for the detection of AS3-encoding nucleic acids.

In one embodiment, an AS3 nucleic acid molecule of the invention is at least 50%, 55%, 60%, 65%, 70%, 75%, 80%, 85%, 90%, 95%, 98%, or more identical to the nucleotide sequence (e.g., to the entire length of the nucleotide sequence) shown in SEQ ID NO:1 or 3.

In a preferred embodiment, the isolated nucleic acid molecule includes the nucleotide sequence shown SEQ ID NO:1 or 3, or a complement thereof. In another embodiment, the nucleic acid molecule includes SEQ ID NO:3 and nucleotides 66–4238 of SEQ ID NO:1.

In another embodiment, an AS3 nucleic acid molecule includes a nucleotide sequence encoding a protein having an amino acid sequence sufficiently homologous to the amino acid sequence of SEQ ID NO:2. In a preferred embodiment, an AS3 nucleic acid molecule includes a nucleotide sequence encoding a protein having an amino acid sequence at least 45%, 50%, 55%, 60%, 65%, 70%, 75%, 80%, 85%, 90%, 95%, 98% or more homologous to the entire length of the amino acid sequence of SEQ ID NO:2. In a related embodiment, the nucleic acid encodes a polypeptide fragment having at least 1391 amino acid residues of the amino acid sequence shown in SEQ ID NO: 2.

In another preferred embodiment, an isolated nucleic acid molecule encodes the amino acid sequence of human AS3. In yet another preferred embodiment, the nucleic acid molecule includes a nucleotide sequence encoding a protein having the amino acid sequence of SEQ ID NO:2.

Another embodiment of the invention features nucleic acid molecules, preferably AS3 nucleic acid molecules, which specifically detect AS3 nucleic acid molecules relative to nucleic acid molecules encoding non-AS3 proteins. For example, in one embodiment, such a nucleic acid molecule is at least 100–250, 250–300, 300–350, 350–400, 400–450, 450–500, 500–550, or 550–600 or more nucleotides in length and hybridizes under stringent conditions to a nucleic acid molecule comprising the nucleotide sequence shown in SEQ ID NO:1, or a complement thereof. In a related embodiment, the nucleic acid molecule can further contain a nucleotide sequence encoding a heterologous polypeptide.

In a related embodiment, the nucleic acid molecules are at least 15 (e.g., contiguous) nucleotides in length and hybridize under stringent conditions to nucleotides 1–5253 of SEQ ID NO:1.

In other preferred embodiments, the nucleic acid molecule encodes a naturally occurring allelic variant of a polypeptide comprising the amino acid sequence of SEQ ID NO:2, wherein the nucleic acid molecule hybridizes to a nucleic acid molecule comprising SEQ ID NO:1 or 3 under stringent conditions.

Another embodiment of the invention provides an isolated nucleic acid molecule which is antisense to an AS3 nucleic acid molecule, e.g., the coding strand of an AS3 nucleic acid molecule.

Another aspect of the invention provides a vector comprising an AS3 nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably an AS3 protein, by culturing in a suitable medium, a host cell, e.g., a mammalian host cell such as a non-human mammalian cell, of the invention containing a recombinant expression vector, such that the protein is produced.

Another aspect of this invention features isolated or recombinant AS3 proteins and polypeptides. In one embodiment, the isolated protein, preferably an AS3 protein has an amino acid sequence at least about 45%, 50%, 55%, 60%, 65%, 70%, 75%, 80%, 85%, 90%, 95%, 98% or more homologous to the amino acid sequence of SEQ ID NO:2.

In another embodiment, the invention features fragments of the AS3 protein having the amino acid sequence of SEQ ID NO:2, wherein the fragment comprises at least 15 amino acids (e.g., contiguous amino acids) of the amino acid sequence of SEQ ID NO:2. In another embodiment, the protein, preferably an AS3 protein, has the amino acid sequence of SEQ ID NO:2, respectively.

In another embodiment, the invention features an isolated protein, preferably an AS3 protein, which is encoded by a nucleic acid molecule consisting of a nucleotide sequence at least about 50%, 55%, 60%, 65%, 70%, 75%, 80%, 85%, 90%, 95%, 98% or more homologous to a nucleotide sequence of SEQ ID NO:1 or 3, or a complement thereof. This invention further features an isolated protein, preferably an AS3 protein, which is encoded by a nucleic acid molecule consisting of a nucleotide sequence which hybridizes under stringent hybridization conditions to a nucleic acid molecule comprising the nucleotide sequence of SEQ ID NO:1 or 3, or a complement thereof.

The proteins of the present invention or portions thereof, e.g., biologically active portions thereof, can be operatively linked to a non-AS3 polypeptide (e.g., heterologous amino acid sequences) to form fusion proteins. The invention further features antibodies, such as monoclonal or polyclonal antibodies, that specifically bind proteins of the invention, preferably AS3 proteins.

In another aspect, the present invention provides a method for detecting the presence of an AS3 polypeptide in a biological sample by contacting the biological sample with a compound capable of detecting an AS3 polypeptide. In one embodiment of this invention, the compound is an antibody. In another embodiment of this invention, a kit is featured that contains a compound that selectively binds to the polypeptide and instructions for use.

In another aspect, the present invention features a method for detecting the presence of an AS3 nucleic acid in a biological sample by contacting the biological sample with a nucleic acid probe or primer that selectively hybridizes to an AS3 molecule of the invention and indicating the presence of such a molecule. In other embodiments of this invention, the nucleic acid in the biological sample is RNA.

In another embodiment of the invention, a kit is provided comprising at least one reagent that binds a nucleic acid and instructions for use.

In another aspect, the invention provides for a method for identifying a compound that binds to an AS3 polypeptide or fragment by detecting direct binding of the compound, binding using a competition assay, or binding using an AS3 activity.

In yet another aspect, the invention provides a method for identifying a compound that modulates the activity of an AS3 polypeptide or fragment by contacting such a polypeptide or cell expressing such a polypeptide and determining the effect of the test compound on the activity of the polypeptide.

In another aspect, the invention provides a method for modulating AS3 activity comprising contacting a cell capable of expressing AS3 with a compound that modulates AS3 activity such that AS3 activity in the cell is modulated. In one embodiment, the agent inhibits AS3 activity. In another embodiment, the agent stimulates AS3 activity. In one embodiment, the compound modulates expression of AS3 by modulating transcription of an AS3 gene or translation of an AS3 mRNA.

In another aspect, the invention features a transgenic animal generated from a cell genetically engineered to lack nucleic acid encoding an AS3 polypeptide, where the transgenic animal lacks expression of the AS3 polypeptide.

In a related aspect, the invention features a transgenic animal generated from a cell that contains a substantially pure nucleic acid encoding a AS3 polypeptide, where the nucleic acid is expressed in the transgenic animal.

In another aspect, the invention features a method of identifying a compound that modulates cell proliferation. The method includes: (a) providing a cell that has an AS3 gene; (b) contacting the cell with a candidate compound; and (c) monitoring expression of the AS3 gene, where an alteration in the level of expression of the AS3 gene indicates the presence of a compound which modulates cell proliferation. In one preferred embodiment of this aspect, the alteration that is an increase indicates the compound is inhibiting cell proliferation, and the alteration that is a decrease indicates the compound is increasing cell proliferation.

In a related aspect, the invention features another method of identifying a compound that is able to modulate cell proliferation that includes: (a) providing a cell including a reporter gene operably linked to a promoter from an AS3 gene; (b) contacting the cell with a candidate compound; and (c) measuring expression of the reporter gene, where a change in the expression in response to the candidate compound identifies a compound that is able to modulate cell proliferation. In one preferred embodiment of this aspect, the alteration that is an increase indicates the compound is inhibiting cell proliferation.

In another aspect, the invention features a method of inhibiting the proliferation of a cell by administering an amount of AS3 polypeptide or fragment thereof sufficient to inhibit cell proliferation.

In related aspects, the invention includes methods of decreasing cell proliferation by either providing a transgene encoding a AS3 polypeptide or fragment thereof to a cell of an animal such that the transgene is positioned for expression in the cell; or by administering to the cell a compound which increases AS3 biological activity in a cell. In preferred embodiments, AS3 is from a mammal, the cell being treated is in a mammal, and the mammal has been diagnosed with a condition involving cell proliferation such as cancer (e.g., prostate cancer).

In two other aspects, the invention features methods of diagnosing a mammal for the presence of disease involving altered cell proliferation or an increased likelihood of developing a disease involving altered cell proliferation. The methods include isolating a sample of nucleic acid from the mammal and determining whether the nucleic acid includes a AS3 mutation, where the presence of a mutation is an indication that the animal has a cell proliferation disease or an increased likelihood of developing a disease involving cell proliferation; or measuring AS3 gene expression in a sample from an animal to be diagnosed, where an alteration in the expression or activity relative to a sample from an unaffected mammal is an indication that the mammal has a disease involving cell proliferation or increased likelihood of developing such a disease. In preferred embodiments, AS3 gene expression is measured by assaying the amount of AS3 polypeptide or AS3 biological activity in the sample (e.g., the AS3 polypeptide is measured by immunological methods), or AS3 gene expression is measured by assaying the amount of AS3 RNA in the sample. In other preferred embodiments, the mammal is a human and the method may be performed after or during hormone therapy (e.g., androgen therapy).

In another aspect, the invention features a kit for diagnosing a mammal for the presence of a disease involving altered cell proliferation or an increased likelihood of developing a disease involving altered cell proliferation that includes a substantially pure antibody that specifically binds a AS3 polypeptide. Another such kit includes material for measuring AS3 RNA (e.g., a probe). In a preferred embodiment, the material is a nucleic acid probe.

In a yet another aspect, the invention features a method of obtaining a AS3 polypeptide, including: (a) providing a cell with DNA encoding a AS3 polypeptide, the DNA being positioned for expression in the cell; (b) culturing the cell under conditions for expressing the DNA; and (c) isolating the AS3 polypeptide.

In a related aspect, the invention features a method of isolating an AS3 gene or portion thereof having sequence identity to human AS3. The method includes amplifying by polymerase chain reaction the AS3 gene or portion thereof using oligonucleotide primers wherein the primers (a) are each greater than 15 nucleotides in length; (b) each have regions of complementarity to opposite DNA strands in a region of the nucleotide sequence provided in SEQ ID NO: 1; and (c) optionally contain sequences capable of producing restriction endonuclease cut sites in the amplified product; and isolating the AS3 gene or portion thereof.

In another aspect of the invention, the invention features a method for detecting if a subject is at increased risk for developing prostate cancer including the steps of (a) detecting the presence of an AS3 nucleic acid or polypeptide and (b) observing whether or not a subject has reduced or absent AS3 levels as compared to a standard, e.g., normal age matched control, wherein said reduced or absent AS3 levels indicate that the subject is at an increased risk for developing prostate cancer. In a related embodiment, the invention features a kit that contains at least one reagent for detecting the presence of an AS3 molecule.

In another aspect, the invention provides a method of prognosis for prostate cancer by obtaining a biological sample from the subject, measuring AS3 levels, correlating those levels with a control, and determining a prognosis based on whether the subject's AS3 levels are above average or below average. In related embodiments, the method may be performed during or after hormone therapy (e.g., androgen therapy) and employs an antibody or nucleic acid probe to an AS3 molecule.

In even another aspect, the invention features a method for the treatment of prostate cancer comprising identifying a subject with prostate cancer or about to have prostate cancer, administering a hormone therapy, and determining if the subject exhibits a change in AS3 levels. In preferred embodiments, the invention provides a method for identifying subjects that exhibit increased AS3 levels after receiving hormone as responsive to hormone therapy and further, as candidates for intermittent hormone therapy. In other preferred embodiments, the hormone therapy is an androgen therapy, the subject is a human, and the method for measuring includes measuring AS3 nucleic acid or polypeptide levels is performed with an antibody or nucleic acid probe or primer.

Other features and advantages of the invention will be apparent from the following detailed description and claims.

BRIEF DESCRIPTION OF THE DRAWINGS

FIG. 1 depicts the cDNA sequence and predicted amino acid sequence of human AS3. The nucleotide sequence corresponds to 1 to 5253 of SEQ ID NO: 1. The amino acid sequence corresponds to amino acids 1 to 1391 of SEQ ID NO: 2. The coding region without the 5' and 3' untranslated regions of the human AS3 gene is shown in SEQ ID NO: 3. Numbers on the left indicate positions in base pairs. The amino acid sequence of the open reading frame is depicted under the coding strand. Numbers on the right indicate amino acid positions. Destabilizing signals found in the untranslated regions of AS3 are underlined and the polyadenylation signal and cleavage site are at base pair positions 5228–5233 and 5249–5253, respectively.

FIG. 2 depicts the N-terminal leucine repeat structure of the AS3 polypeptide. Numbers above the AS3 sequence indicate the positions as shown in the amino acid sequence of SEQ ID NO. 1 of the blocks where uninterrupted leucine (or isoleucine, valine) heptades occur: positions 55 to 117 of SEQ ID No. 1 (top line); positions 196 to 217 of SEQ ID No. 1 (second line left); positions 241 to 277 of SEQ ID No. 1 (second line right); positions 319 to 355 of SEQ ID No. 1 (bottom line left); and positions 375 to 404 of SEQ ID No. 1 (bottom line right).

FIG. 3 depicts sequence comparisons of the putative Mg-nucleotide triphosphate binding subdomains of AS3 with corresponding subdomains of various protein kinases. The boxes represent the Hanks' conserved subdomains, as indicated above each box. The top lines within the boxes show the consensus β-strand, loop, and α-helical secondary structure elements. The numbers in the second lines indicate the positions as shown in the amino acid sequence of SEQ ID NO. 1 of the corresponding conformations in the AS3 sequence. The actual AS3 motifs are shown in the third line: positions 419 to 424 of SEQ ID NO. 1 (Subdomain I β-strand 1); positions 426 to 433 of SEQ ID NO. 1 (Subdomain I MG-ATP binding loop); positions 453 to 459 of SEQ ID NO. 1 (Subdomain I β-strand 2); positions 472 to 482 of SEQ ID NO. 1 (Subdomain II β-strand 3); positions 489 to 498 of SEQ ID NO. 1 (Subdomain III α-helix C); positions 509 to 516 of SEQ ID NO. 1 (Subdomain IV β-strand 4); positions 525 to 531 of SEQ ID NO. 1 (Subdomain V β-strand 5); positions 540 to 548 of SEQ ID NO. 1 (Subdomain V α-helix D); and positions 554 to 566 of SEQ ID NO. 1 (Subdomain VIa α-helix E). Hanks' conserved subdomains from protein kinases of close similarity are represented in the lines below each subdomain of the AS3 sequence as indicated in the Figure: for Subdomain I β-strand 1, see SEQ ID Nos: 7–11; for Subdomain I MG-ATP binding loop, see SEQ ID Nos: 12–15; for Subdomain I β-strand 2, see SEQ ID Nos: 16–18; for Subdomain II β-strand 3, see SEQ ID Nos: 19–22; for Subdomain III α-helix C, see SEQ ID Nos: 23–25; for Subdomain IV β-strand 4, see SEQ ID Nos: 26–29; for Subdomain V β-strand 5, see SEQ ID Nos: 30–32; for Subdomain V α-helix D, see SEQ ID Nos.: 33–35; and for Subdomain VIa α-helix E, see SEQ ID Nos: 36–39. The names of the kinases are indicated in parentheses. Identical residues are highlighted. In the Mg-ATP binding loop, the "x" and lower case letters indicate non-conserved amino acids.

FIG. 5 depicts the genomic and cDNA positions as shown in SEQ ID NO. 1 of exons in the AS3 transcript. Asterisks represent the exon-intron boundaries. The area between asterisks represents the exons. Exon sequences are in upper case, the numbers represent cDNA positions as shown in the nucleotide sequence of SEQ ID NO. 1. Lower case letters are intron sequences, with the nucleotide sequences shown in FIG. 5 for the 3' end of each intron adjacent to the respective 5' end of each exon is found as follows: for the intron junction at Exon 2, see SEQ ID No.: 40; for the intron junction at Exon 3, see SEQ ID No.: 41; for the intron junction at Exon 4, see SEQ ID No.: 42; for the intron junction at Exon 5, see SEQ ID No.: 43; for the intron junction at Exon 6, see SEQ ID No.: 44; for the intron junction at Exon 7, see SEQ ID No.: 45; for the intron junction at Exon 8, see SEQ ID No.: 46; for the intron junction at Exon 9, see SEQ ID No.: 47; for the intron junction at Exon 10, see SEQ ID No.: 48; for the intron junction at Exon 11, see SEQ ID No.: 49; for the intron junction at Exon 12, see SEQ ID No.: 50; for the intron junction at Exon 13, see SEQ ID No.: 51; for the intron junction at Exon 14, see SEQ ID No.: 52; for the intron junction at Exon 15, see SEQ ID No.: 53; for the intron junction at Exon 16, see SEQ ID No.: 54; for the intron junction at Exon 17, see SEQ ID No.: 55; for the intron junction at Exon 18, see SEQ ID No.: 56; for the intron junction at Exon 19, see SEQ ID No.: 57; for the intron junction at Exon 20, see SEQ ID No.: 58; for the intron junction at Exon 21, see SEQ ID No.: 59; for the intron junction at Exon 22, see SEQ ID No.: 60; for the intron junction at Exon 23, see SEQ ID No.: 61; for the intron junction at Exon 24, see SEQ ID No.: 62; for the intron junction at Exon 25, see SEQ ID No.: 63; for the intron junction at Exon 26, see SEQ ID No.: 64; for the intron junction at Exon 27, see SEQ ID No.: 65; for the intron junction at Exon 28, see SEQ ID No.: 66; for the intron junction at Exon 29, see SEQ ID No.: 67; for the intron junction at Exon 30, see SEQ ID No.: 68; for the intron junction at Exon 31, see SEQ ID No.: 69; for the intron junction at Exon 32, see SEQ ID No.: 70; for the intron junction at Exon 33, see SEQ ID No.: 71; and for the intron junction at Exon 34, see SEQ ID No.: 72. Numbers of the first exon indicate positions in PAC26H23. Numbers in parenthesis refer to positions on cosmid 267p19, while numbers in brackets refer to PAC49J10 positions.

FIG. 6 depicts the cDNA sequence and predicted amino acid sequence of human AS3 having an additional 84 base pairs of untranslated 5' sequence as compared to the sequence presented in FIG. 1. The nucleotide sequence corresponds to 1 to 5337 of SEQ ID NO: 4. The amino acid sequence shown corresponds to amino acids 1 to 1391 of SEQ ID NO: 2. The coding region without the 5' and 3' untranslated regions of the human AS3 gene is shown in SEQ ID NO: 3. Numbers on the left indicate positions in base pairs. The amino acid sequence of the open reading frame is depicted under the coding strand. Numbers on the right indicate amino acid positions. Destabilizing signals found in the untranslated regions of AS3 are underlined and the polyadenylation signal and cleavage signal are at base pair positions 5312–5317 and 5333–5337, respectively. The number 5337 found in parentheses at the 3' terminus of the nucleotide sequence in FIGS. 6-2 indicates the position of the nucleotide residue T located to the left of the 18 residue polyA sequence.

DETAILED DESCRIPTION OF THE INVENTION

Figure 4:
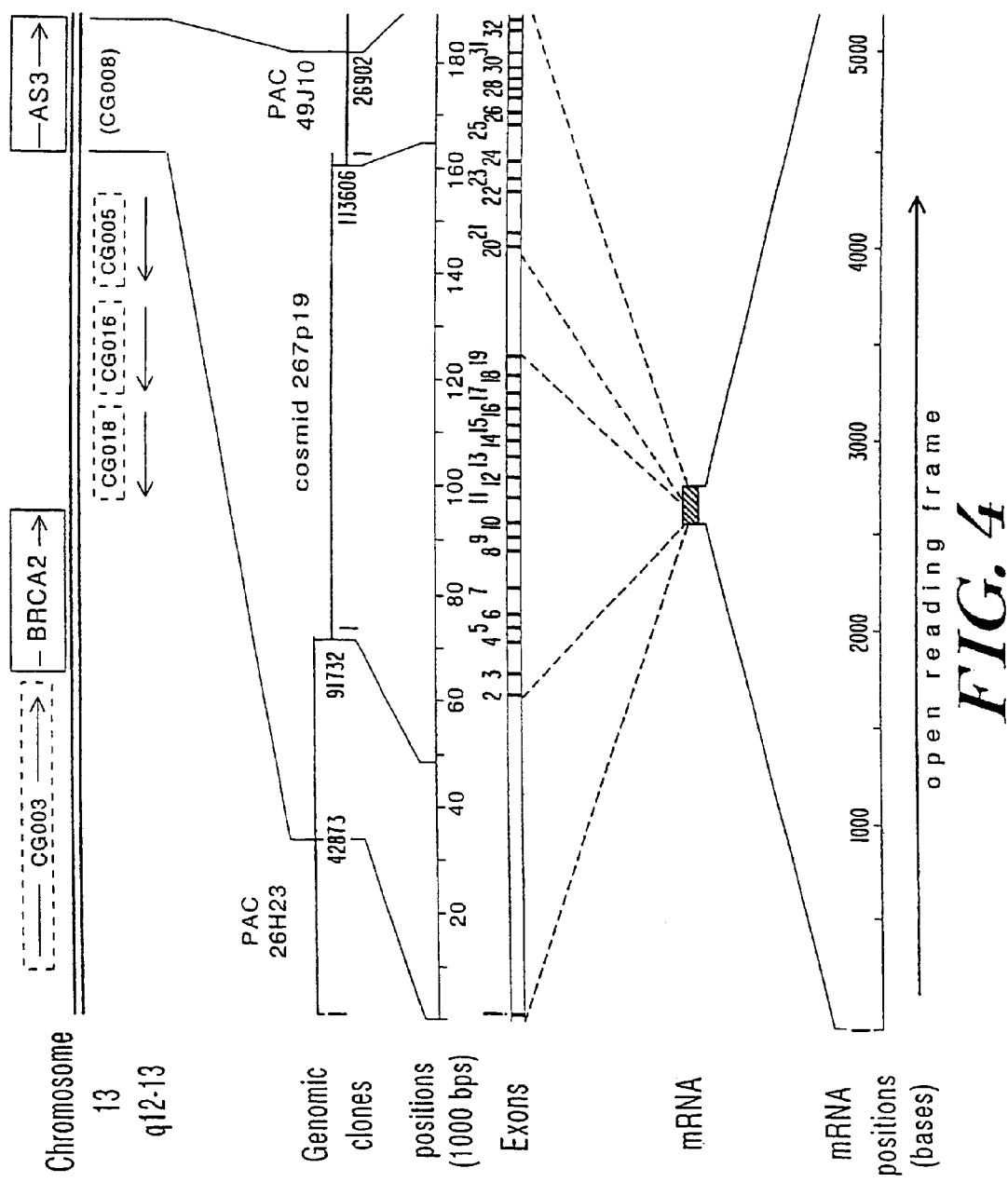
FIG. 4 depicts the genomic, cosmid, and exon maps of the AS3 cDNA. The chromosomal panel represents a 1 megabase (Mb) genomic region around BRCA2. Boxes with CG numbers are genomic areas where expression of transcripts were detected. The centromer is at the left. The P1 artificial chromosome (PAC) PAC26H23 (Accession No.: Z84467) overlaps with cosmid 267 p19 (Accession No.: Z75889), which, in turn, overlaps with PAC49J10 (Accession No.: Z84572). Numbers below the PAC and cosmid lines indicate positions within the genomic clone. The scale above the exon map indicates the genomic distance in thousands of base pairs. In the exon panel, black boxes represent the exons, while the numbers above them indicate exon numbers. In the mRNA panel, the numbers indicate nucleotide positions.

The present invention is based, at least in part, on the discovery of a novel molecule referred to herein as "Androgen Shutoff Gene 3" or "AS3" nucleic acid and protein molecules, which play a role in hormone-induced inhibition of cell proliferation. In one embodiment, the AS3 molecules are capable of modulating cell proliferation, e.g., cancer. In a preferred embodiment, the AS3 molecules are expressed in cells of the prostate and/or function in the cells of the prostate. In another preferred embodiment, the AS3 molecules are expressed in prostate cells when exposed to a hormone, e.g., an androgen, and inhibit cell proliferation.

The AS3 gene was cloned from a subtracted library made from a human prostate carcinoma cell line induced to undergo growth arrest using androgen.

Androgens regulate prostate cell numbers and cell proliferation by three major mechanisms: a) inhibition of cell death (apoptosis), b) induction of cell proliferation (Step- 1), and c) inhibition of cell proliferation (proliferative shutoff, Step-2) (Isaacs (1985) *Prostate* 5:545–557; Bruchovsky et al. (1975) *Vit. &Horm.* 33:61–102; Sonnenschein et al., (1989) *Cancer Res.* 49:3474–3481). Androgens affect epithelial and stromal cell types which, in turn, interact in the prostate (Hayward et al., (1997) *Brit. J. Urol. Suppl.* 2: 18–26). The human prostate LNCaP-FGC cell line that exhibits hormone responsiveness and is used extensively for endocrine and molecular studies (Sonnenschein et al., (1989) *Cancer Res.* 49:3474–3481; Horoszewicz et al., (1983) *Cancer Res.* 43:1809–1818; Soto et al., (1995) *Oncology Res.* 7: 545–558) was employed herein. Proliferation is inhibited in these cells by sex steroid-stripped (charcoal-dextran treated) human serum (CDHuS) (Sonnenschein et al., (1989) *Cancer Res.* 49:3474–3481). Low androgen concentrations cancel this inhibition (Step-1) and at higher levels, androgens induce an irreversible proliferative shutoff (Step-2) (Sonnenschein et al., (1989) *Cancer Res.* 49:3474–3481; Soto et al., (1995) *Oncology Res.* 7: 545–558). During the shutoff period, these cells remain in the $G_0/G_1$ phase of the cell cycle. Prostate specific antigen (PSA) induction, however, is still dependent on androgens in these postmitotic cells (Soto et al., (1995) *Oncology Res.* 7: 545–558).

To dissect androgen-mediated cell-cycle events, several androgen target cell lines that express only one of the steps of the androgen regulated proliferative response were generated. Two LNCaP variants were isolated: the LNCaP-TAC variant which expresses Step-1 only, and the LNCaP-TJA variant, which is resistant to the inhibitory effect of both CD serum and androgens (Soto et al., (1995) *Oncology Res.* 7: 545–558). LNCaP-LNO cells, established by Horoszewicz et al., proliferate maximally in the presence of CDHuS, express an androgen-induced proliferative shutoff, and undergo $G_0/G_1$ arrest (Step-2) at high androgen concentrations (Horoszewicz et al., (1983) *Cancer Res.* 43:1809–1818; Soto et al., (1995) *Oncology Res.* 7: 545–558). In addition to these human prostate cells, a new model to demonstrate the shutoff effect in another cell type was developed by stable transfection of a wild type androgen-receptor construct into breast carcinoma MCF-7 cells. These MCF7-AR1 cells are also able to evoke a proliferative shutoff in response to androgens (Szelei et al., (1997) *Endocrinology* 138: 1406–1412).

Using a differential subtractive amplification procedure, a set of genes induced in the proliferative shutoff response (Step-2) (Wang et al., (1991) *Proc. Natl. Acad. Sci. USA* 88: 11505–11509) was identified. In particular, a gene involved in this regulation, AS3 (androgen shutoff gene 3), that shows high expression in the early regulatory phase of androgen-induced proliferative shutoff in cell culture and in the prostates of castrated rats was identified.

The AS3 gene encodes a polypeptide of 1391-residues and has a molecular weight of about 186 kD. It has coiled-coil structures that usually participate in protein—protein interactions, a perfect leucine-zipper that suggests DNA binding, nuclear localization motifs, proline- and serine-rich domains, unique C-terminal acidic-basic repeats, and ATP- and DNA-binding motifs.

The transcript has 34 exons in a 200,000 bp region on chromosome 13q12–q13, downstream of the breast cancer susceptibility gene BRCA2, and centromeric to the retinoblastoma (Rb1) locus. This area is subject to frequent allelic losses in cancers, and is believed to carry a number of cryptic suppressor genes.

The AS3 gene is involved in the regulation of androgen-induced proliferative arrest in human prostate cells. Accordingly, the AS3 molecules described below serve as useful diagnostic markers or therapeutic agents to control conditions of aberrant cell proliferation, such as cancer (e.g., cancer of the prostate).

In one embodiment, the present invention is directed at human AS3, however, AS3 family members are also intended to be within the scope of the invention. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

To identify the presence of important domains in a given polypeptide, and make the determination that a protein of interest has a particular profile, the amino acid sequence of the protein can be searched against several databases as described in Example 3. Using these tools, a number of important domains within the AS3 polypeptide have been identified and these results are set forth in FIGS. 2 and 3 and further described in Example 3.

Isolated proteins of the present invention, preferably AS3 proteins, have an amino acid sequence sufficiently homologous to the amino acid sequence of SEQ ID NO:2 or are encoded by a nucleotide sequence sufficiently homologous to SEQ ID NO:1 or 3. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently homologous. Furthermore, amino acid or nucleotide sequences which share at least 30%, 40%, or 50%, preferably 60%, more preferably 70–80%, or 90–95% homology and share a common functional activity are defined herein as sufficiently homologous.

As used interchangeably herein, an "AS3 activity", "biological activity of AS3" or "functional activity of AS3", refers to an activity exerted by an AS3 protein, polypeptide or nucleic acid molecule on an AS3 responsive cell or on an AS3 protein substrate, as determined in vivo, or in vitro, according to standard techniques. In one embodiment, an AS3 activity is a direct activity, such as an association with an AS3-target molecule. As used herein, a "target molecule" or "binding partner" is a molecule with which an AS3 protein binds or interacts in nature, such that AS3-mediated function is achieved. An AS3 target molecule can be a non-AS3 molecule or an AS3 protein or polypeptide of the present invention. Alternatively, an AS3 activity is an indirect activity, such as modulating cell cycle events. Preferably, an AS3 activity is the ability to modulate androgen-mediated cell proliferation.

Accordingly, another embodiment of the invention features isolated AS3 proteins and polypeptides having an AS3 activity. Preferred proteins are AS3 proteins encoded by a nucleic acid molecule having a nucleotide sequence which hybridizes under stringent hybridization conditions to a nucleic acid molecule comprising the nucleotide sequence of SEQ ID NO:1 or 3.

The nucleotide sequence of the isolated human AS3 cDNA and the predicted amino acid sequence of the human AS3 polypeptide are shown in FIG. 1 and in SEQ ID NOs:1 and 2, respectively.

The human AS3 gene, which is approximately 5253 nucleotides in length, encodes a protein having a molecular weight of approximately 186 kD and which is approximately 1391 amino acid residues in length.

Various aspects of the invention are described in further detail in the following subsections:

I. Isolated Nucleic Acid Molecules

One aspect of the invention pertains to isolated nucleic acid molecules that encode AS3 proteins or biologically active portions thereof, as well as nucleic acid fragments sufficient for use as hybridization probes to identify AS3-encoding nucleic acid molecules (e.g., AS3 mRNA) and fragments for use as PCR primers for the amplification or mutation of AS3 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated AS3 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (see FIG. 4). Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1 or 3, or a portion thereof, can be isolated using standard molecular biology techniques and the sequence information provided herein. Using all or portion of the nucleic acid sequence of SEQ ID NO:1 or 3, as a hybridization probe, AS3 nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989). In a related embodiment, the invention features an AS3 nucleic acid molecule having the sequence of SEQ ID NO: 4 (see FIG. 6) which is identical to the AS3 sequence provided in SEQ ID NO:1 (see FIG. 1) except for an additional 84 base pairs at the 5' end of the molecule. One skilled in the art would recognize that this additional untranslated 5' sequence may indicate that an alternative start site for the beginning of transcription of the AS3 mRNA molecule may exist.

Moreover, a nucleic acid molecule encompassing all or a portion of SEQ ID NO:1 or 3, can be isolated by the polymerase chain reaction (PCR) using synthetic oligonucleotide primers designed based upon the sequence of SEQ ID NO:1 or 3.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to AS3 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the human AS3 cDNA. This cDNA comprises sequences encoding the human AS3 protein (i.e., "the coding region", from nucleotides 66–4238), as well as 5' untranslated sequences (nucleotides 1–65) and 3' untranslated sequences (nucleotides 4239–5253). Alternatively, the nucleic acid molecule can comprise only the coding region of SEQ ID NO:1 (e.g., nucleotides 66–4238, corresponding to SEQ ID NO:3).

In another preferred embodiment, an isolated nucleic acid molecule of the invention comprises a nucleic acid molecule which is a complement of the nucleotide sequence shown in SEQ ID NO:1 or 3, or a portion of any of these nucleotide sequences. A nucleic acid molecule which is complementary to the nucleotide sequence shown in SEQ ID NO:1 or 3 is one which is sufficiently complementary to the nucleotide sequence shown in SEQ ID NO:1 or 3, such that it can hybridize to the nucleotide sequence shown in SEQ ID NO:1 or 3, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 98% or more homologous to the entire length of the nucleotide sequence shown in SEQ ID NO:1 or 3, or a portion of any of these nucleotide sequences.

Moreover, the nucleic acid molecule of the invention can comprise only a portion of the nucleic acid sequence of SEQ ID NO:1 or 3, for example, a fragment which can be used as a probe or primer or a fragment encoding a portion of an AS3 protein, e.g., a biologically active portion of an AS3 protein. The nucleotide sequence determined from the cloning of the AS3 gene allows for the generation of probes and primers designed for use in identifying and/or cloning other AS3 family members, as well as AS3 homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1 or 3, of an anti-sense sequence of SEQ ID NO:1 or 3 or of a naturally occurring allelic variant or mutant of SEQ ID NO:1 or 3. In an exemplary embodiment, a nucleic acid molecule of the present invention comprises a nucleotide sequence which is greater than 100–150, 150–200, 200–250, 250–300, 300–350, 350–400, 400–450, 450–500, 500–550, 550–600, 600–650, 650–700, 700–750, 750–800, 800–850, 850–900, 900–950, 950–1000, or more nucleotides in length and hybridizes under stringent hybridization conditions to a nucleic acid molecule of SEQ ID NO:1 or 3.

Probes based on the AS3 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress an AS3 protein, such as by measuring a level of an AS3-encoding nucleic acid in a sample of cells from a subject e.g., detecting AS3 mRNA levels or determining whether a genomic AS3 gene has been mutated or deleted.

A nucleic acid fragment encoding a "biologically active portion of an AS3 protein" can be prepared by isolating a portion of the nucleotide sequence of SEQ ID NO:1 or 3, which encodes a polypeptide having an AS3 biological activity (the biological activities of the AS3 proteins are described herein), expressing the encoded portion of the AS3 protein (e.g., by recombinant expression in vitro) and assessing the activity of the encoded portion of the AS3 protein.

The invention further encompasses nucleic acid molecules that differ from the nucleotide sequence shown in SEQ ID NO:1 or 3, due to degeneracy of the genetic code and thus encode the same AS3 proteins as those encoded by the nucleotide sequence shown in SEQ ID NO:1 or 3. In another embodiment, an isolated nucleic acid molecule of the invention has a nucleotide sequence encoding a protein having an amino acid sequence shown in SEQ ID NO:2.

In addition to the AS3 nucleotide sequences shown in SEQ ID NO:1 or 3, it will be appreciated by those skilled in the art that DNA sequence polymorphisms that lead to changes in the amino acid sequences of the AS3 proteins may exist within a population (e.g., the human population). Such genetic polymorphism in the AS3 genes may exist among individuals within a population due to natural allelic variation. As used herein, the terms "gene" and "recombinant gene" refer to nucleic acid molecules which include an open reading frame encoding an AS3 protein, preferably a mammalian AS3 protein, and can further include non-coding regulatory sequences, and introns.

Allelic variants of human AS3 include both functional and non-functional AS3 proteins. Functional allelic variants are naturally occurring amino acid sequence variants of the human AS3 protein that maintain the ability to modulate cell proliferation, e.g., androgen-induced changes in cell proliferation. Functional allelic variants will typically contain only conservative substitution of one or more amino acids of SEQ ID NO:2 or substitution, deletion or insertion of non-critical residues in non-critical regions of the protein.

Non-functional allelic variants are naturally occurring amino acid sequence variants of the human AS3 protein that do not have the ability to modulate cell proliferation, for example, hormone-induced changes in cell proliferation. Non-functional allelic variants will typically contain a non-conservative substitution, a deletion, or insertion or premature truncation of the amino acid sequence of SEQ ID NO:2 or a substitution, insertion or deletion in critical residues or critical regions.

The present invention further provides non-human orthologues of the human AS3 protein. Orthologues of the human AS3 protein are proteins that are isolated from non-human organisms and possess the same AS3 ability to modulate cell proliferation, for example, hormone-induced changes in cell proliferation. Orthologues of the human AS3 protein can readily be identified as comprising an amino acid sequence that is substantially homologous to SEQ ID NO:2.

Moreover, nucleic acid molecules encoding other AS3 family members and, thus, which have a nucleotide sequence which differs from the AS3 sequences of SEQ ID NO:1 or 3, are intended to be within the scope of the invention. For example, another AS3 cDNA can be identified based on the nucleotide sequence of human AS3. Moreover, nucleic acid molecules encoding AS3 proteins from different species, and which, thus, have a nucleotide sequence which differs from the AS3 sequences of SEQ ID NO:1 or 3, are intended to be within the scope of the invention. For example, a mouse AS3 cDNA can be identified based on the nucleotide sequence of a human AS3.

Nucleic acid molecules corresponding to natural allelic variants and homologues of the AS3 cDNAs of the invention can be isolated based on their homology to the AS3 nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the AS3 cDNAs of the invention can further be isolated by mapping to the same chromosome or locus as the AS3 gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1 or 3. In other embodiment, the nucleic acid is at least 30, 50, 100, 150, 200, 250, 253, 300, 350, 400, 450, 500, 550, 600, 650, 700, 750, 800, 850, 900, or 950 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in Current Protocols in Molecular Biology, John Wiley & Sons, N.Y. (1989), 6.3.1–6.3.6. A preferred, non-limiting example of stringent hybridization conditions are hybridization in 6×sodium chloride/sodium citrate (SSC) at about 45 C, followed by one or more washes in 0.2×SSC, 0.1% SDS at 50° C., preferably at 55° C., more preferably at 60° C., and even more preferably at 65° C. Preferably, an isolated nucleic acid molecule of the invention that hybridizes under stringent conditions to the sequence of SEQ ID NO:1 or 3 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the AS3 sequences that may exist in the population, the skilled artisan will further appreciate that changes can be introduced by mutation into the nucleotide sequences of SEQ ID NO:1 or 3, thereby leading to changes in the amino acid sequence of the encoded AS3 proteins, without altering the functional ability of the AS3 proteins. For example, nucleotide substitutions leading to amino acid substitutions at "non-essential" amino acid residues can be made in the sequence of SEQ ID NO:1 or 3. A "non-essential" amino acid residue is a residue that can be altered from the wild-type sequence of AS3 (e.g., the sequence of SEQ ID NO:2) without altering the biological activity, whereas an "essential" amino acid residue is required for biological activity. For example, amino acid residues that are conserved among the AS3 proteins of the present invention, e.g., those present in the heptad repeat or kinase domains, are predicted to be particularly recalcitrant to alteration. Furthermore, additional amino acid residues that are conserved between the AS3 proteins of the present invention and other members of the ASIC family are not likely to be amenable to alteration.

Accordingly, another aspect of the invention pertains to nucleic acid molecules encoding AS3 proteins that contain changes in amino acid residues that are not essential for activity. Such AS3 proteins differ in amino acid sequence from SEQ ID NO:2, yet retain biological activity. In one embodiment, the isolated nucleic acid molecule comprises a nucleotide sequence encoding a protein, wherein the protein comprises an amino acid sequence at least about 45%, 50%, 55%, 60%, 65%, 70%, 75%, 80%, 85%, 90%, 95%, 98% or more homologous to SEQ ID NO:2.

An isolated nucleic acid molecule encoding an AS3 protein homologous to the protein of SEQ ID NO:2 can be created by introducing one or more nucleotide substitutions, additions or deletions into the nucleotide sequence of SEQ ID NO:1 or 3, such that one or more amino acid substitutions, additions or deletions are introduced into the encoded protein. Mutations can be introduced into SEQ ID NO:1 or 3 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an AS3 protein is preferably replaced with another amino acid residue from the same side chain family. Alternatively, in another embodiment, mutations can be introduced randomly along all or part of an AS3 coding sequence, such as by saturation mutagenesis, and the resultant mutants can be screened for AS3 biological activity to identify mutants that retain activity. Following mutagenesis of SEQ ID NO:1 or 3, the encoded protein can be expressed recombinantly and the activity of the protein can be determined.

In a preferred embodiment, a mutant AS3 protein can be assayed for the ability to ability to modulate cell proliferation, for example, hormone-induced changes in cell proliferation.

In addition to the nucleic acid molecules encoding AS3 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire AS3 coding strand, or to only a portion thereof. In one embodiment, an antisense nucleic acid molecule is antisense to a "coding region" of the coding strand of a nucleotide sequence encoding AS3. The term "coding region" refers to the region of the nucleotide sequence comprising codons which are translated into amino acid residues (e.g., the coding region of human AS3 corresponds to SEQ ID NO:3). In another embodiment, the antisense nucleic acid molecule is antisense to a "noncoding region" of the coding strand of a nucleotide sequence encoding AS3. The term "noncoding region" refers to 5' and 3' sequences which flank the coding region that are not translated into amino acids (i.e., also referred to as 5' and 3' untranslated regions).

Given the coding strand sequences encoding AS3 disclosed herein (e.g., SEQ ID NO:3), antisense nucleic acids of the invention can be designed according to the rules of Watson and Crick base pairing. The antisense nucleic acid molecule can be complementary to the entire coding region of AS3 mRNA, but more preferably is an oligonucleotide which is antisense to only a portion of the coding or noncoding region of AS3 mRNA. For example, the antisense oligonucleotide can be complementary to the region surrounding the translation start site of AS3 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl- 2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an AS3 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave AS3 mRNA transcripts to thereby inhibit translation of AS3 mRNA. A ribozyme having specificity for an AS3-encoding nucleic acid can be designed based upon the nucleotide sequence of an AS3 cDNA disclosed herein (i.e., SEQ ID NO:1 or 3. For example, a derivative of a Tetrahymena L-19 IVS RNA can be constructed in which the nucleotide sequence of the active site is complementary to the nucleotide sequence to be cleaved in an AS3-encoding mRNA. See, e.g., Cech et al. U.S. Pat. No. 4,987,071; and Cech et al. U.S. Pat. No. 5,116,742. Alternatively, AS3 mRNA can be used to select a catalytic RNA having a specific ribonuclease activity from a pool of RNA molecules. See, e.g., Bartel, D. and Szostak, J. W. (1993) *Science* 261:1411–1418.

Alternatively, AS3 gene expression can be inhibited by targeting nucleotide sequences complementary to the regulatory region of the AS3 (e.g., the AS3 promoter and/or enhancers) to form triple helical structures that prevent transcription of the AS3 gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

In yet another embodiment, the AS3 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic &Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670–675.

PNAs of AS3 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of AS3 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of AS3 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of AS3 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated AS3 Proteins

One aspect of the invention pertains to isolated AS3 proteins, and biologically active portions thereof, as well as polypeptide fragments suitable for use as immunogens to raise anti-AS3 antibodies. In one embodiment, native AS3 proteins can be isolated from cells or tissue sources by an appropriate purification scheme using standard protein purification techniques. In another embodiment, AS3 proteins are produced by recombinant DNA techniques. Alternative to recombinant expression, an AS3 protein or polypeptide can be synthesized chemically using standard peptide synthesis techniques.

An "isolated" or "purified" protein or biologically active portion thereof is substantially free of cellular material or other contaminating proteins from the cell or tissue source from which the AS3 protein is derived, or substantially free from chemical precursors or other chemicals when chemically synthesized. The language "substantially free of cellular material" includes preparations of AS3 protein in which the protein is separated from cellular components of the cells from which it is isolated or recombinantly produced. In one embodiment, the language "substantially free of cellular material" includes preparations of AS3 protein having less than about 30% (by dry weight) of non-AS3 protein (also referred to herein as a "contaminating protein"), more preferably less than about 20% of non-AS3 protein, still more preferably less than about 10% of non-AS3 protein, and most preferably less than about 5% non-AS3 protein. When the AS3 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of AS3 protein in which the protein is separated from chemical precursors or other chemicals which are involved in the synthesis of the protein. In one embodiment, the language "substantially free of chemical precursors or other chemicals" includes preparations of AS3 protein having less than about 30% (by dry weight) of chemical precursors or non-AS3 chemicals, more preferably less than about 20% chemical precursors or non-AS3 chemicals, still more preferably less than about 10% chemical precursors or non-AS3 chemicals, and most preferably less than about 5% chemical precursors or non-AS3 chemicals.

As used herein, a "biologically active portion" of an AS3 protein includes a fragment of an AS3 protein which participates in an interaction between an AS3 molecule and a non-AS3 molecule. Biologically active portions of an AS3 protein include peptides comprising amino acid sequences sufficiently homologous to or derived from the amino acid sequence of the AS3 protein, e.g., the amino acid sequence shown in SEQ ID NO:2, which include less amino acids than the full length AS3 proteins, and exhibit at least one activity of an AS3 protein. Typically, biologically active portions comprise a domain or motif with at least one activity of the AS3 protein, e.g., the ability to modulate cell proliferation. A biologically active portion of an AS3 protein can be a polypeptide which is, for example, 10, 25, 50, 100, 200 or more amino acids in length. Biologically active portions of an AS3 protein can be used as targets for developing agents which modulate an AS3 mediated activity, e.g., cell proliferation.

In one embodiment, a biologically active portion of an AS3 protein comprises at least one heptad repeat. It is to be understood that a preferred biologically active portion of an AS3 protein of the present invention may contain two, three, four, or five heptad repeats. As used herein, the term "heptad repeat" includes a protein domain which contains either a leucine or similar hydrophobic residue (e.g., isoleucine, valine, or tyrosine) in every seventh position over a stretch of at least 20–30 amino acid residues, more preferably at least 20–25 amino acid residues, and most preferably at least 22 amino acid residues. Typically, the heptad repeat is uninterrupted, and can participate in protein—protein interactions. The leucine-zipper motif of DNA binding proteins is a specific subclass of this general pattern and is encompassed by the above term. Leucine zipper domains are described in, for example, Landschultz et al. (1988) *Science* 240: 1759–1764, the contents of which are incorporated herein by reference. Amino acid residues 55–161, 196–217, 241–277, 319–355, and 375–404 of the AS3 protein all comprise heptad repeats.

In another embodiment, a biologically active portion of an AS3 protein comprises a least one kinase-related domain. It is understood that a preferred biologically active portion of an AS3 protein of the present invention may contain two, three, four, five, six, seven, eight, or nine kinase-related domains. As used herein, the term "kinase-related domain" includes a polypeptide consensus motif having high homology to a known protein kinase catalytic domain as described in Hanks et al. (1988) *Meth. Enzymol.* 200:38–62 (the contents of which are incorporated herein by reference). In particular, a kinase-related domain is any one of the nine consensus motifs or related sequences set forth in FIG. 3.

In another embodiment, a biologically active portion of an AS3 protein can have kinase activity. As referred to herein, "kinase activity" is an activity associated with a protein or polypeptide which is capable of modulating its own phosphorylation state or the phosphorylation state of another protein or polypeptide. Proteins with kinase activity play a role in signaling pathways associated with cellular growth.

Moreover, other biologically active portions, in which other regions of the protein are deleted, can be prepared by recombinant techniques and evaluated for one or more of the functional activities of a native AS3 protein.

In a preferred embodiment, the AS3 protein has an amino acid sequence shown in SEQ ID NO:2. In other embodiments, the AS3 protein is substantially homologous to SEQ ID NO:2, and retains the functional activity of the protein of SEQ ID NO:2, yet differs in amino acid sequence due to natural allelic variation or mutagenesis, as described in detail in subsection I above. Accordingly, in another embodiment, the AS3 protein is a protein which comprises an amino acid sequence at least about 45%, 50%, 55%, 60%, 65%, 70%, 75%, 80%, 85%, 90%, 95%, 98% or more homologous to SEQ ID NO:2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the AS3 amino acid sequence of SEQ ID NO: 2 having 400 amino acid residues, at least 80, preferably at least 100, more preferably at least 120, even more preferably at least 140, and even more preferably at least 150, 200, 300, or 400 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available online at the GCG website), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online at the GCG website), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.,* 4:11–17 (1988)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to AS3 nucleic acid molecules of the invention. BLAST protein searches can be performed with the XBLAST program, score=50, wordlength=3 to obtain amino acid sequences homologous to AS3 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used, which are available online at the National Center for Biotechnology Information.

The invention also provides AS3 chimeric or fusion proteins. As used herein, an AS3 "chimeric protein" or "fusion protein" comprises an AS3 polypeptide operatively linked to a non-AS3 polypeptide. An "AS3 polypeptide" refers to a polypeptide having an amino acid sequence corresponding to AS3, whereas a "non-AS3 polypeptide" refers to a polypeptide having an amino acid sequence corresponding to a protein which is not substantially homologous to the AS3 protein, e.g., a protein which is different from the AS3 protein and which is derived from the same or a different organism. Within an AS3 fusion protein the AS3 polypeptide can correspond to all or a portion of an AS3 protein. In a preferred embodiment, an AS3 fusion protein comprises at least one biologically active portion of an AS3 protein. In another preferred embodiment, an AS3 fusion protein comprises at least two biologically active portions of an AS3 protein. Within the fusion protein, the term "operatively linked" is intended to indicate that the AS3 polypeptide and the non-AS3 polypeptide are fused in-frame to each other. The non-AS3 polypeptide can be fused to the N-terminus or C-terminus of the AS3 polypeptide.

For example, in one embodiment, the fusion protein is a GST-AS3 fusion protein in which the AS3 sequences are fused to the C-terminus of the GST sequences. Such fusion proteins can facilitate the purification of recombinant AS3.

In another embodiment, the fusion protein is an AS3 protein containing a heterologous signal sequence at its N-terminus. In certain host cells (e.g., mammalian host cells), expression and/or secretion of AS3 can be increased through use of a heterologous signal sequence.

The AS3 fusion proteins of the invention can be incorporated into pharmaceutical compositions and administered to a subject in vivo. The AS3 fusion proteins can be used to affect the bioavailability of an AS3 substrate. Use of AS3 fusion proteins may be useful therapeutically for the treatment of disorders caused by, for example, (i) aberrant modification or mutation of a gene encoding an AS3 protein; (ii) mis-regulation of the AS3 gene; and (iii) aberrant post-translational modification of an AS3 protein.

Moreover, the AS3-fusion proteins of the invention can be used as immunogens to produce anti-AS3 antibodies in a subject, to purify AS3 ligands and in screening assays to identify molecules which inhibit the interaction of AS3 with an AS3 substrate.

Preferably, an AS3 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology,* eds. Ausubel et al. John Wiley & Sons: 1992). Moreover, many expression vectors are commercially available that already encode a fusion moiety (e.g., a GST polypeptide). An AS3-encoding nucleic acid can be cloned into such an expression vector such that the fusion moiety is linked in-frame to the AS3 protein.

The present invention also pertains to variants of the AS3 proteins which function as either AS3 agonists (mimetics) or as AS3 antagonists. Variants of the AS3 proteins can be generated by mutagenesis, e.g., discrete point mutation or truncation of an AS3 protein. An agonist of the AS3 proteins can retain substantially the same, or a subset, of the biological activities of the naturally occurring form of an AS3 protein. An antagonist of an AS3 protein can inhibit one or more of the activities of the naturally occurring form of the AS3 protein by, for example, competitively modulating an AS3-mediated activity of an AS3 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the AS3 protein.

In one embodiment, variants of an AS3 protein which function as either AS3 agonists (mimetics) or as AS3 antagonists can be identified by screening combinatorial libraries of mutants, e.g., truncation mutants, of an AS3 protein for AS3 protein agonist or antagonist activity. In one embodiment, a variegated library of AS3 variants is generated by combinatorial mutagenesis at the nucleic acid level and is encoded by a variegated gene library. A variegated library of AS3 variants can be produced by, for example, enzymatically ligating a mixture of synthetic oligonucleotides into gene sequences such that a degenerate set of potential AS3 sequences is expressible as individual polypeptides, or alternatively, as a set of larger fusion proteins (e.g., for phage display) containing the set of AS3 sequences therein. There are a variety of methods which can be used to produce libraries of potential AS3 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential AS3 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of an AS3 protein coding sequence can be used to generate a variegated population of AS3 fragments for screening and subsequent selection of variants of an AS3 protein. In one embodiment, a library of coding sequence fragments can be generated by treating a double stranded PCR fragment of an AS3 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the AS3 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of AS3 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify AS3 variants (Arkin and Yourvan (1992) *Proc. Natl. Acad. Sci. USA* 89:7811–7815; Delgrave et al. (1993) *Protein Engineering* 6(3):327–331).

In one embodiment, cell based assays can be exploited to analyze a variegated AS3 library. For example, a library of expression vectors can be transfected into a cell line, e.g., a neuronal cell line, which ordinarily responds to a particular ligand in an AS3-dependent manner. The transfected cells are then contacted with the ligand and the effect of expression of the mutant on signaling by the ligand can be detected, e.g., by measuring intracellular calcium, potassium, or sodium concentration, neuronal membrane depolarization, or the activity of an AS3-regulated transcription factor. Plasmid DNA can then be recovered from the cells which score for inhibition, or alternatively, potentiation of signaling by the ligand, and the individual clones further characterized.

III Anti-AS3 Antibodies

An isolated AS3 protein, or a portion or fragment thereof, can be used as an immunogen to generate antibodies that bind AS3 using standard techniques for polyclonal and monoclonal antibody preparation. A full-length AS3 protein can be used or, alternatively, the invention provides antigenic peptide fragments of AS3 for use as immunogens. The antigenic peptide of AS3 comprises at least 8 amino acid residues of the amino acid sequence shown in SEQ ID NO:2 and encompasses an epitope of AS3 such that an antibody raised against the peptide forms a specific immune complex with AS3. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of AS3 that are located on the surface of the protein, e.g., hydrophilic regions, as well as regions with high antigenicity (see, for example, FIG. 2).

An AS3 immunogen typically is used to prepare antibodies by immunizing a suitable subject, (e.g., rabbit, goat, mouse or other mammal) with the immunogen. An appropriate immunogenic preparation can contain, for example, recombinantly expressed AS3 protein or a chemically synthesized AS3 polypeptide. The preparation can further include an adjuvant, such as Freund's complete or incomplete adjuvant, or similar immunostimulatory agent. Immunization of a suitable subject with an immunogenic AS3 preparation induces a polyclonal anti-AS3 antibody response.

Accordingly, another aspect of the invention pertains to anti-AS3 antibodies. The term "antibody" as used herein refers to immunoglobulin molecules and immunologically active portions of immunoglobulin molecules, i.e., molecules that contain an antigen binding site which specifically binds (immunoreacts with) an antigen, such as AS3. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind AS3. The term "monoclonal antibody" or "monoclonal antibody composition", as used herein, refers to a population of antibody molecules that contain only one species of an antigen binding site capable of immunoreacting with a particular epitope of AS3. A monoclonal antibody composition thus typically displays a single binding affinity for a particular AS3 protein with which it immunoreacts.

Polyclonal anti-AS3 antibodies can be prepared as described above by immunizing a suitable subject with an AS3 immunogen. The anti-AS3 antibody titer in the immunized subject can be monitored over time by standard techniques, such as with an enzyme linked immunosorbent assay (ELISA) using immobilized AS3. If desired, the antibody molecules directed against AS3 can be isolated from the mammal (e.g., from the blood) and further purified by well known techniques, such as protein A chromatography to obtain the IgG fraction. At an appropriate time after immunization, e.g., when the anti-AS3 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with an AS3 immunogen as described above, and the culture supernatants of the resulting hybridoma cells are screened to identify a hybridoma producing a monoclonal antibody that binds AS3.

Any of the many well known protocols used for fusing lymphocytes and immortalized cell lines can be applied for the purpose of generating an anti-AS3 monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind AS3, e.g., using a standard ELISA assay.

Alternative to preparing monoclonal antibody-secreting hybridomas, a monoclonal anti-AS3 antibody can be identified and isolated by screening a recombinant combinatorial immunoglobulin library (e.g., an antibody phage display library) with AS3 to thereby isolate immunoglobulin library members that bind AS3. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226: 889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-AS3 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyan et al. (1988) *Science* 239:1534; and Beidler et al. (1988) *J. Immunol.* 141:4053–4060.

An anti-AS3 antibody (e.g., monoclonal antibody) can be used to isolate AS3 by standard techniques, such as affinity chromatography or immunoprecipitation. An anti-AS3 antibody can facilitate the purification of natural AS3 from cells and of recombinantly produced AS3 expressed in host cells. Moreover, an anti-AS3 antibody can be used to detect AS3 protein (e.g., in a cellular lysate or cell supernatant) in order to evaluate the abundance and pattern of expression of the AS3 protein. Anti-AS3 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

IV. Recombinant Expression Vectors

Another aspect of the invention pertains to vectors, preferably expression vectors, containing a nucleic acid encoding an AS3 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., AS3 proteins, mutant forms of AS3 proteins, fusion proteins, and the like).

The recombinant expression vectors of the invention can be designed for expression of AS3 proteins in prokaryotic or eukaryotic cells. For example, AS3 proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in AS3 activity assays, (e.g., direct assays or competitive assays described in detail below), or to generate antibodies specific for AS3 proteins, for example. In a preferred embodiment, an AS3 fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the AS3 expression vector is a yeast expression vector. Examples of vectors for expression in yeast *S. cerivisae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, AS3 proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the prostate specific promoter (Gotoh et al. (1998) *J. Urol.* 60:220–229) albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for transcription (by transcription of the DNA molecule) of an RNA molecule which is antisense to AS3 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

V. Host Cells

Another aspect of the invention pertains to host cells into which an AS3 nucleic acid molecule of the invention is introduced, e.g., an AS3 nucleic acid molecule within a recombinant expression vector or an AS3 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an AS3 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an AS3 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an AS3 protein. Accordingly, the invention further provides methods for producing an AS3 protein using the host cells of the invention. In one embodiment, the method comprises culturing the host cell of the invention (into which a recombinant expression vector encoding an AS3 protein has been introduced) in a suitable medium such that an AS3 protein is produced. In another embodiment, the method further comprises isolating an AS3 protein from the medium or the host cell.

VI. Transgenic Animals

The host cells of the invention can also be used to produce non-human transgenic animals. For example, in one embodiment, a host cell of the invention is a fertilized oocyte or an embryonic stem cell into which AS3-coding sequences have been introduced. Such host cells can then be used to create non-human transgenic animals in which exogenous AS3 sequences have been introduced into their genome or homologous recombinant animals in which endogenous AS3 sequences have been altered. Such animals are useful for studying the function and/or activity of an AS3 and for identifying and/or evaluating modulators of AS3 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous AS3 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing an AS3-encoding nucleic acid into the male pronuclei of a fertilized oocyte, e.g., by microinjection, retroviral infection, and allowing the oocyte to develop in a pseudopregnant female foster animal. The AS3 cDNA sequence of SEQ ID NO:1 can be introduced as a transgene into the genome of a non-human animal. Alternatively, a nonhuman homologue of a human AS3 gene, such as a mouse or rat AS3 gene, can be used as a transgene. Alternatively, an AS3 gene homologue, such as another AS3 family member, can be isolated based on hybridization to the AS3 cDNA sequences of SEQ ID NO:1 or 3 (described further in subsection I above) and used as a transgene. Intronic sequences and polyadenylation signals can also be included in the transgene to increase the efficiency of expression of the transgene. A tissue-specific regulatory sequence(s) can be operably linked to an AS3 transgene to direct expression of an AS3 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of an AS3 transgene in its genome and/or expression of AS3 mRNA in tissues or cells of the animals. A transgenic founder animal can then be used to breed additional animals carrying the transgene. Moreover, transgenic animals carrying a transgene encoding an AS3 protein can further be bred to other transgenic animals carrying other transgenes.

To create a homologous recombinant animal, a vector is prepared which contains at least a portion of an AS3 gene into which a deletion, addition or substitution has been introduced to thereby alter, e.g., functionally disrupt, the AS3 gene. The AS3 gene can be a human gene (e.g., the cDNA of SEQ ID NO:3), but more preferably, is a non-human homologue of a human AS3 gene (e.g., a cDNA isolated by stringent hybridization with the nucleotide sequence of SEQ ID NO:1). For example, a mouse AS3 gene can be used to construct a homologous recombination nucleic acid molecule, e.g., a vector, suitable for altering an endogenous AS3 gene in the mouse genome. In a preferred embodiment, the homologous recombination nucleic acid molecule is designed such that, upon homologous recombination, the endogenous AS3 gene is functionally disrupted (i.e., no longer encodes a functional protein; also referred to as a "knock out" vector). Alternatively, the homologous recombination nucleic acid molecule can be designed such that, upon homologous recombination, the endogenous AS3 gene is mutated or otherwise altered but still encodes functional protein (e.g., the upstream regulatory region can be altered to thereby alter the expression of the endogenous AS3 protein). In the homologous recombination nucleic acid molecule, the altered portion of the AS3 gene is flanked at its 5' and 3' ends by additional nucleic acid sequence of the AS3 gene to allow for homologous recombination to occur between the exogenous AS3 gene carried by the homologous recombination nucleic acid molecule and an endogenous AS3 gene in a cell, e.g., an embryonic stem cell. The additional flanking AS3 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced AS3 gene has homologously recombined with the endogenous AS3 gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

VII. Pharmaceutical Compositions

The AS3 nucleic acid molecules, fragments of AS3 proteins, and anti-AS3 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of an AS3 protein or an anti-AS3 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

VIII. Gene Therapy

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

IX. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, an AS3 protein of the invention modulates the arrest of cell proliferation, preferably hormone-mediated cell proliferation.

Thus, the isolated nucleic acid molecules of the invention can be used, for example, to express AS3 protein (e.g., via a recombinant expression vector in a host cell in gene therapy applications), to detect AS3 mRNA (e.g., in a biological sample) or a genetic alteration in an AS3 gene, and to modulate AS3 activity, as described further below. The AS3 nucleic acid molecules can be used to treat disorders characterized by insufficient production of AS3. The AS3 proteins can be used to screen for naturally occurring AS3 substrates, to screen for drugs or compounds which modulate AS3 activity, as well as to treat disorders characterized by insufficient production of AS3 protein or production of AS3 protein forms which have decreased, aberrant or unwanted activity compared to AS3 wild type protein (e.g., excessive cell proliferation). Moreover, the anti-AS3 antibodies of the invention can be used to detect and isolate AS3 proteins, regulate the bioavailability of AS3 proteins, and modulate AS3 activity.

IX, A, Screening Assays

The invention provides a method (also referred to herein as a "screening assay") for identifying modulators, i.e., candidate or test compounds or agents (e.g., peptides, peptidomimetics, small molecules or other drugs) which bind to AS3 proteins, have a stimulatory or inhibitory effect on, for example, AS3 expression or AS3 activity, or have a stimulatory or inhibitory effect on, for example, the expression or activity of AS3 substrate.

In one embodiment, the invention provides assays for screening candidate or test compounds which are substrates of an AS3 protein or polypeptide or biologically active portion thereof. In another embodiment, the invention provides assays for screening candidate or test compounds which bind to or modulate the activity of an AS3 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991)*J. Mol. Biol.* 222:301–310); (Ladner supra.).

In one embodiment, an assay is a cell-based assay in which a cell which expresses an AS3 protein or biologically active portion thereof is contacted with a test compound and the ability of the test compound to modulate AS3 activity is determined. Determining the ability of the test compound to modulate AS3 activity can be determined by monitoring, for example, changes in cell using standard techniques.

In another embodiment, an assay of the present invention is a cell-free assay in which an AS3 protein or biologically active portion thereof is contacted with a test compound and the ability of the test compound to bind to the AS3 protein or biologically active portion thereof is determined. Preferred biologically active portions of the AS3 proteins to be used in assays of the present invention include fragments which participate in interactions with non-AS3 molecules, e.g., fragments with high surface probability scores (see, for example, FIG. 2). Binding of the test compound to the AS3 protein can be determined either directly or indirectly as described above. In a preferred embodiment, the assay includes contacting the AS3 protein or biologically active portion thereof with a known compound which binds AS3 to form an assay mixture, contacting the assay mixture with a test compound, and determining the ability of the test compound to interact with an AS3 protein, wherein determining the ability of the test compound to interact with an AS3 protein comprises determining the ability of the test compound to preferentially bind to AS3 or biologically active portion thereof as compared to the known compound.

In yet another embodiment, the cell-free assay involves contacting an AS3 protein or biologically active portion thereof with a known compound which binds the AS3 protein to form an assay mixture, contacting the assay mixture with a test compound, and determining the ability of the test compound to interact with the AS3 protein, wherein determining the ability of the test compound to interact with the AS3 protein comprises determining the ability of the AS3 protein to preferentially bind to or modulate the activity of an AS3 target molecule.

In more than one embodiment of the above assay methods of the present invention, it may be desirable to immobilize AS3 to facilitate separation of proteins that interact with AS3, as well as to accommodate automation of the assay. Binding of a test compound to an AS3 protein, or interaction of an AS3 protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/AS3 fusion proteins or glutathione-5-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or AS3 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of AS3 binding or activity determined using standard techniques.

Other techniques for immobilizing proteins on matrices can also be used in the screening assays of the invention. For example, either an AS3 protein or an AS3 target molecule can be immobilized utilizing conjugation of biotin and streptavidin. Biotinylated AS3 protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with AS3 protein or target molecules but which do not interfere with binding of the AS3 protein to its target molecule can be derivatized to the wells of the plate, and unbound target or AS3 protein trapped in the wells by antibody conjugation. Methods for detecting such complexes, in addition to those described above for the GST-immobilized complexes, include immunodetection of complexes using antibodies reactive with the AS3 protein or target molecule, as well as enzyme-linked assays which rely on detecting an enzymatic activity associated with the AS3 protein or target molecule.

In another embodiment, modulators of AS3 expression are identified in a method wherein a cell is contacted with a candidate compound and the expression of AS3 mRNA or protein in the cell is determined. The level of expression of AS3 mRNA or protein in the presence of the candidate compound is compared to the level of expression of AS3 mRNA or protein in the absence of the candidate compound. The candidate compound can then be identified as a modulator of AS3 expression based on this comparison. For example, when expression of AS3 mRNA or protein is greater (statistically significantly greater) in the presence of the candidate compound than in its absence, the candidate compound is identified as a stimulator of AS3 mRNA or protein expression. Alternatively, when expression of AS3 mRNA or protein is less (statistically significantly less) in the presence of the candidate compound than in its absence, the candidate compound is identified as an inhibitor of AS3 mRNA or protein expression. This assay may be further modified to include the presence of a hormone, e.g., an androgen or an anti-androgen. The level of AS3 mRNA or protein expression in the cells can be determined by methods described herein for detecting AS3 mRNA or protein.

In yet another aspect of the invention, the AS3 proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with AS3 ("AS3-binding proteins" or "AS3-bp") and are involved in AS3 activity. Such AS3-binding proteins are also likely to be involved in the propagation of signals by the AS3 proteins or AS3 targets as, for example, downstream elements of an AS3-mediated signaling pathway. Alternatively, such AS3-binding proteins are likely to be AS3 inhibitors.

The two-hybrid system is based on the modular nature of most transcription factors, which consist of separable DNA-binding and activation domains. Briefly, the assay utilizes two different DNA constructs. In one construct, the gene that codes for an AS3 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an AS3-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the AS3 protein.

In another aspect, the invention pertains to a combination of two or more of the assays described herein. For example, a modulating agent can be identified using a cell-based or a cell free assay, and the ability of the agent to modulate the activity of an AS3 protein can be confirmed in vivo, e.g., in an animal such as an animal model for pain.

This invention further pertains to novel agents identified by the above-described screening assays. Accordingly, it is within the scope of this invention to further use an agent identified as described herein in an appropriate animal model. For example, an agent identified as described herein (e.g., an AS3 modulating agent, an antisense AS3 nucleic acid molecule, an AS3-specific antibody, or an AS3-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

IX, B, Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

IX, B, 1., Chromosome Mapping

Once the sequence (or a portion of the sequence) of a gene has been isolated, this sequence can be used to map the location of the gene on a chromosome. This process is called chromosome mapping. Accordingly, portions or fragments of the AS3 nucleotide sequences, described herein, can be used to map the location of the AS3 genes on a chromosome as described in Example 4. The mapping of the AS3 sequences to chromosomes is an important step in correlating these sequences with genes associated with disease.

Moreover, differences in the DNA sequences between individuals affected and unaffected with a disease associated with the AS3 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

IX, B, 2., Tissue Typing

The AS3 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the AS3 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The AS3 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from AS3 nucleotide sequences described herein is used to generate a unique identification database for an individual, those same reagents can later be used to identify tissue from that individual. Using the unique identification database, positive identification of the individual, living or dead, can be made from extremely small tissue samples.

IX, B, 3., Use of Partial AS3 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the AS3 nucleotide sequences or portions thereof, e.g., fragments derived from the noncoding regions of SEQ ID NO:1 having a length of at least 20 bases, preferably at least 30 bases.

The AS3 nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such AS3 probes can be used to identify tissue by species and/or by organ type.

In a similar fashion, these reagents, e.g., AS3 primers or probes can be used to screen tissue culture for contamination (i.e. screen for the presence of a mixture of different types of cells in a culture).

IX, C, Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining AS3 protein and/or nucleic acid expression as well as AS3 activity, in the context of a biological sample (e.g., blood, serum, cells, tissue) to thereby determine whether an individual is afflicted with a disease or disorder, or is at risk of developing a disorder, associated with aberrant or reduced AS3 expression or activity. The invention also provides for prognostic (or predictive) assays for determining whether an individual is at risk of developing a disorder associated with AS3 protein, nucleic acid expression or activity. For example, mutations in an AS3 gene can be assayed in a biological sample. Such assays can be used for prognostic or predictive purpose to thereby prophylactically treat an individual prior to the onset of a disorder characterized by or associated with AS3 protein, nucleic acid expression, or activity.

Another aspect of the invention pertains to monitoring the influence of agents (e.g., drugs, compounds) on the expression or activity of AS3 in clinical trials.

These and other agents are described in further detail in the following sections and in Examples 4 and 5.

IX, C, 1., Diagnostic Assays

An exemplary method for detecting the presence or absence of AS3 protein or nucleic acid in a biological sample involves obtaining a biological sample from a test subject and contacting the biological sample with a compound or an agent capable of detecting AS3 protein or nucleic acid (e.g., mRNA, genomic DNA) that encodes AS3 protein such that the presence of AS3 protein or nucleic acid is detected in the biological sample. A preferred agent for detecting AS3 mRNA or genomic DNA is a labeled nucleic acid probe capable of hybridizing to AS3 mRNA or genomic DNA. The nucleic acid probe can be, for example, a full-length AS3 nucleic acid, such as the nucleic acid of SEQ ID NO:1 or 3, or a portion thereof, such as an oligonucleotide of at least 15, 30, 50, 100, 250 or 500 nucleotides in length and sufficient to specifically hybridize under stringent conditions to AS3 mRNA or genomic DNA. Other suitable probes for use in the diagnostic assays of the invention are described herein.

A preferred agent for detecting AS3 protein is an antibody capable of binding to AS3 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect AS3 mRNA, protein, or genomic DNA in a biological sample in vitro as well as in vivo. For example, in vitro techniques for detection of AS3 mRNA include Northern hybridizations and in situ hybridizations. In vitro techniques for detection of AS3 protein include enzyme linked immunosorbent assays (ELISAs), Western blots, immunoprecipitations and immunofluorescence. In vitro techniques for detection of AS3 genomic DNA include Southern hybridizations.

In one embodiment, the biological sample contains protein molecules from the test subject. Alternatively, the biological sample can contain mRNA molecules from the test subject or genomic. DNA molecules from the test subject. A preferred biological sample is a tissue or cell sample isolated by conventional means from a subject.

In another embodiment, the methods further involve obtaining a control biological sample from a control subject, contacting the control sample with a compound or agent capable of detecting AS3 protein, mRNA, or genomic DNA, such that the presence of AS3 protein, mRNA or genomic DNA is detected in the biological sample, and comparing the presence of AS3 protein, mRNA or genomic DNA in the control sample with the presence of AS3 protein, mRNA or genomic DNA in the test sample.

The invention also encompasses kits for detecting the presence of AS3 in a biological sample. For example, the kit can comprise a labeled compound or agent capable of detecting AS3 protein or mRNA in a biological sample; means for determining the amount of AS3 in the sample; and means for comparing the amount of AS3 in the sample with a standard. The compound or agent can be packaged in a suitable container. The kit can further comprise instructions for using the kit to detect AS3 protein or nucleic acid.

IX, C, 2., Prognostic Assays

The diagnostic methods described herein can furthermore be utilized to identify subjects having or at risk of developing a disease or disorder associated with aberrant AS3 expression or activity. As used herein, the term "aberrant" includes an AS3 expression or activity which deviates from the wild type AS3 expression or activity. Aberrant expression or activity includes increased or decreased expression or activity, as well as expression or activity which does not follow the wild type developmental pattern of expression or the subcellular pattern of expression. For example, aberrant AS3 expression or activity is intended to include the cases in which a mutation in the AS3 gene causes the AS3 gene to be under-expressed or over-expressed and situations in which such mutations result in a non-functional AS3 protein or a protein which does not function in a wild-type fashion, e.g., a protein which does not interact with an AS3 ligand or one which interacts with a non-AS3 ligand.

The assays described herein, such as the preceding diagnostic assays or the following assays, can be utilized to identify a subject having or at risk of developing a malignancy associated with a misregulation in AS3 protein activity or nucleic acid expression, such as a prostate cancer. Thus, the present invention provides a method for identifying a disease- or disorder associated with aberrant AS3 expression or activity in which a test sample is obtained from a subject and AS3 protein or nucleic acid (e.g., mRNA or genomic DNA) is detected, wherein the presence of AS3 protein or nucleic acid is diagnostic for a subject having or at risk of developing a disease or disorder associated with aberrant or unwanted AS3 expression or activity. As used herein, a "test sample" refers to a biological sample obtained from a subject of interest. For example, a test sample can be a cell, tissue, or biological fluid containing a cell.

Furthermore, the prognostic assays described herein can be used to determine whether a subject can be administered an agent (e.g., an agonist, antagonist, peptidomimetic, protein, peptide, nucleic acid, small molecule, or other drug candidate, such as a hormone, e.g., an androgen) to treat a disease or disorder associated with aberrant AS3 expression or activity. For example, such methods can be used to determine whether a subject can be effectively treated with an agent for aberrant cell proliferation, e.g., cancer of the prostate.

The methods of the invention can also be used to detect genetic alterations in an AS3 gene, thereby determining if a subject with the altered gene is at risk for a disorder characterized by misregulation in AS3 protein activity or nucleic acid expression, such as a proliferative disorder, e.g., cancer. In preferred embodiments, the methods include detecting, in a sample of cells from the subject, the presence or absence of a genetic alteration characterized by at least one of an alteration affecting the integrity of a gene encoding an AS3-protein, or the mis-expression of the AS3 gene. For example, such genetic alterations can be detected by ascertaining the existence of at least one of 1) a deletion of one or more nucleotides from an AS3 gene; 2) an addition of one or more nucleotides to an AS3 gene; 3) a substitution of one or more nucleotides of an AS3 gene, 4) a chromosomal rearrangement of an AS3 gene; 5) an alteration in the level of a messenger RNA transcript of an AS3 gene, 6) aberrant modification of an AS3 gene, such as of the methylation pattern of the genomic DNA, 7) the presence of a non-wild type splicing pattern of a messenger RNA transcript of an AS3 gene, 8) a non-wild type level of an AS3-protein, 9) allelic loss of an AS3 gene, and 10) inappropriate post-translational modification of an AS3-protein. As described herein, there are a large number of assays known in the art which can be used for detecting alterations in an AS3 gene. A preferred biological sample is a cell, tissue, or biological fluid containing a cell, isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the AS3-gene (see Abravaya et al. (1995) *Nucleic Acids Res* 0.23:675–682). This method can include the steps of collecting a sample of cells from a subject, isolating nucleic acid (e.g., genomic, mRNA or both) from the cells of the sample, contacting the nucleic acid sample with one or more primers which specifically hybridize to an AS3 gene under conditions such that hybridization and amplification of the AS3-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an AS3 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in AS3 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in AS3 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the AS3 gene and detect mutations by comparing the sequence of the sample AS3 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993)*Appl. Biochem. Biotechnol.* 38:147–159).

Other methods for detecting mutations in the AS3 gene include methods in which protection from cleavage agents is used to detect mismatched bases in RNA/RNA or RNA/DNA heteroduplexes (Myers et al. (1985) *Science* 230: 1242). In general, the art technique of "mismatch cleavage" starts by providing heteroduplexes of formed by hybridizing (labeled) RNA or DNA containing the wild-type AS3 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNAse and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in AS3 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on an AS3 sequence, e.g., a wild-type AS3 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in AS3 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control AS3 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an AS3 gene.

Furthermore, any cell type or tissue in which AS3 is expressed, e.g., prostate tissue, may be utilized in the prognostic assays described herein.

IX, C, 3., Monitoring of Effects During Clinical Trials

Monitoring the influence of agents (e.g., hormone therapy) on the expression or activity of an AS3 protein (e.g., the modulation of cell proliferation) can be applied not only in basic drug screening, but also in clinical trials. For example, the effectiveness of an agent determined by a screening assay as described herein to increase AS3 gene expression, protein levels, or upregulate AS3 activity, can be monitored in clinical trials of subjects exhibiting decreased AS3 gene expression, protein levels, or downregulated AS3 activity. Alternatively, the effectiveness of an agent determined by a screening assay to decrease AS3 gene expression, protein levels, or downregulate AS3 activity, can be monitored in clinical trials of subjects exhibiting increased AS3 gene expression, protein levels, or upregulated AS3 activity. In such clinical trials, the expression or activity of an AS3 gene, and preferably, other genes (e.g., prostate-specific antigen (PSA)) that have been implicated in, for example, an AS3-associated disorder can be used as a "read out" or markers of the phenotype of a particular cell.

For example, and not by way of limitation, genes, including AS3, that are modulated in cells by treatment with an agent (e.g., compound, drug or hormone) which modulates AS3 activity (e.g., identified in a screening assay as described herein) can be identified. Thus, to study the effect of agents on cell proliferation modulated by AS3, for example, in a clinical trial, cells can be isolated and RNA prepared and analyzed for the levels of expression of AS3 and other genes implicated in the AS3-associated disorder. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of AS3 or other genes. In this way, the gene expression pattern can serve as a marker, indicative of the physiological response of the cells to the agent. Accordingly, this response state may be determined before, and at various points during treatment of the individual with the agent or may be used to determine when treatment is appropriate.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate, e.g., a hormone, identified by the screening assays described herein) including the steps of (i) obtaining a pre-administration sample from a subject prior to administration of the agent; (ii) detecting the level of expression of an AS3 protein, mRNA, or genomic DNA in the preadministration sample; (iii) obtaining one or more post-administration samples from the subject; (iv) detecting the level of expression or activity of the AS3 protein, mRNA, or genomic DNA in the post-administration samples; (v) comparing the level of expression or activity of the AS3 protein, mRNA, or genomic DNA in the pre-administration sample with the AS3 protein, mRNA, or genomic DNA in the post administration sample or samples; and (vi) altering the administration of the agent to the subject accordingly. For example, increased administration of the agent may be desirable to increase the expression or activity of AS3 to higher levels than detected, i.e., to increase the effectiveness of the agent. Alternatively, decreased administration of the agent may be desirable to decrease expression or activity of AS3 to lower levels than detected, i.e. to decrease the effectiveness of the agent. According to such an embodiment, AS3 expression or activity may be used as an indicator of the effectiveness of an agent, even in the absence of an observable phenotypic response.

IX, D., Methods of Treatment

The present invention provides for both prophylactic and therapeutic methods of treating a subject at risk of (or susceptible to) a disorder or having a disorder associated with aberrant AS3 expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the AS3 molecules of the present invention or AS3 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

IX, D., 1., Prophylactic Methods

In one aspect, the invention provides a method for preventing in a subject, a disease or condition associated with an aberrant AS3 expression or activity, by administering to the subject an AS3 molecule or an agent which modulates AS3 expression or at least AS3 activity. Subjects at risk for a disease (e.g., prostate cancer) which is caused or contributed to by aberrant AS3 expression or activity can be identified by, for example, any or a combination of diagnostic or prognostic assays as described herein. Administration of a prophylactic agent can occur prior to the manifestation of symptoms characteristic of the AS3 aberrancy, such that a disease or disorder is prevented or, alternatively, delayed in its progression. Depending on the type of AS3 aberrancy, for example, an AS3 molecule, AS3 agonist (e.g., hormone therapy), or AS3 antagonist agent can be used for treating the subject. The appropriate agent can be determined based on screening assays described herein.

IX, D., 2., Therapeutic Methods

Another aspect of the invention pertains to methods of modulating AS3 expression or activity for therapeutic purposes. Accordingly, in an exemplary embodiment, the modulatory method of the invention involves contacting a cell with an AS3 molecule or agent that modulates AS3 protein activity associated with cell (e.g., cell proliferation). An agent that modulates AS3 protein activity can be an agent as described herein, such as a nucleic acid or a protein, a naturally-occurring target molecule of an AS3 protein (e.g., an AS3 substrate), an AS3 antibody, an AS3 agonist or antagonist, a peptidomimetic of an AS3 agonist or antagonist, or other small molecule (e.g., hormone, such as an androgen). In one embodiment, the agent stimulates one or more AS3 activities. Examples of such stimulatory agents include androgen therapy or a nucleic acid molecule encoding AS3 that has been introduced into the cell. These modulatory methods can be performed in vitro (e.g., by culturing the cell with the agent) or, alternatively, in vivo (e.g., by administering the agent to a subject). As such, the present invention provides methods of treating an individual afflicted with a cell proliferative disease (e.g., prostate cancer) or disorder characterized by aberrant or reduced expression or activity of an AS3 protein or nucleic acid molecule. In one embodiment, the method involves administering an agent (e.g., an agent identified by a screening assay or a hormone such as androgen as described herein), or combination of agents that modulates AS3 expression or activity.

Stimulation of AS3 activity is desirable in situations in which AS3 is abnormally downregulated and/or in which increased AS3 activity is likely to have a beneficial effect. For example, stimulation of AS3 activity is desirable in a cell proliferative disease such as prostate cancer and increasing AS3 activity is likely to have a beneficial effect. Moreover, the ability to detect androgen-induced AS3 expression in a patient is an indication that the patient is responsive to hormone and therefore a candidate for intermittent hormone therapy. As used herein, the term "intermittent hormone therapy" or "intermittent hormone treatment" includes a treatment regime wherein a patient is treated with a hormone, such as an androgen, for a period of time and then withdrawn from such treatment for a period of time. This intermittent administration of hormone shall be, at least in part, determined by an analysis of the patients AS3 levels as described herein.

IX, D, 3., Pharmacogenomics

The AS3 molecules of the present invention, as well as agents, or modulators which have a stimulatory or inhibitory effect on AS3 activity (e.g., AS3 gene expression) as identified by a screening assay described herein can be administered to individuals to treat (prophylactically or therapeutically) AS3-associated disorders (e.g., cell proliferation) associated with aberrant or reduced AS3 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an AS3 molecule or AS3 modulator as well as tailoring the dosage and/or therapeutic regimen of treatment with an AS3 molecule or AS3 modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10–11) :983–985 and Linder, M. W. et al. (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., an AS3 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C 19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., an AS3 molecule or AS3 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with an AS3 molecule or AS3 modulator, such as a modulator identified by one of the exemplary screening assays described herein.

This invention is further illustrated by the following examples which should not be construed as limiting. The contents of all references, patents and published patent applications cited throughout this application are incorporated herein by reference.

EXAMPLE 1

Isolation and Cloning of Human AS3

In this example, the isolation and cloning of the gene encoding human AS3 is described.

To isolate a cDNA encoding an inhibitor of prostate cancer progression, the LNCaP-FGC cell line established from a metastatic lymph node from a patient with prostate adenocarcinoma (Horoszewicz et al., (1983) *Cancer Res.* 43:1809–1818) was utilized. This cell line and related cell lines derived therefrom were cultured as previously described (Soto et al., (1995) *Oncology Res.* 7: 545–558; Soto et al., (1991) *J. Steroid Biochem.* 23: 87–94).

In addition, to isolate a gene expressed at the proliferative shutoff point (i.e., Step 2), a subtractive strategy was used whereby the proliferation of LNCaP-FGC cells was arrested using two different treatments, namely, CD serum (i.e., androgen free serum) and high androgen concentrations. This selective approach takes advantage of the fact that the cells were equally arrested at the G1 stage of the cell cycle by different mechanisms (Soto et al., (1995) *Oncology Res.* 7: 545–558).

Moreover, since regulatory mRNAs are frequently expressed at low copy numbers, a protocol was adopted using repeated PCR cycles to selectively amplify these sequences. The final subtracted pool, therefore, was enriched to represent high ranking regulatory elements in the androgen-induced proliferative shutoff (Step-2).

Briefly, androgen-specific, low-abundance regulatory mRNA sequences expressed during the proliferative shutoff, were selected using the Wang-Brown approach (Wang et al., (1991) *Proc. Natl. Acad. Sci. USA* 88: 11505–11509). Short fragments of cDNAs were amplified first: then three cycles of subtractions and amplifications between the control and proliferation arrested cDNAs resulted in sequence pools that were differentially expressed (Geck et al., (1997) *J. Steroid Biochem. Mol. Biol.* 63: 211–218). LNCaP-FGC cells were treated with 30 nM R1881 to generate proliferative shutoff. R1881 (methyltrienolone) is a synthetic, non-metabolized androgen (Roussell-UCLAF, Romainville, France). Exposure to androgen for 24 hours was required to commit LNCaP-FGC cells to an irreversible proliferative shutoff (Geck et al., (1997) *J. Steroid Biochem. Mol. Biol.* 63: 211–218). It was concluded that at this point, the genes responsible for the shutoff were highly induced. LNCaP-FGC cells reversibly arrested by CDHuS were considered as the shutoff-negative control; they were harvested after three days of CDHuS treatment. Total RNA was prepared by the acidic guanidinium-thiocyanate method and polyA RNA was purified by using the FastTrack™ kit (Invitrogen, San Diego, Calif.) (Chomczinsky et al., (1987) *Anal. Biochem.* 162: 156–159).

Double-stranded cDNA pools from R1881-treated cells (R cDNA) and CDHuS-treated cells (CD cDNA) were synthesized using the Copy Kit™ (Invitrogen), with oligo-dT priming. After AluI and RsaI digestions and adaptor ligations, the constructs were PCR-amplified (GeneAmp Kit™, Perkin Elmer, Foster City, Calif.). The amplified CD cDNA were digested with Eco RI, photobiotinylated (driver cDNA) and hybridized at 20-fold molar excess to an aliquot of non-biotinylated R cDNA. The hybridized non-specific sequences were eliminated by subsequent Streptavidin chromatography. After 3 cycles of selection, the amplified expressed sequence tag (EST) pool of the androgen-induced shutoff AS (R cDNA pool minus CD cDNA pool) sequences was digested with EcoRI, cloned into the BlueScript SK™ vector (Stratagene, La Jolla, Calif.) and transformed into *E. coli* (OneShot™ strain, Invitrogen).

Isolation of unique cDNAs from the differentially expressed sequence pool was performed as follows. Recombinants were collected randomly from the shutoff-positive AS pool of the Wang-Brown differential library and were plated. Using the labeled CD- and R-subtracted (CD cDNA pool minus R cDNA pool), PCR-amplified DNA master mixes as probes, double hybridizations revealed 11 and 14 clones that were present exclusively in the CD and R clone sets, respectively (Geck et al., (1997) *J. Steroid Biochem. Mol. Biol.* 63: 211–218). Multiple cross-hybridizations identified ten unique inserts.

To sequence the identified EST fragments, PCR sequencing reactions were performed using the dsDNA Sequencing System™ (Life Technologies, Gaithersburg, Md.). The EST DNA sequences were tested for homology to known DNA sequences using the FASTA and BLAST (National Center for Biotechnology Information, Bethesda, Md.) programs. Five inserts were found with no match in GenBank (Geck et al., (1997) *J. Steroid Biochem. Mol. Biol.* 63: 211–218). For further analysis, the mRNA with the highest induction in shutoff positive LNCaP-FGC cells (AS3, >5–6-fold of the 5.3 kb mRNA, and >3–4-fold of the 8 kb isoform) was selected.

To isolate the full length AS3 cDNA sequence, a 262 bp AS3 tag sequence was utilized to design nested primer pairs to amplify the full length cDNA sequence from a cDNA library. The cDNA libraries were generated by Human Genome Sciences (Rockville, Md.), using polyA+ mRNA preparations from androgen-treated or CDHuS-treated proliferation-arrested LNCaP-FGC cells. The Lambda ZAPII (UniZAP) phage was used as vector carrying EcoRI and XhoI cloning sites. The PCR reaction was designed to amplify the cloned unknown cDNA segments between the known tag sequence and the flanking vector sequences. Since the orientation of the tag sequence was not known, both ends of the insert were amplified in both directions. The vector primers used were commercially available sequencing primers: M13 Reverse and T3 primers at the EcoRI site, and M13–20 and T7 primers at the XhoI site.

For the PCR reaction, the Expand High Fidelity™ kit was used and a 1 µl phage suspension as template (Boehringer-Mannheim). A 40 cycle amplification in a Perkin-Elmer 9600 thermocycler resulted in the production of a 1370 bp 5' fragment and a 3250 bp 3' fragment. These PCR products were purified using Qiagen columns, and sequenced by automatic sequencing using a primer walking strategy. The sequencing data showed that the open reading frame in the 5' end fragment did not have an authentic AUG codon.

To search for the missing 5' end of the transcript, the Prostate Specific Marathon Ready cDNA™ preparation from Clontech was used. Amplifications with the Clontech anchored primer and a set of AS3 specific primers resulted in a 419 bp fragment. The DNA was cloned and sequencing data showed that it carried the N-terminal 118 amino acids of the open reading frame. The nucleotide sequence reported herein has been submitted to GenBank under the accession number U95825 (see also, Geck et al., (1999) *J. Steriod Biochem. Mol. Biol.* 68:41–50).

EXAMPLE 2

Characterization of the AS3 cDNA Sequence

In this example, the features of the AS3 mRNA and cDNA sequences are described. Computer analysis of the sequenced 5253 bp AS3 cDNA identified a long open reading frame (FIG. 1). The initiator methionine is at position 66, the stop codon was found at position 4239, and the region codes for a polypeptide of 1391 residues. The initiator is the first AUG codon downstream from the 5' end of the sequence, and appears in a strong Kozak-context (Kozak, (1991)*J. Biol. Chem.* 266:19867–19870; Kozak, (1991)*J. Cell Biol.* 115:887–903). The Northern blot size of the transcript is between 5.3 and 5.5 kb (Geck et al., (1997) *J. Steroid Biochem. Mol. Biol.* 63: 211–218) and since the sequence reported here has 5253 nucleotides plus the poly-A tail, the 5' end of our sequence is at or within a few nucleotides of the 5' physical end, further suggesting that the initiator is authentic. The 5' non-coding region is high in GC nucleotides (63.3%), but it has no recognizable secondary structure elements or other sequence features. The 3' non-coding region has several destabilizing AT-rich elements (underlined in FIG. 1), typical of transcripts claimed to play a role in cell proliferation (Shaw et al., (1986) *Cell* 46:659–667, Chen et al., (1995) *Trends Biochem. Sci.* 20:465–470). The polyadenylation signal of the transcript is 25 bp upstream of the consensus GT-rich cleavage site (indicated in a larger font in FIG. 1).

EXAMPLE 3

Characterization of the AS3 Polypeptide Sequence

In this example, various structural and functional features of the AS3 polypeptide are described.

Computer analysis of the AS3 open reading frame was performed using the Translate program of the Wisconsin Package Version 9.0, Genetics Computer Group (GCG), Madison, Wis. β-strand and α-helix structures were calculated by the Chou-Fasman method using PepStructure and PepPlot programs. Motif and profile predictions were calculated using various programs of the Wisconsin Package, or by using remote servers offering sequence analyses of protein functional domains through the Internet. The following remote servers were used: PROWEB, available online at the Proweb Project website; BLOCKS, available online at the Blocks WWW Server; PRODOM, available online at the Prodom website; PRINTS, available online at the Prints website; and the Protein Kinase Resource, available online at the Protein Kinase Resource website.

Employing the above programs, the expected molecular weight of the AS3 polypeptide is determined as 186 kD. In addition, it's noted that the N-terminal 400 amino acid domain is characterized by a unique arrangement of 31 aliphatic residues (21 of them are leucines). Every seventh position (with minor variations) is occupied by a leucine or similar hydrophobic residues and in the five subdomains shown in FIG. 2, the pattern is uninterrupted. The arrangement is typical for coiled-coil structures where one side of the long α-helices is hydrophobic and usually participates in protein—protein interactions (Lupas, (1996) *Trends Biochem. Sci.* 22:375–382; Beavil et al., (1992) *Proc. Natl. Acad. Sci. USA* 89:753–757). The leucine-zipper motif of DNA binding proteins is a specific subclass of this general pattern and the subdomain between positions 196 and 217 in the AS3 sequence is a perfect leucine-zipper.

The AS3 polypeptide sequence between positions 400 and 600 has elements of a conserved Mg-ATP binding domain of various nucleotide triphosphate binding proteins including protein kinases. In FIG. 3, the AS3 sequence is shown in the conserved subdomain arrangements established by Hanks (Hanks et al., (1991) *Methods Enzymol.* 200:38–62). The conserved β-strand, α-helix structures and highly conserved critical residues are also indicated, together with the corresponding sequences of various protein kinases (Taylor et al., (1992) *Annu. Rev. Cell Biol.* 8:429–462). Although the complete AS3 sequence did not appear to be related to any particular protein kinase or ATP binding protein, partial homology within the subdomains was maintained, and probably indicates that the domain is functional. Indeed, one feature of the AS3 polypeptide is the presence of several relatively well conserved kinase-related domains such as an Mg-nucleotide triphosphate binding pocket, as well as elements of the catalytic domain of several protein kinases (see FIG. 3). Functional analysis of this domain using GST-fusion constructs indicates that the fusion construct polypeptide can form a complex resulting in the phosphorylation of at least two substrate proteins found in LNCaP-FGC cell extracts.

In addition to the above-mentioned motifs, the AS3 polypeptide also has a functional protein kinase domain located at amino acid residues 474–680 (encoded by nucleic acids 1420–2040; see SEQ ID NO: 3). To demonstrate that this region of the AS3 polypeptide has kinase activity, and is, e.g., capable of phosphorylating cellular substrates, the nucleic acid encoding this region was PCR amplified (using a corresponding upstream primer with a BamHI site and a corresponding downstream primer with a EcoRI site), digested, purified, and cloned into BamHI sites of the bacterial GST-fusion vector pGEX-T2 thereby fusing the AS3 domain to the C-terminus of GST (thus, the fusion protein is referred to as GST-AS3). The resultant construct, encoding a GST-AS3 fusion protein, was then transferred into bacteria (BL21 protease minus host) which were then induced to express the GST-AS3 fusion protein. Bacterial extracts containing the GST/AS3 fusion protein were incubated with MCF7-AR1 cell extracts in the presence of $^{32}$P-ATP and chromatographed through glutathione-Sepharose. Proteins which specifically bound to the GST-AS3 fusion protein were resolved by SDS-PAGE and autoradiography using standard conditions. Two polypeptides (40 and 120 kDa) were specifically purified and phosphorylated by the AS3-GST fusion protein demonstrating the functional kinase activity of this protein kinase domain of AS3. There was no $^{32}$P-labelled band observed at 90 kDa (the mass of the AS3-GTS fusion protein) suggesting that the AS3 kinase domain does not auto-phosphorylate but phosphorylates other proteins through, e.g., a docking mechanism.

Furthermore, a putative nuclear localization sequence (NLS) (KKFTQVLEDDEKIRK; SEQ ID NO: 6) resembling that of the androgen receptor and DNA polymerase-α was localized at position 547(Zhou et al., (1994) *J. Biol. Chem.* 269:13115–13123; Bouvier et al., (1995 *Mol. Biol. Cell* 6:1697–1705). Further, the C-terminal region of the putative AS3 polypeptide contains several sequence elements that show similarities to DNA binding proteins. Motifs and ProfileScan searches in the Wisconsin Package indicated helix-loop-helix and Homeo-box signature sequences in the area, and a remote search on the BLOCKS server also identified DNA binding block elements in the C-terminal sequences. Still further, it is noted a serine-rich domain at position 1139, and a proline/glycine-rich domain at the 1284 position were also found. The C-terminal domain (about 200 amino acids) is highly charged and arranged in unique repeats of seven alternating acidic and basic domains.

A BLASTP search performed on the GenBank database resulted in a single high score similarity with the bimD gene of the eukaryotic organism *Aspergillus nidulans*, where 50% of the amino acid sequence was functionally similar in portions of the coiled-coil domain and the putative DNA binding domain at the C-terminus. The bimD protein has a basic leucine-zipper and a C-terminal charged (acidic) domain, similar to AS3, and appears to function as a DNA binding protein (Denison et al., (1992) *Genetics,* 134:1085–1096). Both the AS3 and the bimD proteins also have nuclear localization consensus sequences.

Finally, to confirm that the AS3 polypeptide is capable of binding to DNA and moreover, to elucidate a DNA motif that binds to the DNA recognition sequence of AS3, an AS3-GST fusion polypeptide containing the DNA recognition sequence of AS3 was produced using a similar approach as used above to assay AS3 kinase activity.

Briefly, an expression vector was engineered to encode the DNA binding domain of AS3 fused to the N-terminus of GST (thus, the fusion protein is referred to as AS3-GST) which, when expressed in bacteria, allowed for the production of an AS3-GST fusion protein for DNA binding studies. The AS3-GST protein was then purified by affinity chromatography as described above. Next, the resultant, purified AS3-GST protein was incubated with a mixture of oligonucleotides comprising constant 5' (25 bp) and 3'(25 bp) ends and randomly generated middle segments (18 bp) and chromatographed through a glutathione-Sepharose the column. To avoid non-specific binding, double stranded poly (dI-dC) (average length 1800 bp) was added to the mixture. The AS3-GST fusion protein, together with bound oligonucleotides, was eluted with glutathione and the bound oligonucleotides were amplified by PCR, purified, and subjected to a second round of column chromatography using AS3-GST before being PCR amplified and cloned into a TA vector.

Thirty clones were sequenced to assess whether a specific nucleotide sequence was recognized by the AS3-GST fusion product. The sequences were compared and analyzed by the PILE-UP program of the GCG package. The co-alignment of the sequences revealed a pattern of the following putative consensus sequence:

5' C, T, A, [T/A], [T/A], A, G, [C/G], C, C, C, [C/G], G, C, [C/G]), C, A, [A/T], 3' (SEQ ID NO: 5)

Interestingly, sequence similarities were found between the putative AS3 DNA recognition sequence and the NF-kappaB and the Mbp1 recognition motifs. In addition, similarities within the p27$^{kir1}$ promoter at positions −270, −383, −427, and −586 were also found indicating that important gene regulatory elements exist in the cell in which the AS3 protein may interact with (Zhang et al., (1997) *Biochem. Biophys. Acta.,* 1353:307–317). Interestingly, the transcription factor NF-kappaB, which is involved in the control of apoptosis, and Mbp1 which is involved in the G1-S cell cycle transition in yeast, also interact with similar DNA motifs (Waddick et al., (1999) *Biochem. Pharmacol.,* 57:9–17; Koch et al., (1993) *Science,* 261:1551–1557).

Accordingly, it was concluded that AS3 is capable of binding to DNA in a sequence specific manner and therefore, may function as a transcriptional regulator of genes involved in cell growth control.

EXAMPLE 4

The AS3 Genomic Locus and Use of AS3 Related Molecules as Markers for Disease

In this example, aspects of the AS3 genomic locus and the use of AS3 related molecules as markers for disease are described.

A computer homology search in GenBank was performed and identified the AS3 genomic region as residing on chromosome 13q12–q13. This area is represented by cosmid 267p19, and on P1 artificial chromosomes PAC26H23 and PAC49J10. Consensus splicing donor and acceptor sites were identified and the entire exon-intron structure of the AS3 gene was resolved comparing the cDNA sequence and the genomic sequence using the BLAST program (see FIG. 4) (Shapiro et al., (1987) *Nucl. Acids Res.* 15:7155–7174). The actual cosmid and cDNA positions are listed in FIG. 4, and the arrangement of exons is depicted in FIG. 5. The area covers nearly 200,000 bp and the average size of the exons is 100–150 bp.

Interestingly, the AS3 genomic area is centromeric to the RB 1 locus, and telomeric to BRCA2. The AS3 gene is transcribed in the same direction as BRCA2, and the coding strand is downstream from the breast cancer gene (Couch et al., (1997) *Genomics* 36:86–99). On the opposite strand upstream of AS3, three regions were assigned to cDNAs of unknown functions. An expressed sequence (CG008) has been assigned to this area, and represents a portion of the AS3 transcript (Couch et al., (1997) *Genomics* 36:86–99).

The N terminal 354 amino acids of the open reading frame are missing in the CG008 sequence in GenBank. The CG008 open reading frame terminates at amino acid 738 of the AS3 sequence. The sequencing data reported herein and the published genomic sequence are identical, confirming the correct sequence of AS3. The extra C at nucleotide position 1,109 in the CG008 sequence suggests a possible sequencing error that results in a frame shift and a stop codon at position 1,152 of the CG008 sequence.

With the above information in hand, it was observed that several epidemiological studies support a link between breast and prostate cancers implying shared genetic suppressor elements in both disease states (Thiessen, (1974) *Cancer* 34:1102–1107; Tulinius et al., (1992) *Br. Med. J.* 305: 855–857). For example, studies of breast cancer families with high loss of heterogenicity (LOH) in the BRCA2 area showed that high prostate cancer incidence also occurred in 4 out of 5 families examined (Gudmundsson et al., (1995) *Cancer Res.* 55:4830–4832). Further, in the majority of the male relatives with prostate cancer in these families (86%), allelic losses in the BRCA2 area were also detected with some of these mutations occurring in the region immediately downstream of the BRCA2 gene (Gudmundsson et al., (1995) *Cancer Res.* 55:4830–4832; Van den Berg et al., (1996) *Br. J. Cancer* 74:1615–1619; Cleton-Jansen et al., (1995) *Br. J. Cancer* 72:1241–1244).

Moreover, it was noted that putative suppressors in the immediate vicinity of BRCA2 are not only limited to sex hormone-related cancers. For example, recent studies on chronic lymphoid leukemia detected a 1 Mb allelic loss in this region, with no mutations in the BRCA2 gene, pointing to a cryptic suppressor next to this gene (Garcia-Marco et al., (1996) *Blood* 88:1568–1575; Caldas et al., (1997) *Proc. Am. Assoc. Cancer Res.* 38:191). As indicated herein, the coding sequence of AS3 lies within this area. Thus, AS3 (or AS3-related molecules) may be associated with a number of diseases and conditions at several different levels involving, e.g., genomic alterations (including deletions and/or mutations at the chromosomal level), altered transcription or transcript production, and/or altered protein or protein expression levels. Thus, "AS3 related molecules" include, nucleic acid fragments or probes derived from the genomic locus (or an AS3 cDNA), AS3 or AS3 related proteins or protein fragments.

In addition to foregoing, the ability to determine AS3 protein expression levels, altered AS3 proteins, and/or AS3 protein expression patterns in, for example, different tissue samples (such a biopsy sample from, e.g., the prostate) may be desired. To this end, several antibodies have been developed that specifically bind the AS3 polypeptide. Briefly, computer aided sequence analysis of the AS3 protein was performed in order to identify several antigenic areas of the AS3 protein that were suitable for use as an immunogen. Accordingly, oligopeptides corresponding to amino acid residues 711–727 and 1,369–1387 of SEQ ID NO: 4 were synthesized and used to raise antibodies in, respectively, rabbits and chickens (egg yolk immunoglobulin Y). The resultant antibodies were both tested against cellular extracts derived from either LNCaP-FGC or MCF7-AR1 cells induced with androgen to express AS3 protein and both antibody preparations recognized a protein band of the expected size for AS3 protein. Thus, these antibodies can be used for performing, for example, immunocytochemistry on various cell samples (e.g., biopsies of the prostate) for various prognostic and diagnostic determinations.

Accordingly, it was concluded that the AS3-related molecules and AS3-specific antibodies disclosed herein are useful prognostic/diagnostic probes for evaluating diseases (e.g., the aforementioned cancers) that are associated with, or map to, the AS3 locus or are associated with altered AS3 protein expression.

EXAMPLE 5

Use of AS3 Molecules in the Treatment of Prostate Cancer

In this example, the use of AS3 as a marker in guiding the appropriate administration of hormone therapy for prostate cancer is discussed.

It was determined that expression analysis of the AS3 transcript demonstrated proliferation arrest-specific induction patterns, starting soon (4–6 h) after androgen exposure (Geck et al., (1997) *J. Steroid Biochem. Mol. Biol.* 63: 211–218). AS3 levels peaked at 18–20 h, about 4 h before the commitment for proliferative shutoff was detected, suggesting that this gene is a candidate for a shutoff mediator. Furthermore, expression of the AS3 transcript positively correlated with proliferation arrest as this gene was expressed only in shutoff-positive cell lines and variants. In addition, LNCaP-FGC cells proliferated maximally in CDHuS supplemented with 30 pM R1881 and under these conditions AS3 was not expressed. When AS3 was strongly induced in the presence of hormone (i.e., 0.3–30 nM of R1881), the cells were inhibited from proliferating. An additional observation that indicates the AS3 gene codes for an inhibitor of the proliferation of prostate cells is the increase of AS3 mRNA levels in the rat prostate when proliferation was arrested by prolonged androgen administration. In addition, comparable effects in MCF7-AR1 cells have been observed. Finally, significant homology between the fungal gene bimD and AS3 was found. Importantly, it was noted that overexpression of bimD in *Aspergillus nidulans* results in a cell cycle arrest in G1/S phase and observe a similar cell cycle arrest and concordant peak expression of AS3 in mammalian cells induced to undergo androgen-induced proliferative shutoff (Denison et al., (1992) *Genetics,* 134:1085–1096; Geck et al., (1997)*J. Steroid Biochem. Mol. Biol.* 63: 211–218).

Based on these observations, it was concluded that AS3 expression is a useful marker of responsiveness of prostate cancer cells to the inhibitory effect of androgens. In order to make the tumor regress, avoid reoccurrence, and maintain an acceptable quality of life, patients presenting this response may be treated with alternate cycles of antiandrogens and androgens. Androgens have a biphasic effect on the normal prostate: an initial phase of increased proliferation (Step 1) followed by a phase of inhibition (Step 2).

Prior to the invention, prostate cancer has been treated by hormone ablation (castration, antiandrogens) to take advantage of Step I. Usually after a significant regression, the remaining tumor cells become resistant and the tumor and/or metastases relapse. The invention avoids this problem by allowing the clinician to subject patients to an intermittent therapy. This is based on a classification of patients who have an increased chance to be responsive to the intermittent hormone therapy. Patients not showing AS3 positive cancer cells would then be subjected to alternative therapies (chemotherapy, radiation, etc.). In contrast, the protocol for AS3 positive patients would be to first administer antiandrogens, to block the proliferative effect and return PSA levels to normal, and then to treat the patient with physiological but high doses of androgen to elicit Step 2. The invention allows the clinician to confidently assess the initial hormone dependence of the tumor (i.e., whether tumor cells express AS3 in response to hormone) and determine when to re-expose the patient to hormone. Importantly, the use of intermittent hormone therapy allows the clinician to determine exactly when cells are no longer responding to hormone such that hormone treatment can be withdrawn before the cells become refractory to hormone treatment and untreatable. If the patient develops metastases capable of being biopsied, assaying AS3 levels as described herein would allow a renewed attempt to reduce the proliferation of those cancer cell by increasing the androgen concentration of the treatment. This important aspect of the invention should allow the clinician to lower the rate at which clones of cells develop hormone resistance and become capable of multiplying and metastasizing without androgen stimulation. Moreover, this new treatment regime affords a better quality of life for the patient because, unlike with constant hormone treatment, sexual drive and potency are recovered.

EXAMPLE 6

Antisense Assay for Demonstrating that AS3 is an Androgen-Induced Suppressor of Cell Proliferation In this example, an inducible antisense assay is provided for demonstrating that AS3 is an androgen-inducible suppressor of cell proliferation.

To demonstrate androgen-inducible AS3 suppressor activity in a proliferating cell (i.e., proliferative shut off activity), clonal cell lines were derived in which the presence or absence of AS3 could be controlled using an inducible AS3 antisense gene. The prediction was that cells incubated in the presence of androgen would have reduced levels of proliferation as compared to the same cells in the absence of androgen or cells in the presence of androgen but in which levels of AS3 had been experimentally ablated. Thus, cells incubated in the presence of androgen, but also induced to express antisense AS3 gene transcript which removes cellular levels of the AS3, would be predicted to grow like wild type cells because, even though the cells were being exposed to androgen, there would be insufficient AS3 to mediate the androgen signal reducing cell growth. This is precisely what was observed (see, e.g., Table 1), thereby demonstrating that AS3 is an androgen-induced suppressor of cell proliferation.

In order to develop the foregoing novel cell lines in which to demonstrate that AS3 mediates the androgen-induced shutoff effect, an inducible transgene encoding an AS3 antisense transcript (or empty vector as a negative control) was genetically engineered into a retroviral vector backbone for efficient, stable, integration into cells. In particular, the AS3 antisense gene was cloned into the Clontech pRe-vTRE™ retroviral vector under the control of a tetracycline sensitive promoter. The promoter has seven repeats of the bacterial tetO operator sequence upstream of the minimal CMV promoter which can be bound by the tetracycline transactivator (tTA). The tTA is a fusion protein between the bacterial tetracycline repressor and the V 16 herpes virus transactivator. The tetracycline transactivator is sensitive for tetracycline such that, in the presence of tetracycline, the transactivator cannot bind the tetracycline promoter so the transgene is "off" and conversely, in the absence of tetracycline, the gene is "on" (i.e., the Tet-Off™ system; see, e.g., Clontech pRevTRE™ manual for further details).

To stably introduce the foregoing inducible vectors into cells, the vectors were first transfected into a packaging cell line (PT67) under drug selection (hygromycin). After 2–3 weeks of selection, the surviving packaging cells were used as a source of supernatants containing infectious virions containing the inducible transgene.

The supernatants containing the highest amounts of virions were then used to infect the STFX1 cell line, a derivative of the MCF7-AR1 that has a tetracycline transactivator gene stably integrated. During the cloning and selection procedures, cells were maintained in 1 $\mu$g/mL of tetracycline to suppress the expression of the inducible transgenes.

In order to characterize the cell lines expressing AS3 antisense and the "control" cell lines having vector without insert, cells were incubated in the presence (i.e., the transgene is off) and absence of tetracycline (i.e., the transgene is on) and, after 36 hours, assayed for transcript expression using RT-PCR under standard conditions, To determine the affect of androgen induced AS3 suppression of cellular growth, cells lines showing high levels of inducible AS3 antisense expression were chosen for further study. Cells were seeded onto coverslips in standard growth medium and allowed to grow for 5 days in the presence of 10 $\mu$g/ml tetracycline (hereafter "tet"). Then, the medium was changed to i) 10 $\mu$g/ml tet, or ii) no tet for 36 hours as indicated in Table 1. Then, vehicle or 10 nM of the androgen R1881 was added. Finally, 24 hours later, the cells were treated with 10 $\mu$g/ml of bromodeoxyuridine (BrdU) for several hours to measure the percent of cells actively proliferating as a function of BrdU incorporation during DNA replication. The cells were then fixed, Hoechst stained, and the percent number of BrdU-labeled cells was determined using immunocytochemistry (using standard BrdU labeling regents and protocols from Boheringer).

As clearly indicated in Table 1, administration of the androgen R1881 results in a significant decrease in the number of proliferating cells in S phase (compare to sample 1 where cells are not treated with androgen) when cellular levels of AS3 are unaffected because the transgene vector is empty and uninduced (sample 2), empty and induced (sample 4), or encoding AS3 but uninduced (sample 6). In stark contrast, when AS3 levels are reduced by antisense expression in the absence of tetracycline, the androgen R1881 no longer induces a proliferative shutoff (compare sample 8 with sample 6).

TABLE 1

Analysis of the effect of tetracycline and androgen on the percent BrdU-labeled nuclei of STFX1 cells containing vector only or AS3 antisense constructs

| Sample | Treatm nt | % Prolif rating C IIs (M an +/− S.E.) |
|---|---|---|
| 1 | vector, +tet, −A | 35.0 +/−1.7 |
| 2 | vector, +tet, +A | 9.4 +/−1.7 |
| 3 | vector, −tet, −A | 36.6 +/−2.7 |
| 4 | vector, −tet, +A | 10.7 +/−0.9 |
| 5 | Antisense, +tet, −A | 34.7 +/−1.0 |
| 6 | Antisense, +tet, +A | 9.7 +/−0.6 |
| 7 | Antisense, −tet, −A | 32.2 +/−1.5 |
| 8 | Antisense, −tet, +A | 29.1 +/−1.6 |

Vector denotes STFX1 cells expressing empty vector under tetracycline control. Tetracycline is abbreviated tet; A denotes 10 nM R1881. Antisense denotes STFX1 cells expressing AS3-antisense under tetracycline control. Tetracycline represses the expression of the vector and the AS3 antisense. Each data point represents the mean of 8–9 low power fields containing about 150–200 cells/field. Data were analyzed using the Mann-Whitney test; significance was measured at $p < 0.001$.

This experiment further shows that the expression of the empty vector neither interferes with the androgen-mediated shutoff, nor results in toxic effects.

Accordingly, it is concluded that androgen induced suppression of cell proliferation (or proliferative shutoff) is modulated by AS3 because expression of an AS3 antisense that reduces cellular levels of AS3 results in the blocking of androgen-induced AS3-mediated suppression of cell growth.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. An isolated nucleic acid molecule selected from the group consisting of:
   (a) a nucleic acid molecule comprising the nucleotide sequence set forth in SEQ ID NO:1; and
   (b) a nucleic acid molecule comprising the nucleotide sequence set forth in SEQ ID NO:3.

2. An isolated nucleic acid molecule which encodes a polypeptide comprising the amino acid sequence set forth in SEQ ID NO:2.

3. An isolated nucleic acid molecule consisting of a fragment of at least 250 nucleotides of a nucleic acid comprising the nucleotide sequence of SEQ ID NO:1 or 3, or a complement thereof.

4. An isolated nucleic acid molecule comprising nucleotides 1–5253 of SEQ ID NO: 1.

5. An isolated nucleic acid molecule comprising the nucleic acid molecule of any one of claims 1, 2, 3 and 4 and a nucleotide sequence coding a heterologous polypeptide.

6. A kit comprising the nucleic acid of any of claims 1, 2, 3 and 4 for measuring AS3 (Androgen Shutoff Gene 3) RNA.

7. A vector comprising the nucleic acid molecule of any one of claims 1, 2, 3 and 4.

8. The vector of claim 7, which is an expression vector.

9. An isolated host cell transfected with the expression vector of claim 8.

10. A method of producing the polypeptide of SEQ ID NO: 2, comprising culturing the isolated host cell of claim 9 in an appropriate culture medium, thereby producing the polypeptide of SEQ ID NO: 2.

11. A method of obtaining the AS3 (Androgen Shutoff Gene 3) polypeptide of SEQ ID NO: 2, the method comprising:
   (a) providing an isolated cell with DNA encoding the AS3 (Androgen Shutoff Gene 3) polypeptide of SEQ ID NO: 2, the DNA being positioned for expression in the cell;
   (b) culturing the cell under conditions for expressing the DNA; and
   (c) isolating the AS3 polypeptide, whereby an AS3 (Androgen Shutoff Gene 3) polypeptide is obtained.

* * * * *